US005440017A

United States Patent [19]
MacLeod

[11] Patent Number: 5,440,017
[45] Date of Patent: Aug. 8, 1995

[54] T-CELL LYMPHOMA CDNA CLONES

[75] Inventor: Carol L. MacLeod, San Diego, Calif.

[73] Assignee: Research Development Foundation, Carson City, Nev.

[21] Appl. No.: 2,999

[22] Filed: Jan. 11, 1993

Related U.S. Application Data

[60] Division of Ser. No. 686,322, Apr. 11, 1991, Pat. No. 5,312,733, which is a continuation of Ser. No. 509,684, Apr. 13, 1990, abandoned.

[51] Int. Cl.⁶ .................. A61K 39/00; C07K 15/00
[52] U.S. Cl. ...................... 530/350; 435/69.1; 435/69.3; 935/11; 935/12; 536/23.1
[58] Field of Search .......... 435/69.1, 69.3, 320.1; 530/350; 935/11, 12; 536/23.1

[56] References Cited

PUBLICATIONS

MacCleod et al, Cancer Rese. 44:1784–1790 (1984). "A. Murne . . . System for the in vitro Development of Thymoma".
MacCleod et al, Mol. & Cell. Biol. 10(7): 3663–3674 (1980) "Activat. T Cells Express a Novel Gene on Chromo 8 . . . ".
Wilkinson et al, Developmental Biol. 141:451–455 (1990).
"A Novel Oncofetal Gene is Expressed in a Stage Specific . . . ".
Pierce et al, Cancer Research, 48: 1996–2004 (1988) "Tumors as Caricatures of the Process of Tissue Renewal".

Primary Examiner—David L. Lacey
Assistant Examiner—T. Michael Nisbet
Attorney, Agent, or Firm—Benjamin Adler

[57] ABSTRACT

The present invention provides novel DNA sequences, recombinant DNA (rDNA) molecules, processes for producing novel T-cell proteins expressed in T-cell development, the novel T-cell proteins in substantially pure form and antibodies which bind to the novel proteins. More particularly, it relates to novel DNA sequences expressed in appropriate hosts and the novel T-cell proteins produced in these hosts. The present invention also provides novel transmembrane proteins in substantially pure form, rDNA molecules encoding transmembrane proteins and processes for producing the novel transmembrane proteins. The DNA sequences and recombinant DNA molecules of this invention are characterized in that they are expressed by T lymphoma cells and have at least one of the following characteristics: (1) is expressed in normal thymus, activated spleen cells, or gut associated lymphoid tissue, (2) is expressed in ovarian tissue, normal liver and/or in a stage specific manner in embryonic development and (3) encode novel transmembrane proteins having multiple membrane spanning domains.

6 Claims, 32 Drawing Sheets

CCTAACTGACAAAGTGGGGAGAGTAAGGTGTGCGCAAACAGGACAAGTTGGGTCATGGGGAGT
                                                           MetGlySer

ATGAAGAACATCCTGAAATCTGTCTACAAAAGGCAAACTCGAACCTGCTACCTTAACTCTAAA
MetLysAsnIleLeuLysSerValTyrLysArgGlnThrArgThrCysTyrLeuAsnSerLys

ACTGGTATAGCTGGTGAACAGTTTATCTCAGGAGGACCTGCCTTGATCTTGCATAAAGATGGC
ThrGlyIleAlaGlyGluGlnPheIleSerGlyGlyProAlaLeuIleLeuHisLysAspGly

CAGGGTATAACCCAAATCATATGTTTCACTACTAATGTACTTCCACTTTCCTCAAGCAAGTTA
GlnGlyIleThrGlnIleIleCysPheThrThrAsnValLeuProLeuSerSerSerLysLeu

CGGGAAATGATTGACATTTTTGTACACCAACTTCTGGTCTTCGTTGGCACATTTTCGGGTCTG
ArgGluMetIleAspIlePheValHisGlnLeuLeuValPheValGlyThrPheSerGlyLeu

AGTCTCCTCATGTTTCAAGGAACCTGGTTCTGGCAGATGGCGTTTGTGCTGTACCCCCCATGT
SerLeuLeuMetPheGlnGlyThrTrpPheTrpGlnMetAlaPheValLeuTyrProProCys

TTTTGCTGGCATTATGCATCAATCCTTATCCTCATTGGAGTAAAATATGCTTTGGCCAACTGG
PheCysTrpHisTyrAlaSerIleLeuIleLeuIleGlyValLysTyrAlaLeuAlaAsnTrp

GCTGACCGTGAGCAAGAATCAGAAGAAGAAGTATGATCTTGAAGTCTTTCTTGATAAGCCTTC
AlaAspArgGluGlnGluSerGluGluGluVal

CTTGTCTGAGGCTGACTCCATGCTGTTTGTACTTCCAGTTTTGTTAAAGTGTTGGACTTTAAG
CATGCCATGTAATTCAAGACCAATCATAATTGTTTTCCAAAGTTTAGTTTCGTGTCCATTTAT

FIG. 3A

```
TTCAAAGGACATGCTCTCCCTGGGAGTTTCTTCTTCGCCATGGGCTTTTGGTGGACT  120
PheLysGlyHisAlaLeuProGlySerPhePhePheAlaMetGlyPheTrpTrpThr  (23)

ACATTATTACGTCGGACAGAGATTTGGGAAGGAGTTGTTGTGCTTTTAATGTCTCTC  240
ThrLeuLeuArgArgThrGluIleTrpGluGlyValValValLeuLeuMetSerLeu  (63)

CAGTGGAACCAGATCCTGGGCTGGCATCACACAACCATGTACTTATTCTTTGGGCTA  360
GlnTrpAsnGlnIleLeuGlyTrpHisHisThrThrMetTyrLeuPhePheGlyLeu  (103)

ATGTTATCAATTGCCATCTTTGTGGAGACATTTATGTTCTACAACCACACACACGGT  480
MetLeuSerIleAlaIlePheValGluThrPheMetPheThrAsnHisThrHisGly  (143)

GTTGCCTTCTTGGAGTTCCTCGTAAAGAACAACGCACTTCTGGAGCTCCTGCGGTGC  600
ValAlaPheLeuGluPheLeuValLysAsnAsnAlaLeuLeuGluLeuLeuArgCys  (183)

GGAAGTGCTACATGGAACCTGTCAGATATTCAAAATAAAATGTTTCTCTCAATGTGC  720
GlySerAlaThrTrpAsnLeuSerAspIleGlnAsnLysMetPheLeuSerMetCys  (223)

TTAGTCAAGTCTAGGCTGAGGAAGGGCTGCACCTCAGAAGTTGGACTCCTGAAGCAT  840
LeuValLysSerArgLeuArgLysGlyCysThrSerGluValGlyLeuLeuLysHis  (263)

TCCCTTTGCGTTGCCTTTGTTCATGGCTTTGTTTCCTGACCTCTGGTCTCAAGAACA  960
                                                          (273)

TATCTTACTTTCAGCTCTGAAAGAACCATGAGTGATAAATTCACTTTTTACACTGTG  1080
TAAAAATATTTTTTTTATTTTCCGGGTAGATACCTTCAA                   1184
```

FIG. 3B

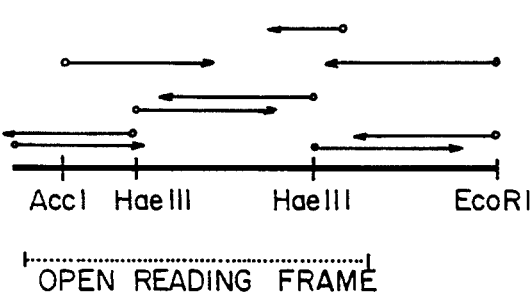

FIG. 5

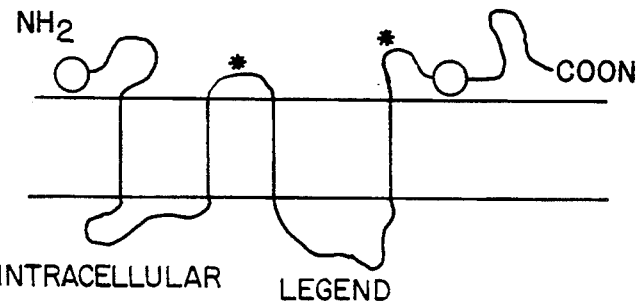

FIG. 4

* POTENTIAL N-GLYCOSYLATION SITE
o GLOBULAR HYDROPHOBIC DOMAIN

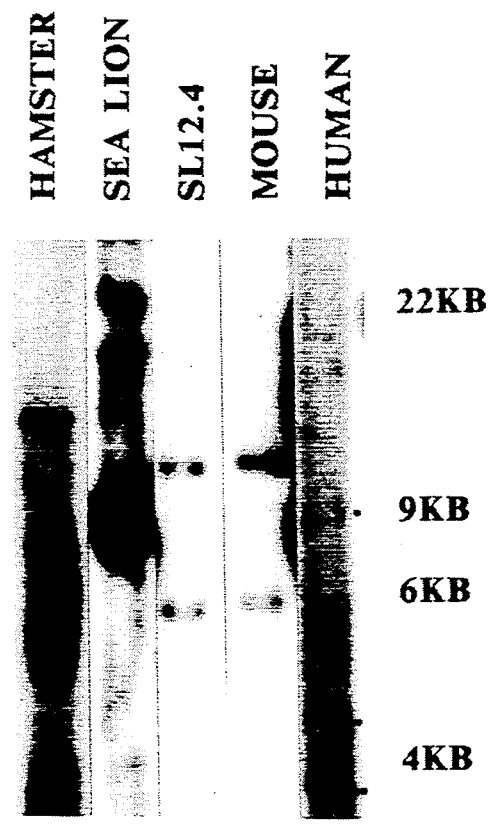
FIG. 9
1.7kb
1.5kb
2 X   0.2 X
SSPE
FIG. 8
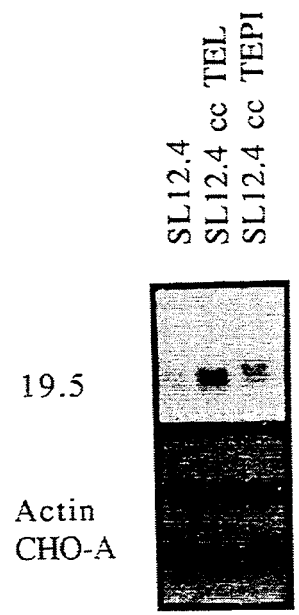
19.5
Actin
CHO-A
FIG. 10

FIG. 14
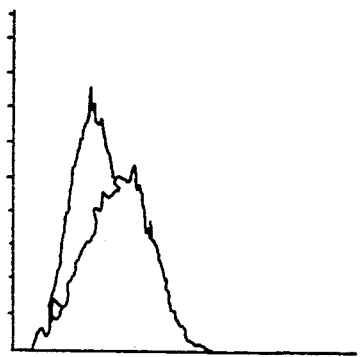
ST4.F6
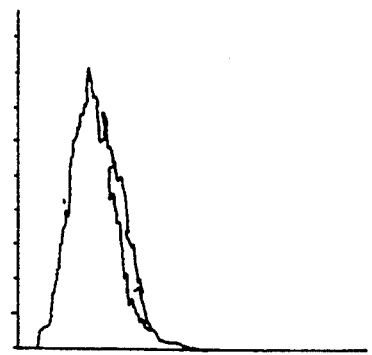
ST4.F6  W/OLIGO PEPTIDE
FIG. 15
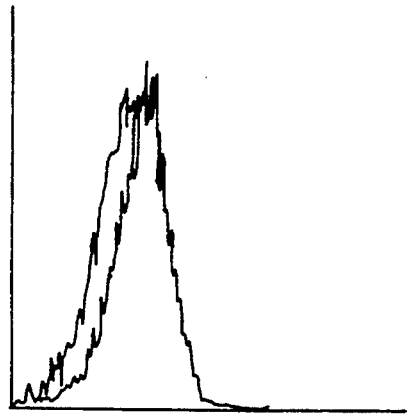

cDNA and predicted protein sequence of 20.5 (TEA)

gggtgtctttcctcatcgctgccctggcctcggttatggccggcctttgctatgctgaattt agctgtgggccttcatcactggctggaatctcatcctgtcatatgtcataggtacgtccagt ttttcaaaacgtacttcaaaatgaattacactggtctggcagagtatccagacttctttgcc gggtgaataaattttacagctattaatatcctggtccttctctttgtcATGGTGGCTGGGT
                           M V A G AGCAAGTGCTAGAGAACCACCTTCTGAGAACGGAACAAGCATCTACGGGGCTGGCGGCTTTA
 A S A R E P P S E N G T S I Y G A G G <u>F</u>

GGGCTTTGACTGCATTGCAACAACCGGTGAAGAGGTTCGGAATCCACAAAAGGCGATCCCCA
 G F D C I A T T G E E V R N P Q K A I <u>P</u>

TTTAACGCTTATGATGCCTTACTACCTCCTGGATGAGAAAAGTCCACTCCCAGTCGCGTTTG
 L T L M M P Y Y L L D E K S P L P V A F

ATCAACAAGTCTTCTTGGATCCATTTTCCCAATGCCTCGTGTAATCTATGCTATGGCGGAGG
 S T S L L G S I F P M P R V I Y A M A E

TGCTACTTTGTCATCGGGTGCAGTGGCAGCTGTGATGGCCTTTCTTTTTGACCTGAAGGCCC
 <u>A T L S S G A V A A V M A F L F D L</u> K A

GCTTATTCTCAGGTACCAACCTGGCTTGTGTTACGAGCAGCCCAAATACACCCCTGAGAAAG
 <u>L I</u> L R Y Q P G L C Y E Q P K Y T P E K

GCAAGGACAGGGTTTCAGCCTACGAACCCTCTTCAGCCCCTCTGCCCTGCCCACACGACAGT

FIG. 19A

```
ggggcccgagtacccaagactggatctgcgtatctatacacttacgtcacggtcggag      120
gtcgcaagagcatggagtggcacctttgacgaacttcttaataaacagattggccagt      240
gtgtgccttgtattactcctggcaggtcttttatcttttggagtaaaagagtctgctt     360
TTGTGAAAGGAAATGTGGCTAACTGGAAGATCAGTGAAGAGTTTCTCAAAAATATATC     480
 F  V  K  G  N  V  A  N  W  K  I  S  E  E  F  L  K  N  I  S
TGCCCTATGGCTTTACAGGGACGTTGGCTGGTGCTGCAACGTGCTTTTATGCCTTTGT     600
 M  P  Y  G  F  T  G  T  L  A  G  A  A  T  C  F  Y  A  F  V
TCGGAATAGTGACGTCCTTACTTGTCTGCTTTATGGCTTACTTTGGGGTTTCTGCAGC     720
 I  G  I  V  T  S  L  L  V  C  F  M  A  Y  F  G  V  S  A  A
AGTATGTCAGATGGGGCCCCGCCAAATACGTTGTCGCAGCAGGCTCCCTCTGCGCCTT     840
 E  Y  V  R  W  G  P  A  K  Y  V  V  A  A  G  S  L  C  A  L
ATGGGTTGCTTTTCAAATGTCTAGCTCAAATCAATTCCAAAACGAAGACACCAGTAAT     960
 D  G  L  L  F  K  C  L  A  Q  I  N  S  K  T  K  T  P  V  I
TCGTGGACATGATGTCTATTGGCACCCTCATGGCCTACTCTCTGGTGGCAGCCTGTGT    1080
 L  V  D  M  M  S  I  G  T  L  M  A  Y  S  L  V  A  A  C  V
AAACTCTGGAATCATGTACCAATGCGACTTTGAAGAGCGAGTCCCAGGTCACCATGCT    1200
 E  T  L  E  S  C  T  N  A  T  L  K  S  E  S  Q  N  T  M  L
CGGCTTCCCTTGTGAGCTTTCTGGTGGGATTCCTGGCTTTCCTCATCCTGGGCTTGAG    1320
```

FIG. 19B

```
   Q   G   Q   G   F   S   L   R   T   L   F   S   P   S   A   L   P   T   R   Q
TATTCTAACCACGTATGGCGTCCAGGCCATTGCCAGACTGGAAGCCTGGAGCCTGGCTCTTC
   I   L   T   T   Y   G   V   Q   A   I   A   R   L   E   A   W   S   L   A   L
GAATCAGCAAAAAGTAGCCTTCATGGTCCCGTTCTTACCGTTTCTGCCGGCCTTCAGCATCC
   N   Q   Q   K   V   A   F   M   V   P   F   L   P   F   L   P   A   F   S   I
CTGGATGGCGCTTGGCTTTCTGATCTATTTCGCCTATGGCATTAGACACAGCTTGGAGGGTA
   W   M   A   L   G   F   L   I   Y   F   A   Y   G   I   R   H   S   L   E   G
AGAAGAAAAGTCCGTCATGCAAGCAAATGACCATCACCAAAGAAACCTCAGCTTACCTTTCA
   E   E   K   S   V   M   Q   A   N   D   H   H   Q   R   N   L   S   L   P   F
ttaacaatgagtacactgtggccggatgccaccatcgtgctgggctgtcgtgggtctgctgt
attctgtgtctgaggagactgcctgagagcactcctcagctatatgtatccccaaaacagta
tctgtgacataattccagcatggtaattggtggcatatactgcacacactagtaaacagtat
tttctttattaggtatatgaccatcagtttggacatactgaaatgccatccctgtcaggat
aatgcatatatccttctcctacttgctaagacagctttcttaaacggccagggagagtgttt
```

FIG. 19C

```
    S   A   S   L   V   S   F   L   V   G   F   L   A   F   L   I   L   G   L   S
TCGCCCTGTTCCTTGTCCTCTGCGCTGCCGTCATTCTGACCATTTGGAGGCAGCCACA 1440
    L   A   L   F   L   V   L   C   A   A   V   I   L   T   I   W   R   Q   P   Q
TGGTCAACATTTACTTGATGGTCCAGTTAAGTGCGGACACTTGGATCAGATTCAGCAT 1560
    L   V   N   I   Y   L   M   V   Q   L   S   A   D   T   W   I   R   F   S   I
ACCCCAGGGACGAAGAAGACGATGAGGATGCCTTTTCAGAAAACATCAATGTAGCAAC 1680
    N   P   R   D   E   E   D   D   E   D   A   F   S   E   N   I   N   V   A   T
TACTTCATGAAAAGACAAGTGAATGttgatgctggccctcggtcttaccacgcatacc 1800
    I   L   H   E   K   T   S   E   C
ggacatggcttgcctaacttgtacttcctcctccagacagcttctcttcagatggtgg 1920
tgtccgtgtgcgtacatgtatgtctgcgatgtgagtgttcaatgttgtccgttattag 2040
attgctgaatagagatgtattctgtatatgtcctaggtggctggggaaatagtggtgg 2160
gtttaacagtggtcatgggtggggaagggataaggaatgggcattgtctataaattgt 2280
ctttcctctgtatgacaagatgaagaggtagtctgtggctggagatggccaatcc      2397
```

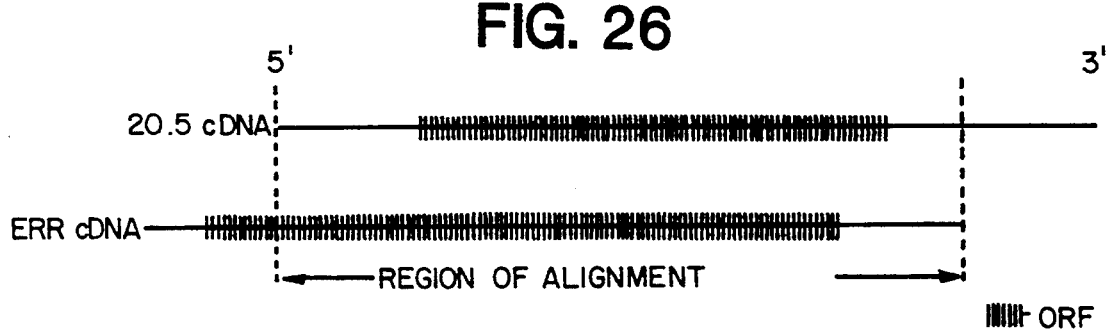

FIG. 27A

```
  1    GGGTGTCTTTCCTCATCGCTGCCCTGGCCTCGGTTATGGCCGGCCTTTGCTATGCTG
       I II III I II IIIII II IIIII II IIIIIIIIIII IIIII I I I
400    ATCTCCTTCTTGATTGCTGCTCTCGCCTCCGTGCTGGCCGGCCTGTGCTACGGCG

121    AGCTGTGGGCCTTCATCACTGGCTGGAATCTCATCCTGTCATATGTCATAGGTACGT
       IIII IIIIIIIIIIIIIIIIIIIIIIII II II II II II  IIII IIIII I
518    AGCTTTGGGCCTTCATCACTGGCTGGAACCTGATTCTCTCCTACATCATCGGTACTT

241    TTTTCAAAACGTACTTCAAAATGAAT  TACACTGGT CTGGCAGAGTATCCAGACT
       I I I III I  IIIII II I III IIIIII I  II III
638    TCTCACGTCAGCACATGGCCCTGAATGCTCCTGGGGTGCTGGCCCAAACCCCGGACA

358    CTTGGGTGAA TAAATTTTTACAGCTATTAATATCCTGGTCCTTCTCTTTGTCATGG
       I III II IIIIIII II  III III IIIIIII I  III II III
758    CCATGGTCAACAAAATTTTCACCTGTATCAATGTCCTGGTCTTGTGCTTCATCGTGG

477    TATCAGCAAGTGCTAGAGAACCACCTTCTGAGAACGGAACAAGCATCTACGGGGCTG
       III I  II II I II II I I  I IIII I II       IIIIII I
869    TCTC  C   TG TA ACAA CAACGACACA AACGTGA AA       TACGGTGAGG

597    TTGTGGGCTTTGACTGCATTGCAACAACCGGTGAAGAGGTTCGGAATCCACAAAAGG
       I IIIIIIIIIIIIIIIIII II II II IIIIII II  III III II IIII
974    TCGTGGGCTTTGACTGCATCGCCACCACAGGGGAAGAAGTCAAGAACCCCCAGAAGG

717    CAGCTTTAACGCTTATGATGCCTTACTACCTCCTGGATGAGAAAAGTCCACTCCCAG
       I IIII I IIIIII IIIIIIIIIIIIII I IIIIII I III II II III I
109    CCGCTCTCACGCTCATGATGCCTTACTTCTGCCTGGACATCGACAGCCCGCTGCCTG

837    CCTTATCAACAAGTCTTCTTGGATCCATTTTCCCAATGCCTCGTGTAATCTATGCTA
       I IIII II IIIII II II IIIIII II II IIIII II II IIIIIIII I
1214   CACTTTCCACCAGTCTCCTAGGCTCCATGTTTCCCATGCCCCGAGTTATCTATGCCA

957    TAATTGCTACTTTGTCATCGGGTGCAGTGGCAGCTGTGATGGCCTTTCTTTTTGACC
       IIII II III I I II II II    I II IIIIIIIIIIII II IIIII I
1334   TAATCGCCACTGTGACCTCAGGCGCCATTGCTGCTGTGATGGCCTTCCTCTTTGAAC

1077   GTGTGCTTATTCTCAGGTAC      CAACCTGGCTTGTGTTACGAGCAGCCCA
       IIII I  I I IIIII          IIIIII II III II I III
1454   GTGTTTGGTCTTACGGTACCAGCCAGAACAACCTAATCTGGTATACCAGATGGCCA
```

```
AATTTGGGGCCCGAGTACCCAAGACTGGATCTGCGTATCTATACAGTTACGTCACGGTCGGAG
 !!!!!! !!!!! !! !!!!!!!!! !! !! !! !! !! !!!! !!!!! !!!!! !! !
AGTTTGGTGCCCCTGTCCCCAAGACGGGCTCAGCCTACCTCTACAGCTACGTGACGGTGGGGG

CCAGTGTCGCAAGAGCATGGAGTGGCACCTTTGACGAACTTCTTAATAAACAGATTGGCCAGT
! !! !! !!!!!!!!! !!!!!!! !! !!!!!!!! !! !    !! !   !! !!   !!!
CAAGCGTGGCAAGAGCCTGGAGTGCGACTTTTGACGAGCTGATAGGCAAGCCCATCGGAGAGT

TCTTTGCCGTGTGCCTTGTATTACTCCTGGCAGGTCTTTTATCTTTTGGAGTAAAAGAGTCTG
! !!!!!! !!!    !  !  !   !!  !!!! !! !!! !! !!!! !! !! !!!!! !
TATTTGCTGTGATTATAATTATCATCTTAACAGGACTGTTAACTCTTGGCGTGAAGGAGTCAG

TGGCTGGGTTTGTGAAAGGAAATGTGGCTAACTGGAAGATCAGTGAAGAGTTTCTCAAAAATA
!!!! !!!!! !!!!!!!!    !    !!!!!!!!! !! !!!  !  !!!       !!!!!!
TGTCCGGGTTCGTGAAAGGCTCCATTAAAAACTGGCAGCTCA CG  GAG      AAAAATT

GCGCCTTTATGCCCTATGGCTTTACAGGGACGTTGGCTGGTGCTGCAACGTGCTTTTATGCCT
! !! !!!!!!!!!!! !!! !! ! !!    !! ! !! !! !! !! !!!!!!!!!!!!!
GAGGGTTTATGCCCTTTGGATTCTCTGGTGTCCTGTCAGGGGCAGCGACCTGCTTTTATGCCT

CGATCCCCATCGGAATAGTGACGTCCTTACTTGTCTGCTTTATGGCTTACTTTGGGGTTTCTG
! !! !! ! !! !! !!! !!!!! ! !!  ! !!!!! !! !! !!!!!!!! !! !!! !
CCATTCCTGTGGGCATCGTGGCGTCCCTCCTCATTTGCTTCATAGCGTACTTTGGCGTGTCCG

TCGCGTTTGAGTATGTCAGATGGGGCCCCGCCAAATACGTTGTCGCAGCAGGCTCCCTCTGCG
!! !! !! !    ! !!!!   !! !! !!!! !! !!  !!!!! !!!!!!!
GTGCCTTCAAGCACCAGGGCTGGGAAGAAGCTAAGTACGCAGTGGCCATTGGCTCTCTCTGCG

TGGCGGAGGATGGGTTGCTTTTCAAATGTCTAGCTCAAATCAATTCCAAAACGAAGACACCAG
!!!! !! !!!!!! ! !! !! !!!! ! ! !! !!!!!!!! !  !! !! !!!!!! !
TGGCTGAAGATGGACTACTGTTTAAATTTTTGGCCAAAATCAACAATAGGACCAAAACACCCG

TGAAGGCCCTCGTGGACATGATGTCTATTGGCACCCTCATGGCCTACTCTCTGGTGGCAGCCT
!!!!!! !!! !!!!!!! !  !!!!! !!!!!!!!! !!! !!!! !!!!!!! !!!!! !!!!
TGAAGGACCTGGTGGACCTCATGTCCATTGGCACTCTCCTGGCTTACTCTTTGGTGGCTGCCT

AATACACCCCTGAGAAAGAAACTCTGGAATCATGTACCAATGCGACTTTGAAGAGCGAGTCCC
! !!!!   !!!   !!!         ! ! !!!! ! !  ! ! !! !!!! !!
GAACCACCGAGGAGCTAGATCGAGTAG ATCA GAATGAGCTGGTCAGTG CCAGTGAATCAC
```

FIG. 27B

```
1188 AG   GTCACCATGCTGCAAGGACAGGGTTTCAGCCTACGAACCCTCTTCAGCCCCT
        ||   |   |  |  ||  ||   ||    ||  |  || ||  ||    |||
1571 AGACAGGCTTTTTACCGGTAGCCGAGAAGTTTTCTCTGAAATCCATCCTCTCACCCA

1302 TCCTCATCCTGGGCTTGAGTATTCTAACCACGTATGGCGTCCAGGCCATTGCCAGAC
        ||  ||||  |  ||| |  |  |||   |  |||   ||||| |  |||   |
1691 CTCTTATCATCACCGTGTGCATTGTGGCCGTGCTTGGAAGAGAGGCCCTGGCCGAAG

1422 CCATTTGGAGGCAGCCACAGAATCAGCAAAAAGTAGCCTTCATGGTCCCGTTCTTAC
        |||  |||||||  ||||| |||   ||   |  |   |   || |  || |  |  |
1811 TCATCTGGAGACAGCCTGAGAGCAAGACCAAGCTCTCATTTAAGGTACCCTTTGTCC

1542 CTTGGATCAGATTCAGCATCTGGATGGCGCTTGGCTTTCTGATCTATTTCGCCTATG
        | ||| || | ||   | ||||||  |  | || |  ||   ||||||||| |||
1931 CGTGGGTCCGGTTTGCAGTGTGGATGCTGATAGGTTTCACCATCTATTTCGGTTATG

1659 CAGAAAACATCAATGTAGCAACAGAAGAAAAGTCCGTCATGCAAGCAAATGAC CAT
        ||   |||    |||   |||    ||   ||   || |||   ||||   |
2051 TGGACCAGTGCAAATGACGTGCAGCCCCACCCACCAGGGTGACAGCGGTTGACGGGT

1778 CCCTCGGTCTTACCACGCATACCTTAACAATGAGTACACTGTGGCCGG  ATGCCAC
        |||  |   |  ||||     ||   |  |    |   |   |  ||  ||
2167 CCCCCAATGTCACCAAAGCTGGTTTGCTGCCAGCTCGTGAGATCCTGGTCATTTCTG

1896 CAGACAGCTTCTCTTCAGATGGTGGATTCTGTGTCTGAGGAGACTGCCTGAGAGCAC
        ||||    |  |||| |  ||  |   |  |   |  ||  |  |||          |
2286 CGGCCGG GCGCTTC GCTGCTGCGGCCCCAG CAGAAGGGA GCCC   CCCTTC

2016 AGTGTTCAATGTTGTCCGTTATTAGTCTGTGAcataattccagcatggtaattggtg
        ||  |   |    |   | ||  || ||
2397 CACACTCCA GATGGC  TAGTGAGCCTCTCCEND 2425   Matches 1212,
        taggtggctggggaaatagtggtggtttctttattaggtatatgaccatcagtttgg
        ggaatgggcattgtctataaattgtaatgcatatatccttctcctacttgctaagac
        tctgtggctggagatggccaatcc 2397
```

FIG. 27C

```
CTGCCCT   GCCCACACGACAGTCGGCTTCCCTTGTGAGCTTTCTGGTGGGATTCCTGGCTT
  ! !    !!!! !  !  !! !    !!!!!! ! !!  !  !! !!!! !!
AGAACGTGGAGCCCTCCAAATTCTCAGGGCTAATTGTGAACATTTCAGCCGGCCTCCTAGCCG

TGGAAGCCTGGAGCCTGGCTCTTCTCGCCCTGTTCCTTGTCCTCTGCGCTGCCGTCATTCTGA
 !  !  !!!   !    ! !  !  ! !   !!   ! !!!!!!!!   !! !        !
GGACACTGTGGGCAGTCTTTGTAATGACAGGGTCAGTCCTCCTCTGCATGCTGGTGACAGGCA

CGTTTCTGCCGGCCTTCAGCATCCTGGTCAACATTTACTTGATGGTCCAGTTAAGTGCGGACA
!  ! !! !! ! !!! !!!!!! !! !!!!! !  ! !!! !  ! !!!!            !! !!
CCGTACTTCCTGTCTTGAGCATCTTCGTGAACATCTATCTCATGATGCAGCTGGACCAGGGCA

GCATTAGACACAGCTTGG AGGGTAAC CCCAG GGACGAAGAAGACGATGAGGATGCCTTTT
! !!  !  !!!!!  !  !! !! !  !  !!!!!! ! !!    !     ! !!   !    !
GGATCTGGCACAGTGAGGAAGCGTCCCTGGCTGCTGGCCAGGCAAAGACTCCTGACAGCAACT

CACCAAAGAAACCTCAGCTTACCTTTCATACTTCATGAAAAGACAAGTGAATGTTGATGCTGG
 !! !!!! !!! !    !!! !!!  ! !   !    !   !    !
GCCCGTAGAAGCCTGGG   ACC CTCACAATCTCTCCACTCATGCCTCAGGATCAGCTCACA

CATCGTGCTGGGCTGTCGTGGGTCTGCTGTGGACATGGCTTGCCTAACTTGTACTTCCTCCTC
!  !!!   !  !!  !   !             !! !! !!! !   !!   !!! ! !!! ! !  !
GACAGTCCCTTGGTTTACTCATCTCCCTCTGAACAAAGAAAGCAGCCCTTCTCCTTGC CGGC

TCCTCAGCTATATGTATCCCCAAAACAGTATGTCCGTGTGCGTACATGTATGTCTGCGATGTG
!!!!!  !    !  !            !  !   !!! !! !     !!    !! ! !!!!!
TCCTC TCACTTGGGAAGCAGGCCTCCCTCCCTCCCTGGGACCACCCTGGCATCGCCCATGTG gcatatagtgcacacactagtaaacagtatattgctgaatagagatgtattctgtatatgtaa Mismatches 789, Unmatched 74 acatactgaaatgccatcccctgtcaggatgtttaacagtggtcatgggtggggaagggataa
agcagctttcttaaacggccagggagagtgtttctttcctctgtatgacaagatgaagaggta
```

FIG. 27D

```
Amino Terminus (Extracellular)
                            *                              *
  1    M V  A G F V K G M V A N W K I S E E F L K N I S A S A R E P P S E N G T S I Y
204    - -  I V V S G F V K G S I K N W Q L T E - - K N F S C N N N D - T - M - V K Y Region 1      Transmembrane 1
 40    G A G G F M P Y G F T G T L A G A A T C F Y A F V G F D C I A T T G E E V R N P
236    G E G G F M P F G F S G V L S G A A T C F Y A F V G F D C I A T T G E E V K N P Transmembrane 2
 80    Q K A I P I G I V T S L L V C F M A Y F G V S A A L T L M M P Y Y L L D E K S P
276    Q - K A I P V G I V A S L L I C F I A Y F G V S A A L T L M M P Y F C L D I D S P 120    L P V A F E Y V R W G P A K Y V V A A G S L C A L S T S L L G S I P F M P R V I
316    L P G A F K N Q G W E E A K Y A V A I G S L C A L S T S L L G S M F P M P R V I Transmembrane 3
160    Y A M A E D G L L F K C L A Q I N S K T K T P V I A T L S S G A V A A V M A F L
356    Y A M A E D G L L F K F L A K I N N R T K T P V I A T V T S G A I A A V M A F L
```

FIG. 29A

```
                    Transmembrane 4
200  F D L K A L V D M M S I G T L M A Y S L V A A C V L T L R Y Q P G    L C Y E
396  F - L K D L - - V D L M S - - I G T L L A Y S L V A A C V L V L R Y Q - P    - - T Q 237  Q P K Y T P E K E T L E S C T M A T L K S E S Q V T M L Q    G Q G F S L R T L F
436  M A R T T E E L D R V D Q   N E L V S A S E S Q T G F L P V A E K F S L K S I L
                                                   Transmembrane 5
276  S P S A L   P T R Q S A S L V S F L V G F L A F L I L G L S T L T T Y G V Q A I
475  S - S P K N V E P S K F S G L I V N I S A G L L A A L I I T V C I V A V L G R E A L
                              Transmembrane 6      Region 2
315  A R L E A W S L A L L A L F L V L C A A V I L T ( I W R Q P Q N Q Q K V A F M V P
515  A - E G T L W - - A V F V M T G S V L L C M L V T G I I W R Q P E S K T K L S F K V P
                                                          Transmembrane 7
355  F L P F L P A F S I L V N I Y L M V Q L S A D T W I R F S I W M A L G F L I Y F
555  F - V P V L P V L S I F V N I Y L M M Q L D Q G T W V R F A V W M L I G F T I Y F 395  A Y G I R H S L E  GNPRDEEDDEDAFSENIMVATEEKSVMQANDHHQRNLSLPFILHEKTSEC  459
595  - Y G I - W H S E E  ASLAAGQAKTPDSNLDQCKU  623

FIG. 29B
```

```
TCCAATACAAAACACTTATTTGAACATTACTTTACTTAGAAAGAACCCCACTATAGCTGA
AGCCAAAGCAAAGTTTAGCTGAAAACCTAAGAAGATATTTTAATAGAGAACCCCTGTCTC
CAAAGGAAAATATCTCCTAATGGAAACTGAATCTGCCATCAATCCTTCAGATGTTATCTC
GGAGGGGAGGATTTCATGAAGGGAGCCAGCTGGAGGGCCCACTGCAGGTTCCCAAGTGGG
AAGGTACAGGCATTGCGCATAGCCACATGGCCGGCACACTTAACATTCCCAGGATTTCTG
ATTAGCTAGCTTTCACTCTTCTGTGACTCTTTTGTCTTCTGTGACTGACTTGGTGCATGG
AACACTGGCTTTATGTTATCTTCTTAGATATCAGGATGAAGTGCTCAGGTGCCATCTGCC
CTCTACCTGGTTTTCTTCATGCCTGGAGAGATGCACAGTGCACAGATGTCTATAGCGGAT
TGAATAATTCCCTGGCCAAGGCTAAGGGACTGCCACAATCGTTTACCTAACTCAGTCTCA
CAATGTTTTACTTAATTCAATCTTATTGAATTTTTTCTATGTTGTGTATAATAAACAGAG
AGAAACAGATGTCCCTACCAACTGGAAAGTTGTTGTTTAAATACCCTGTTGGTTAAAATG
TCAAACTTACTGTTTAAACACTCATTAGCCATATCCAACTTGAAACATATGCTATTGCTT
GACCATATTAAGCCAGACTTTGAACTAGGTCAATGTCCCTGGAGTATAAATGTACCATAG
AGCTTCCTTGCTTCTTGCAAAAAGTCCTCAGGCGAACATAACTTTGACCCCATAAAGGT
CCCTCACTTCTCACAGCCTTGATTTGCTGAAGACCTTCACACCCTGGCCCAATCTAGGA
AATGTTCTACTCATGTAAGAATTCTTCATCTCTCCCACCTCATAACAAGTGTCCTTTGTC
CCTATAATAATGGCATAGAAAAATCCCTGAAAGACCCAAATTGGGCAACAATACAGATCA
GATCAGAGCCTTCATGGGCCCGACAATGGAGAATTGTATTTCTTAAAAAGTGTGTGATCA
TATTTGTCTGAGCTGCAATAGAGACCATAGTATAAGCTCAGAAGAGAACTTTAGTGGCTC
CCTAATTTCCTTAGACTGGCTTATATTTCAACCTTTTCCTGTTATTTTTTCCTGATAGGG
TAGGTGTACATTTCTAACTGTAACTGATAAGGAAGTATAGAGACACCCATCACCTTCAAA
ACGGGCTATTCACAATTCTGCCTATTCTATTCAGTGTGGGA
```

FIG. 36

```
GCTGGGACCATCCCATAATGCATCAATTGGAAACCTCAATTCAAACTATGGAGGATCCAG
CCTTGTTACAAATAGTCGATCAGCTTCGATGGTCGGAACACATCGGGAAGATTCAGTCAG
TCTCAATGGCAATCATTCGGTCCTGTCTAGTACTGTTGCTGCCTCAAACACAGAACTGAA
CCATAAAACACCAGAAAATTTCAGAGGTGGTGTACAAAATCAGTCTGGAAGTGTTGTTCC
AACAGAAATCAAGACTGAAAACAAAGAAAAAGATGAAAACCTTCATGAACCTCCTTCATC
AGATGACATGAAATCAGATGATGAGTCCTCCCAGAAAGACATCAAGGTCTCATCTAGGGG
CAGAACAAGCAGTACCAATGAAGACGAGGATCTGAATCCAGAACAGAAAATCGAAAGGGA
GAAGGAAAGGCGGATGGCTAACAATGCCAGAGAGCGCCTGTCGTGCGGGATATTAACGAG
GCGTTCAAGGAGCTTGGCCGAATGTGTCAGCTTCATTTGAAGAGTGAAAAACCTCAGACA
AAACTTCTCATTCTTCATCAGGCCGTGGCAGTCATCCTTAGTCTAGAACAGCAAGTGAGA
GAGAGGAACCTCAACCCCAAAGCAGCCTGCCTTAAGAGAAGAGAAGAAGAAAAAGTCTCT
GCTGCGTCACGAGCCGCCCAACACGTTGCCAGGAGCCCATCCTGGGCTTAGTGAGTCTAC
CAACCCTATGGGTCATCTGTAAACATCAGCCAGTTCCAGAGTCATCAGTAGGCTAAATAG
AAGGTGACCTCTCCTCATAAGATTTGGACAACTCAGATTATCTGAAGACACAAACCTGGC
AGGAGGGAGAAGAAAAAGCAAAACACTTGAAACCAGAAACTCATATGTAACCCTGTGATC
AAAGCAACTGGTCAGCACTTCATCAGACCTGAGCATAGGAAGCTCAGCAGAGACCGTCGG
CCGTGAGTGTTTGCAGCATATCACTCTGCTGTAATCAGTGTGTCGCTTCTGCACAATCAG
AGACTGTCTCATCTCTCACTCAACGTGAAGTGCTTGTGCCTAAACTGAATTGACAAATGC
ATTGTAACTACAAATTTTATTTATTGTTATGGAACTGTGAGGTCTACATATAAAGGGAAA
AGTTCATGTGGGAAGCTGATGTACACTCAGCTGATGCCAGCATTGTTAAAGCTGTTCACA
GAGCAGTGGCAACCATTGGCCCTTAGCATTCCCGGCATACCTGTTAGTGTCTTAAAAAGG
AAGGGAGTCCTTTGTTGCCCTCTCCGACCTTCGCCATATGAATAGTGATTTCCATGAAAT
AGGAAAAATATTACTTCGTATAGCATTTCTCTCTGTTTTTTCACTCATTTTTATTTCCT
CTTTGTGGGTGTTATATTTGACTGAGTCTGCATAGTTTATGGTCACAGTCCAGAACCCTC
CTTGCAGTCCTGTATGCTTTGTCATGTCCTTGAAGTGATAAGCAGACACCATCTGTGACC
ATAGCCTAGCTAATATTTTGAAAGGGGAAGTTTTGTCCCCTGGATTTGCCCCCAAATAAA
CATTGCTTTATTTCTAATAATCACTAAGACTTTTCAGGCTTCTAGGTTTCATAGTAAAGC
TATAATAGCAAGAAGTGTAACTTACAAGGGAGAGTTTACTTTTTAGGAATTGCTTTGTTT
TCCGAGCAGTAAGTACTACACAATATAGTACTTGTAAAGTGTTAGCTGATAAGTAAGCAC
AGAATGCATTCAGTACAATACAAAGATGACTTTTCCTGGTGAGTCTCCGGGACAGGCAGT
GTGATGAATGCACTCAACCGCTCTGAGGCTAATTACCTATGGAATCCAAGAGCAATGGTC
ACGGTTCCTTACCCTAGCTTTACTTCTGTCCTTTGAGTTGGCTGGTCCGTGGGGGTGGG
GCAGGAGGGTGACTTAATCACCTGCAAACCACCTGCCCCCACCCCAAGAAGAGCCAGATT
AGCACCGAGCTGTACCTGTCAGTCTGTCTTAGCATTATGCATTAAGGCACCCTCTGTCTC
TAATCCCTTACAGTTGTTTTAAGACACAGTAATCACTTTAAACTTCCATGAAATCTGTC
TTCCACCACAGCACCCTGGGAGAGAAAAACATGCTAAGCGTGATGGTCTTGGCTAAGTAA
CTCCTTAAAGCCAATAGCAGTGGCAGTCTGCACAGAAGAAAAATCCCAAGTCGTTCTGTA
ACTTAGAGACACCGGAGAATTTTGAAAGAACAAAAACCATGAAGACAGCACTTCAGATCC
TCCATCAGGACTCTGGTGAACACGTCAGTCTTTGGCAACTTAGTGGACTTAATTTGTAT
ATGTTCTCCAGTTAGATCAGACTCTATCTGTGGCCTTGTTCTTCATTTCAGTGTTAATCA
GCTAAAACAGCAGTTGTTGCTATGATGTGTGAGTGAACATAAGCCACTGCCTGGCCTTTT
TTCTTCAGAGGGTGTCGTCTTTTTCGCTATATTAGACTTTGCAGTATGCCCAG
```

```
cagcctggttaagtccaagctgggtgatctgtaagacagtgactgagtATGGATCATTTG    60
 Q  P  G  -  V  Q  A  G  -  S  V  R  Q  -  L  S  M  D  H  L      4

AACGAGGCAACTCAGGGGAAAGAACATTCAGAAATGTCTAACAATGTGAGTGATCCGAAG   120
 N  E  A  T  Q  G  K  E  H  S  E  M  S  N  N  V  S  D  P  K     24

GGTCCACCCGCCAAGATTGCCCGCCTGGAGCAGAACGGGAGCCCTCTAGGAAGAGGAAGG   180
 G  P  P  A  K  I  A  R  L  E  Q  N  G  S  P  L  G  R  G  R     44

CTTGGGAGCACAGGTGGAAAGATGCAGGGAGTGCCTTTAAAACACTCGGGCCATCTCATG   240
 L  G  S  T  G  G  K  M  Q  G  V  P  L  K  H  S  G  H  L  M     64

AAAACCAACCTTAGGAAAGGAACCATGTTACCAGTTTTCTGCGTGGTGGAACATTATGAA   300
 K  T  N  L  R  K  G  T  M  L  P  V  F  C  V  V  E  H  Y  E     84

AACGCCATTGAGTATGATTGCAAGGAGGAGCACGCGGAATTTGTATTGGTGAGAAAGGAT   360
 N  A  I  E  Y  D  C  K  E  E  H  A  E  F  V  L  V  R  K  D    104

ATGCTTTTCAACCAGCTGATAGAGATGGCGTTGCTGTCTCTAGGCTATTCACACAGCTCT   420
 M  L  F  N  Q  L  I  E  M  A  L  L  S  L  G  Y  S  H  S  S    124

GCTGCCCAAGCCAAAGGGCTCATCCAGGTTGGGAAGTGGAATCCAGTTCCACTGTCGTAT   480
 A  A  Q  A  K  G  L  I  Q  V  G  K  W  N  P  V  P  L  S  Y    144

GTGACAGATGCCCCTGATGCCACGGTGGCAGACATGCTTCAAGATGTGTATCATGTGGTC   540
 V  T  D  A  P  D  A  T  V  A  D  M  L  Q  D  V  Y  H  V  V    164

ACCCTCAAAATTCAGTTACACAGTTGCCCTAAACTAGAAGACTTGCCTCCTGAACAATGG   600
 T  L  K  I  Q  L  H  S  C  P  K  L  E  D  L  P  P  E  Q  W    184

TCGCACACCACAGTAAGGAATGCTCTGAAGGACTTACTGAAAGATATGAACCAGAGTTCG   660
 S  H  T  T  V  R  N  A  L  K  D  L  L  K  D  M  N  Q  S  S    204

TTGGCCAAGGAGTGCCCCCTTTCACAGAGCATGATCTCCTCCATTGTGAACAGCACGTAC   720
 L  A  K  E  C  P  L  S  Q  S  M  I  S  S  I  V  N  S  T  Y    224

TATGCAAATGTCTCAGCAGCAAAATGTCAAGAATTTGGAAGGTGGTACAAACATTTCAAG   780
 Y  A  N  V  S  A  A  K  C  Q  E  F  G  R  W  Y  K  H  F  K    244

AAGACAAAGGATATGATGGTTGAGATGGATAGTCTGTCTGAACTATCCCAGCAAGGTGCC   840
 K  T  K  D  M  M  V  E  M  D  S  L  S  E  L  S  Q  Q  G  A    264

AACCACGTCAATTTTGGCCAGCAGCCTGTCCCAGGAAACACAGCTGAGCAGCCTCCATCC   900
 N  H  V  N  F  G  Q  Q  P  V  P  G  N  T  A  E  Q  P  P  S    284

CCTGCGCCCAGCTCTCACGGCAGTCAGCCCTCTGTCCGGACCCCTCTTCCGAACCTGCAC   960
 P  A  P  S  S  H  G  S  Q  P  S  V  R  T  P  L  P  N  L  H    304

CCTGGGCTTGTGTCAACACCGATCAGTCCTCAGCTGGTCAACCAACAGCTGGTGATGGCT  1020
 P  G  L  V  S  T  P  I  S  P  Q  L  V  N  Q  Q  L  V  M  A    324

CAGTTGCTGAACCAGCAGTATGCAGTGAACAGACTCTTAGCCCAGCAGTCCTTAAACCAA  1080
 Q  L  L  N  Q  Q  Y  A  V  N  R  L  L  A  Q  Q  S  L  N  Q    344

CAGTACTTGAACCACCCTCCCCCTGTCAGTAGGTCTATGAACAAGCCTTTGGAGCAGCAA  1140
 Q  Y  L  N  H  P  P  P  V  S  R  S  M  N  K  P  L  E  Q  Q    364

GTTTCCACAAACACGGAGGTCTCTTCTGAAATCTACCAGTGGGTGCGGGATGAACTGAAA  1200
 V  S  T  N  T  E  V  S  S  E  I  Y  Q  W  V  R  D  E  L  K    384

CGAGCCGGAATCTCACAGGCAGTATTTGCACGCGTGGCTTTTAACCGAACTCAGGGATTG  1260
 R  A  G  I  S  Q  A  V  F  A  R  V  A  F  N  R  T  Q  G  L    404

CTTTCTGAAATCCTCCGAAAGGAAGAGGACCCCAAGACTGCATCCCAGTCTCTGCTGGTA  1320
 L  S  E  I  L  R  K  E  E  D  P  K  T  A  S  Q  S  L  L  V    424

AACCTTCGGGCTATGCAGAATTTCTTACAGTTGCCGGAAGCCGAAAGAGACCGGATATAC  1380
 N  L  R  A  M  Q  N  F  L  Q  L  P  E  A  E  R  D  R  I  Y    444
```

```
CAGGATGAGAGGGAAAGGAGCTTGAACGCAGCCTCAGCCATGGGTCCTGCCCCGCTGCTG 1440
 Q  D  E  R  E  R  S  L  N  A  A  S  A  M  G  P  A  P  L  L   464
AGCACACCACCCAGCCGCCCTCCCCAGGTGAAAACAGCTACCCTTGCCACTGAGAGAAAT 1500
 S  T  P  P  S  R  P  P  Q  V  K  T  A  T  L  A  T  E  R  N   484
GGGAAGCCAGAGAACAATACTATGAACATTAATGCCTCCATTTATGACGAGATTCAGCAG 1560
 G  K  P  E  N  N  T  M  N  I  N  A  S  I  Y  D  E  I  Q  Q   504
GAAATGAAGCGTGCTAAAGTGTCCCAAGCACTGTTTGCAAAGGTTGCCGCCACAAAAAGC 1620
 E  M  K  R  A  K  V  S  Q  A  L  F  A  K  V  A  A  T  K  S   524
CAGGGATGGCTGTGTGAGCTGTTGCGCTGGAAAGAAGATCCTTCTCCAGAAAACAGGACC 1680
 Q  G  W  L  C  E  L  L  R  W  K  E  D  P  S  P  E  N  R  T   544
CTGTGGGAGAACCTGTCGATGATCCGAAGATTTCCCAGTCTGCCCAGCCGAGCGCGAGTG 1740
 L  W  E  N  L  S  M  I  R  R  F  P  S  L  P  S  R  A  R  V   564
CCATCATATGAGCAGGAGAGCAATGCTGTGCATCACCATGGCGACAGACCTCCCCACATC 1800
 P  S  Y  E  Q  E  S  N  A  V  H  H  H  G  D  R  P  P  H  I   584
ATCCACGTTCCAGCAGAACAGATTCAGCAGCAGCAACAGCAGCAGCAGCAACAGCAGCAG 1860
 I  H  V  P  A  E  Q  I  Q  Q  Q  Q  Q  Q  Q  Q  Q  Q  Q  Q   604
CAGCAGCAGCCACCGCCGCCACCGCCGCAGCCACAGCCACAGCCCCAGGCAGGCCCCAGC 1920
 Q  Q  Q  P  P  P  P  P  P  Q  P  Q  P  Q  P  Q  A  G  P  S   624
CTCCCCCCACGGCAGCCCACCGTGGCCTCCTCCGCGGAGTCCGATGAGGAAAACCGGCAG 1980
 L  P  P  R  Q  P  T  V  A  S  S  A  E  S  D  E  E  N  R  Q   644
AAGACCAGGCCACGAACCAAAATTTCCGTGGAAGCCCTGGGGATCCGCGCCCGAATAAGC 2040
 K  T  R  P  R  T  K  I  S  V  E  A  L  G  I  R  A  R  I  S   664
CTAAGCCTCAAGCAGCATATTtgatagtctggcgtaaccatcatcgagatctgcagcatc 2100
 L  S  L  K  Q  H  I  -  -     671
ctgaagcggcgcaatatgctcactggctacctgcatcaggcttttttttgtttctcccgc 2160
ctcccggatctgcgcccgaataagcctcaagcagcatatttgatagtctggcgtaaccat 2220
catcgagatccttcagagtttcatccaagatgtgggcctgtacccagatgaagaggctat 2280
ccagactctgtctgcacagctggacctcccgaagtacaccatcatcaagttctttcagaa 2340
ccagcggtactaccttaagcaccatggcaagctgaaggacaactccggcttggaggtgga 2400
ttgtggccgagtacaaagatgaggagttgcttaaggatttggaagagagcgtcaggataa 2460
aaacgccaacacccttttctcagtgaaactagaggaagagctgtcggtggaagggagcac 2520
agacgttaatgccgacttgaaagactgagagaacagtattcttttcagccacaccaccgg 2580
tatttctaacaacatgagagtccaccttgtgttcactcagacaaaccttcattgtttatt 2640
xxxxxxxxxxgttggccaatttggccaatgaatcttcggaaacttgcacaaacaggaagg 2700
aagttggaaggacaggacagccagcactcaaggttttactgtgttttccaaaactgcttg 2760
gcagccccgggtgaagcgtcaaggacgtgtttggtagaatttgtgttcaagggctgcaccc 2820
aggtgttgtaccctgtcagcatgatacccagaaattggttttcctttgattattattatt 2880
ctggagcctcaaataagcattaaatcttctgtggattgtattgccttttctttagtaact 2940
tcttgtaatcccgccacacatgctttggaaactggcccttatttaaagagaaaaagaa 3000
aaaaaaaagagagagagtttgttactcgattgtatgttaaaaaaaagaactatagac 3060
tgtggaatgcagtttaaagatgacatatgccaacaaatgccttgtattgtatggcactgc 3120
cgtaattaaaatttgttttttattttgaaataaaagttcactgtaattttttcatcc 3180
tcattattacatgattttttttttaaggaaaagaaaatgtgaaacacaatttagtccctt 3240
gttatttatttgtagctcctgcagcatcatgtcataattaagttttttggagatttctgt 3300
taaatgtaatgttgctttcccatcctgatttcctttctatttataactgtatttgatgg 3360
gcagtaaaacaaagtgtcttaaaagttttaaatagagaaaaatgtgctttacacagttgc 3420
ctataaaaagtctatgttatccaagcaattcactctagaagcttcggtctcgttgttgta 3480
tgcaattttactatcatgcaaataagcttaggtaaataaaactaatagatcaccttaga 3540
aaattatgcaattaatgtgaaataattgatgtttgcaatgtgtcttcctttggtttaca 3600
atcaattttaaagcgacatctgtataaagtttctgtataaaggtgtatttctttttatg 3660
agtttatggctatgaaaacaccagctattttgttacaggggtaccgagctcagtgtatca 3720
cagttttctttatgcagaaatgtgctgattaggagtggttattgactgtaagtacacgat 3780
taaaattgtttgtatggtaaaaaaaaaaaaaaaaaaaaa
```

FIG. 38B

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1301 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Mouse
        ( B ) STRAIN: AKR1 Jackson
        ( C ) INDIVIDUAL ISOLATE: SL12 cell line
        ( F ) TISSUE TYPE: Lymphoma
        ( G ) CELL TYPE: T-cell
        ( H ) CELL LINE: SL12.3 and SL12.4

( v i i ) IMMEDIATE SOURCE:
        ( B ) CLONE: 19.1

( x i ) SEQUENCE DESCRIPTION: SEQ ID NO:1:

```
TCCAATACAA  AACACTTATT  TGAACATTAC  TTTACTTAGA  AAGAACCCCA  CTATAGCTGA      60
AGCCAAAGCA  AAGTTTAGCT  GAAAACCTAA  GAAGATATTT  TAATAGAGAA  CCCCTGTCTC     120
CAAAGGAAAA  TATCTCCTAA  TGGAAACTGA  ATCTGCCATC  AATCCTTCAG  ATGTTATCTC     180
GGAGGGGAGG  ATTTCATGAA  GGGAGCCAGC  TGGAGGGCCC  ACTGCAGGTT  CCCAAGTGGG     240
AAGGTACAGG  CATTGCGCAT  AGCCACATGG  CCGGCACACT  TAACATTCCC  AGGATTTCTG     300
ATTAGCTAGC  TTTCACTCTT  CTGTGACTCT  TTTGTCTTCT  GTGACTGACT  TGGTGCATGG     360
AACACTGGCT  TTATGTTATC  TTCTTAGATA  TCAGGATGAA  GTGCTCAGGT  GCCATCTGCC     420
CTCTACCTGG  TTTTCTTCAT  GCCTGGAGAG  ATGCACAGTG  CACAGATGTC  TATAGCGGAT     480
TGAATAATTC  CCTGGCCAAG  GCTAAGGGAC  TGCCACAATC  GTTTACCTAA  CTCAGTCTCA     540
CAATGTTTTA  CTTAATTCAA  TCTTATTGAA  TTTTTCTAT   GTTGTGTATA  ATAAACAGAG     600
AGAAACAGAT  GTCCCTACCA  ACTGGAAAGT  TGTTGTTTAA  ATACCCTGTT  GGTTAAAATG     660
TCAAACTTAC  TGTTTAAACA  CTCATTAGCC  ATATCCAACT  TGAAACATAT  GCTATTGCTT     720
GACCATATTA  AGCCAGACTT  TGAACTAGGT  CAATGTCCCT  GGAGTATAAA  TGTACCATAG     780
AGCTTCCTTG  CTTCTTGCAA  AAAGTCCTCA  GGCGAACATA  ACTTTGACCC  CCATAAAGGT     840
CCCTCACTTC  TCACAGCCTT  GATTTGCTG   AAGACCTTCA  CACCCTGGCC  CAATCTAGGA     900
AATGTTCTAC  TCATGTAAGA  ATTCTTCATC  TCTCCCACCT  CATAACAAGT  GTCCTTTGTC     960
CCTATAATAA  TGGCATAGAA  AAATCCCTGA  AAGACCCAAA  TTGGGCAACA  ATACAGATCA    1020
GATCAGAGCC  TTCATGGGCC  CGACAATGGA  GAATTGTATT  TCTTAAAAAG  TGTGTGATCA    1080
TATTTGTCTG  AGCTGCAATA  GAGACCATAG  TATAAGCTCA  GAAGAGAACT  TTAGTGGCTC    1140
CCTAATTTCC  TTAGACTGGC  TTATATTTCA  ACCTTTTCCT  GTTATTTTTT  CCTGATAGGG    1200
TAGGTGTACA  TTTCTAACTG  TAACTGATAA  GGAAGTATAG  AGACACCCAT  CACCTTCAAA    1260
ACGGGCTATT  CACAATTCTG  CCTATTCTAT  TCAGTGTGGG  A                         1301
```

( 2 ) INFORMATION FOR SEQ ID NO:2:

( i ) SEQUENCE CHARACTERISTICS:
        ( A ) LENGTH: 2513 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Mouse
        ( B ) STRAIN: AKR1 Jackson
        ( C ) INDIVIDUAL ISOLATE: SL12 cell line
        ( F ) TISSUE TYPE: Lymphoma
        ( G ) CELL TYPE: T-cell
        ( H ) CELL LINE: SL12.3 and SL12.4

( v i i ) IMMEDIATE SOURCE:
        ( B ) CLONE: 19.2

( x i ) SEQUENCE DESCRIPTION: SEQ ID NO:2:

```
GCTGGGACCA  TCCCATAATG  CATCAATTGG  AAACCTCAAT  TCAAACTATG  GAGGATCCAG    60
CCTTGTTACA  AATAGTCGAT  CAGCTTCGAT  GGTCGGAACA  CATCGGGAAG  ATTCAGTCAG   120
TCTCAATGGC  AATCATTCGG  TCCTGTCTAG  TACTGTTGCT  GCCTCAAACA  CAGAACTGAA   180
CCATAAAACA  CCAGAAAATT  TCAGAGGTGG  TGTACAAAAT  CAGTCTGGAA  GTGTTGTTCC   240
AACAGAAATC  AAGACTGAAA  ACAAAGAAAA  AGATGAAAAC  CTTCATGAAC  CTCCTTCATC   300
AGATGACATG  AAATCAGATG  ATGAGTCCTC  CCAGAAAGAC  ATCAAGGTCT  CATCTAGGGG   360
CAGAACAAGC  AGTACCAATG  AAGACGAGGA  TCTGAATCCA  GAACAGAAAA  TCGAAGGGA    420
GAAGGAAAGG  CGGATGGCTA  ACAATGCCAG  AGAGCGCCTG  TCGTGCGGGA  TATTAACGAG   480
GCGTTCAAGG  AGCTTGGCCG  AATGTGTCAG  CTTCATTTGA  AGAGTGAAAA  ACCTCAGACA   540
AAACTTCTCA  TTCTTCATCA  GGCCGTGGCA  GTCATCCTTA  GTCTAGAACA  GCAAGTGAGA   600
GAGAGGAACC  TCAACCCCAA  AGCAGCCTGC  CTTAAGAGAA  GAGAAGAAGA  AAAAGTCTCT   660
GCTGCGTCAC  GAGCCGCCCA  ACACGTTGCC  AGGAGCCCAT  CCTGGGCTTA  GTGAGTCTAC   720
CAACCCTATG  GGTCATCTGT  AAACATCAGC  CAGTTCCAGA  GTCATCAGTA  GGCTAAATAG   780
AAGGTGACCT  CTCCTCATAA  GATTTGGACA  ACTCAGATTA  TCTGAAGACA  CAAACCTGGC   840
AGGAGGGAGA  AGAAAAAGCA  AAACACTTGA  AACCAGAAAC  TCATATGTAA  CCCTGTGATC   900
AAAGCAACTG  GTCAGCACTT  CATCAGACCT  GAGCATAGGA  AGCTCAGCAG  AGACCGTCGG   960
CCGTGAGTGT  TTGCAGCATA  TCACTCTGCT  GTAATCAGTG  TGTCGCTTCT  GCACAATCAG  1020
AGACTGTCTC  ATCTCTCACT  CAACGTGAAG  TGCTTGTGCC  TAAACTGAAT  TGACAAATGC  1080
ATTGTAACTA  CAAATTTTAT  TTATTGTTAT  GGAACTGTGA  GGTCTACATA  TAAAGGGAAA  1140
AGTTCATGTG  GGAAGCTGAT  GTACACTCAG  CTGATGCCAG  CATTGTTAAA  GCTGTTCACA  1200
GAGCAGTGGC  AACCATTGGC  CCTTAGCATT  CCCGGCATAC  CTGTTAGTGT  CTTAAAAAGG  1260
AAGGGAGTCC  TTTGTTGCCC  TCTCCGACCT  CGCCATATG   AATAGTGATT  CCATGAAAT   1320
AGGAAAAATA  TTACTTCGTA  TAGCATTTCT  CTCTGTTTTT  TTCACTCATT  TTTATTTCCT  1380
CTTTGTGGGT  GTTATATTTG  ACTGAGTCTG  CATAGTTTAT  GGTCACAGTC  CAGAACCCTC  1440
CTTGCAGTCC  TGTATGCTTT  GTCATGTCCT  TGAAGTGATA  AGCAGACACC  ATCTGTGACC  1500
ATAGCCTAGC  TAATATTTTG  AAAGGGGAAG  TTTTGTCCCC  TGGATTTGCC  CCCAAATAAA  1560
CATTGCTTTA  TTTCTAATAA  TCACTAAGAC  TTTTCAGGCT  TCTAGGTTTC  ATAGTAAAGC  1620
TATAATAGCA  AGAAGTGTAA  CTTACAAGGG  AGAGTTTACT  TTTTAGGAAT  TGCTTTGTTT  1680
TCCGAGCAGT  AAGTACTACA  CAATATAGTA  CTTGTAAAGT  GTTAGCTGAT  AAGTAAGCAC  1740
AGAATGCATT  CAGTACAATA  CAAAGATGAC  TTTTCCTGGT  GAGTCTCCGG  GACAGGCAGT  1800
```

```
GTGATGAATG CACTCAACCG CTCTGAGGCT AATTACCTAT GGAATCCAAG AGCAATGGTC    1860

ACGGTTCCTT ACCCTAGCTT TACTTCTGTC CTTTGAGTTG GCTGGTCCGT GGGGGGTGGG    1920

GCAGGAGGGT GACTTAATCA CCTGCAAACC ACCTGCCCCC ACCCCAAGAA GAGCCAGATT    1980

AGCACCGAGC TGTACCTGTC AGTCTGTCTT AGCATTATGC ATTAAGGCAC CCTCTGTCTC    2040

TAATCCCTTA CAGTTGTTTT TAAGACACAG TAATCACTTT AAACTTCCAT GAAATCTGTC    2100

TTCCACCACA GCACCCTGGG AGAGAAAAAC ATGCTAAGCG TGATGGTCTT GGCTAAGTAA    2160

CTCCTTAAAG CCAATAGCAG TGGCAGTCTG CACAGAAGAA AAATCCCAAG TCGTTCTGTA    2220

ACTTAGAGAC ACCGGAGAAT TTTGAAAGAA CAAAAACCAT GAAGACAGCA CTTCAGATCC    2280

TCCATCAGGA CTCTGGTGAA CACGTCAGTC TTTGGCGAAC TTAGTGGACT TAATTTGTAT    2340

ATGTTCTCCA GTTAGATCAG ACTCTATCTG TGGCCTTGTT CTTCATTTCA GTGTTAATCA    2400

GCTAAAACAG CAGTTGTTGC TATGATGTGT GAGTGAACAT AAGCCACTGC CTGGCCTTTT    2460

TTCTTCAGAG GGTGTCGTCT TTTTCGCTAT ATTAGACTTT GCAGTATGCC CAG           2513
```

(2) INFORMATION FOR SEQ ID NO:3:

(i) SEQUENCE CHARACTERISTICS:
        (A) LENGTH: 3819 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Mouse
        (B) STRAIN: AKR1 Jackson
        (C) INDIVIDUAL ISOLATE: SL12 cell line
        (F) TISSUE TYPE: Lymphoma
        (G) CELL TYPE: T-cell
        (H) CELL LINE: SL12.3 and SL12.4

(vii) IMMEDIATE SOURCE:
        (B) CLONE: 19.4

(xi) SEQUENCE DESCRIPTION: SEQ ID NO:3:

```
CAGCCTGGTT AAGTCCAAGC TGGGTGATCT GTAAGACAGT GACTGAGTAT GGATCATTTG      60

AACGAGGCAA CTCAGGGGAA AGAACATTCA GAAATGTCTA ACAATGTGAG TGATCCGAAG     120

GGTCCACCCG CCAAGATTGC CCGCCTGGAG CAGAACGGGA GCCCTCTAGG AAGAGGAAGG     180

CTTGGGAGCA CAGGTGGAAA GATGCAGGGA GTGCCTTTAA AACACTGGGG CCATCTCATG     240

AAAACCAACC TTAGGAAAGG AACCATGTTA CCAGTTTTCT GCGTGGTGGA ACATTATGAA     300

AACGCCATTG AGTATGATTG CAAGGAGGAG CACGCGGAAT TTGTATTGGT GAGAAAGGAT     360

ATGCTTTTCA ACCAGCTGAT AGAGATGGCG TTGCTGTCTC TAGGCTATTC ACACAGCTCT     420

GCTGCCCAAG CCAAAGGGCT CATCCAGGTT GGGAAGTGGA ATCCAGTTCC ACTGTCGTAT     480

GTGACAGATG CCCCTGATGC CACGGTGGCA GACATGCTTC AAGATGTGTA TCATGTGGTC     540

ACCCTCAAAA TTCAGTTACA CAGTTGCCCT AAACTAGAAG ACTTGCCTCC TGAACAATGG     600

TCGCACACCA CAGTAAGGAA TGCTCTGAAG GACTTACTGA AGATATGAA CCAGAGTTCG     660

TTGGCCAAGG AGTGCCCCCT TCACAGAGC ATGATCTCCT CCATTGTGAA CAGCACGTAC     720

TATGCAAATG TCTCAGCAGC AAAATGTCAA GAATTTGGAA GGTGGTACAA ACATTTCAAG     780

AAGACAAAGG ATATGATGGT TGAGATGGAT AGTCTGTCTG AACTATCCCA GCAAGGTGCC     840

AACCACGTCA ATTTTGGCCA GCAGCCTGTC CCAGGAAACA CAGCTGAGCA GCCTCCATCC     900

CCTGCGCCCA GCTCTCACGG CAGTCAGCCC TCTGTCCGGA CCCCTCTTCC GAACCTGCAC     960

CCTGGGCTTG TGTCAACACC GATCAGTCCT CAGCTGGTCA ACCAACAGCT GGTGATGGCT    1020
```

```
CAGTTGCTGA ACCAGCAGTA TGCAGTCAAC AGACTCTTAG CCCAGCAGTC CTTAAACCAA    1080
CAGTACTTGA ACCACCCTCC CCCTGTCAGT AGGTCTATGA ACAAGCCTTT GGAGCAGCAA    1140
GTTTCCACAA ACACGGAGGT CTCTTCTGAA ATCTACCAGT GGGTGCGGGA TGAACTGAAA    1200
CGAGCCGGAA TCTCACAGGC AGTATTTGCA CGCGTGGCTT TAACCGAAC TCAGGGATTG    1260
CTTTCTGAAA TCCTCCGAAA GGAAGAGGAC CCCAAGACTG CATCCCAGTC TCTGCTGGTA    1320
AACCTTCGGG CTATGCAGAA TTTCTTACAG TTGCCGGAAG CCGAAAGAGA CCGGATATAC    1380
CAGGATGAGA GGGAAAGGAG CTTGAACGCA GCCTCAGCCA TGGGTCCTGC CCCGCTGCTG    1440
AGCACACCAC CCAGCCGCCC TCCCCAGGTG AAAACAGCTA CCCTTGCCAC TGAGAGAAAT    1500
GGGAAGCCAG AGAACAATAC TATGAACATT AATGCCTCCA TTTATGACGA GATTCAGCAG    1560
GAAATGAAGC GTGCTAAAGT GTCCCAAGCA CTGTTTGCAA AGGTTGCCGC CACAAAAGC    1620
CAGGGATGGC TGTGTGAGCT GTTGCGCTGG AAAGAAGATC CTTCTCCAGA AAACAGGACC    1680
CTGTGGGAGA ACCTGTCGAT GATCCGAAGA TTTCCCAGTC TGCCCAGCCG AGCGCGAGTG    1740
CCATCATATG AGCAGGAGAG CAATGCTGTG CATCACCATG GCGACAGACC TCCCCACATC    1800
ATCCACGTTC CAGCAGAACA GATTCAGCAG CAGCAACAGC AGCAGCAGCA ACAGCAGCAG    1860
CAGCAGCAGC CACCGCCGCC ACCGCCGCAG CCACAGCCAC AGCCCCAGGC AGGCCCCAGC    1920
CTCCCCCCAC GGCAGCCCAC CGTGGCCTCC TCCGCGGAGT CCGATGAGGA AAACCGGCAG    1980
AAGACCAGGC CACGAACCAA AATTTCCGTG GAAGCCCTGG GGATCCGCGC CCGAATAAGC    2040
CTAAGCCTCA AGCAGCATAT TTGATAGTCT GGCGTAACCA TCATCGAGAT CTGCAGCATC    2100
CTGAAGCGGC GCAATATGCT CACTGGCTAC CTGCATCAGG CTTTTTTTG TTTCTCCCGC    2160
CTCCCGGATC TGCGCCCGAA TAAGCCTCAA GCAGCATATT TGATAGTCTG GCGTAACCAT    2220
CATCGAGATC CTTCAGAGTT TCATCCAAGA TGTGGGCCTG TACCCAGATG AAGAGGCTAT    2280
CCAGACTCTG TCTGCACAGC TGGACCTCCC GAAGTACACC ATCATCAAGT TCTTTCAGAA    2340
CCAGCGGTAC TACCTTAAGC ACCATGGCAA GCTGAAGGAC AACTCCGGCT GGAGGTGGA    2400
TTGTGGCCGA GTACAAAGAT GAGGAGTTGC TTAAGGATTT GGAAGAGAGC GTCAGGATAA    2460
AAACGCCAAC ACCCTTTTCT CAGTGAAACT AGAGGAAGAG CTGTCGGTGG AAGGGAGCAC    2520
AGACGTTAAT GCCGACTTGA AAGACTGAGA GAACAGTATT CTTTTCAGCC ACACCACCGG    2580
TATTTCTAAC AACATGAGAG TCCACCTTGT GTTCACTCAG ACAAACCTTC ATTGTTTATT    2640
NNNNNNNNNN GTTGGCCAAT TTGGCCAATG AATCTTCGGA AACTTGCACA ACAGGAAGG    2700
AAGTTGGAAG GACAGGACAG CCAGCACTCA AGGTTTTACT GTGTTTTCCA AAACTGCTTG    2760
GCAGCCCCGG GTGAAGCGTC AAGGACTGTT TGGTAGAATT TGTGTTCAAG GGCTGCACCC    2820
AGGTGTTGTA CCCTGTCAGC ATGATACCAG AAATTGGTTT CCTTTTGAT TATTATTATT    2880
CTGGAGCCTC AAATAAGCAT TAAATCTTCT GTGGATTGTA TTGCCTTTTC TTTAGTAACT    2940
TCTTGTAATC CCGCCACACA TGCTTTGGAA ACTGGCCCCT TATTTAAAG AGAAAAGAA    3000
AAAAAAAAG AGAGAGAGAG TTTGTTACTC GATTGTATGT TAAAAAAAG AACTATAGAC    3060
TGTGGAATGC AGTTTAAAGA TGACATATGC CAACAAATGC CTTGTATTGT ATGGCACTGC    3120
CGTAATTAAA ATTTGTTTTT TTATTTTGGA AATAAAAGTT CACTGTAATT TTTTTCATCC    3180
TCATTATTAC ATGATTTTTT TTTTAAGGA AAAGAAAATG TGAAACACAA TTTAGTCCTT    3240
GTTATTTATT TGTAGCTCCT GCAGCATCAT GTCATAATTA AGTTTTTGG AGATTTCTGT    3300
TAAATGTAAT GTTGCTTTCC CATCCTGATT TCCTTTCTAT TTATAACTGT ATTTTGATGG    3360
GCAGTAAAAC AAAGTGTCTT AAAAGTTTTA AATAGAGAAA AATGTGCTTT ACACAGTTGC    3420
CTATAAAAAG TCTATGTTAT CCAAGCAATT CACTCTAGAA GCTTCGGTCT CGTTGTTGTA    3480
```

-continued

| | | | | | | |
|---|---|---|---|---|---|---|
| TGCAATTTTT | ACTATCATGC | AAATAAGCTT | AGGTAAATAA | AACTAATAGA | TCACCTTAGA | 3540 |
| AAATTATGCA | ATTAATGTGA | AAATAATTGA | TGTTTGCAAT | GTGTCTTCCT | TTGGTTTACA | 3600 |
| ATCAATTTTA | AAGCGACATC | TGTATAAAGT | TTCTGTATAA | AGGTGTATTT | CTTTTTTATG | 3660 |
| AGTTTATGGC | TATGAAAACA | CCAGCTATTT | TGTTACAGGG | GTACCGAGCT | CAGTGTATCA | 3720 |
| CAGTTTTCTT | TATGCAGAAA | TGTGCTGATT | AGGAGTGGTT | ATTGACTGTA | AGTACACGAT | 3780 |
| TAAAATTGTT | TGTATGGTAA | AAAAAAAAA | AAAAAAAA | | | 3819 |

(2) INFORMATION FOR SEQ ID NO:4:

(i) SEQUENCE CHARACTERISTICS:
        (A) LENGTH: 1183 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Mouse
        (B) STRAIN: AKR1 Jackson
        (C) INDIVIDUAL ISOLATE: SL12 cell line
        (F) TISSUE TYPE: Lymphoma
        (G) CELL TYPE: T-cell
        (H) CELL LINE: SL12.3 and SL12.4

(vii) IMMEDIATE SOURCE:
        (B) CLONE: 19.5

(xi) SEQUENCE DESCRIPTION: SEQ ID NO:4:

| | | | | | | |
|---|---|---|---|---|---|---|
| CCTAACTGAC | AAAGTGGGGA | GAGTAAGGTG | TGCGCAAACA | GGACAAGTTG | GGTCATGGGG | 60 |
| AGTTTCAAAG | GACATGCTCT | CCCTGGGAGT | TTCTTCTTCG | CCATGGGCTT | TTGGTGGACT | 120 |
| ATGAAGAACA | TCCTGAAATC | TGTCTACAAA | AGGCAAACTC | GAACCTGCTA | CCTTAACTCT | 180 |
| AAAACATTAT | TACGTCGGAC | AGAGATTTGG | GAAGGAGTTG | TTGTGCTTTT | AATGTCTCTC | 240 |
| ACTGGTATAG | CTGGTGAACA | GTTTATCTCA | GGAGGACCTG | CCTTGATCTT | GCATAAAGAT | 300 |
| GGCCAGTGGA | ACCAGATCCT | GGGCTGGCAT | CACACAACCA | TGTACTATT | CTTTGGGCTA | 360 |
| CAGGGTATAA | CCCAAATCAT | ATGTTTCACT | ACTAATGTAC | TTCCACTTTC | CTCAAGCAAG | 420 |
| TTAATGTTAT | CAATTGCCAT | CTTTGTGGAG | ACATTTATGT | TCTACAACCA | CACACGGT | 480 |
| CGGGAAATGA | TTGACATTTT | TGTACACCAA | CTTCTGGTCT | TCGTTGGCAC | ATTTTCGGGT | 540 |
| CTGGTTGCCT | TCTTGGAGTT | CCTCGTAAAG | AACAACGCAC | TTCTGGAGCT | CCTGCGGTGC | 600 |
| AGTCTCCTCA | TGTTTCAAGG | AACCTGGTTC | TGGCAGATGG | CGTTTGTGCT | GTACCCCCA | 660 |
| TGTGGAAGTG | CTACATGGAA | CCTGTCAGAT | ATTCAAAATA | AATGTTTCT | CTCAATGTGC | 720 |
| TTTTGCTGGC | ATTATGCATC | AATCCTTATC | CTCATTGGAG | TAAAATATGC | TTTGGCCAAC | 780 |
| TGGTTAGTCA | AGTCTAGGCT | GAGGAAGGGC | TGCACCTCAG | AAGTTGGACT | CCTGAAGCAT | 840 |
| GCTGACCGTG | AGCAAGAATC | AGAAGAAGAA | GTATGATCTT | GAAGTCTTTC | TTGATAAGCC | 900 |
| TTCTCCCTTT | GCGTTGCCTT | TGTTCATGGC | TTTGTTTCCT | GACCTCTGGT | CTCAAGAACA | 960 |
| CTTGTCTGAG | GCTGACTCCA | TGCTGTTTGT | ACTTCCAGTT | TTGTTAAAGT | GTTGGACTTT | 1020 |
| AAGTATCTTA | CTTTCAGCTC | TGAAAGAACC | ATGAGTGATA | AATTCACTTT | TTACACTGTG | 1080 |
| CATGCCATGT | AATTCAAGAC | CAATCATAAT | TGTTTTCCAA | AGTTTAGTTT | CGTGTCCATT | 1140 |
| TATTAAAAAT | ATTTTTTTTT | ATTTTCCGGG | TAGATACCTT | CAA | | 1183 |

(2) INFORMATION FOR SEQ ID NO:5:

(i) SEQUENCE CHARACTERISTICS:
        (A) LENGTH: 2397 base pairs (B) TYPE: nucleic acid
(C) STRANDEDNESS: double
(D) TOPOLOGY: linear (ii) MOLECULE TYPE: cDNA to mRNA (v) ORIGINAL SOURCE:
(A) ORGANISM: Mouse
(B) STRAIN: AKR1 Jackson
(C) INDIVIDUAL ISOLATE: SL12 cell line
(F) TISSUE TYPE: Lymphoma
(G) CELL TYPE: T-cell
(H) CELL LINE: SL12.3 and SL12.4

(vii) IMMEDIATE SOURCE:
(B) CLONE: 20.5

(xi) SEQUENCE DESCRIPTION: SEQ ID NO:5:

| | | | | | |
|---|---|---|---|---|---|
| GGGTGTCTTT | CCTCATCGCT | GCCCTGGCCT | CGGTTATGGC | CGGCCTTTGC | TATGCTGAAT | 60 |
| TTGGGGCCCG | AGTACCCAAG | ACTGGATCTG | CGTATCTATA | CACTTACGTC | ACGGTCGGAG | 120 |
| AGCTGTGGGC | CTTCATCACT | GGCTGGAATC | TCATCCTGTC | ATATGTCATA | GGTACGTCCA | 180 |
| GTGTCGCAAG | AGCATGGAGT | GGCACCTTTG | ACGAACTTCT | TAATAAACAG | ATTGGCCAGT | 240 |
| TTTTCAAAAC | GTACTTCAAA | ATGAATTACA | CTGGTCTGGC | AGAGTATCCA | GACTTCTTTG | 300 |
| CCGTGTGCCT | TGTATTACTC | CTGGCAGGTC | TTTTATCTTT | TGGAGTAAAA | GAGTCTGCTT | 360 |
| GGGTGAATAA | ATTTTTACAG | CTATTAATAT | CCTGGTCCTT | CTCTTTGTCA | TGGTGGCTGG | 420 |
| GTTTGTGAAA | GGAAATGTGG | CTAACTGGAA | GATCAGTGAA | GAGTTTCTCA | AAAATATATC | 480 |
| AGCAAGTGCT | AGAGAACCAC | CTTCTGAGAA | CGGAACAAGC | ATCTACGGGG | CTGGCGGCTT | 540 |
| TATGCCCTAT | GGCTTTACAG | GGACGTTGGC | TGGTGCTGCA | ACGTGCTTTT | ATGCCTTTGT | 600 |
| GGGCTTTGAC | TGCATTGCAA | CAACCGGTGA | AGAGGTTCGG | AATCCACAAA | AGGCGATCCC | 660 |
| CATCGGAATA | GTGACGTCCT | TACTTGTCTG | CTTTATGGCT | TACTTTGGGG | TTTCTGCAGC | 720 |
| TTTAACGCTT | ATGATGCCTT | ACTACCTCCT | GGATGAGAAA | AGTCCACTCC | AGTCGCGTT | 780 |
| TGAGTATGTC | AGATGGGGCC | CCGCCAAATA | CGTTGTCGCA | GCAGGCTCCC | TCTGCGCCTT | 840 |
| ATCAACAAGT | CTTCTTGGAT | CCATTTCCC | AATGCCTCGT | GTAATCTATG | CTATGGCGGA | 900 |
| GGATGGGTTG | CTTTTCAAAT | GTCTAGCTCA | AATCAATTCC | AAAACGAAGA | CACCAGTAAT | 960 |
| TGCTACTTTG | TCATCGGGTG | CAGTGGCAGC | TGTGATGGCC | TTTCTTTTTG | ACCTGAAGGC | 1020 |
| CCTCGTGGAC | ATGATGTCTA | TTGGCACCCT | CATGGCCTAC | TCTCTGGTGG | CAGCCTGTGT | 1080 |
| GCTTATTCTC | AGGTACCAAC | CTGGCTTGTG | TTACGAGCAG | CCCAAATACA | CCCCTGAGAA | 1140 |
| AGAAACTCTG | GAATCATGTA | CCAATGCGAC | TTTGAAGAGC | GAGTCCCAGG | TCACCATGCT | 1200 |
| GCAAGGACAG | GGTTTCAGCC | TACGAACCCT | CTTCAGCCCC | TCTGCCCTGC | CACACGACA | 1260 |
| GTCGGCTTCC | CTTGTGAGCT | TTCTGGTGGG | ATTCCTGGCT | TCCTCATCC | TGGGCTTGAG | 1320 |
| TATTCTAACC | ACGTATGGCG | TCCAGGCCAT | TGCCAGACTG | GAAGCCTGGA | GCCTGGCTCT | 1380 |
| TCTCGCCCTG | TTCCTTGTCC | TCTGCGCTGC | CGTCATTCTG | ACCATTTGGA | GGCAGCCACA | 1440 |
| GAATCAGCAA | AAAGTAGCCT | TCATGGTCCC | GTTCTTACCG | TTTCTGCCGG | CCTTCAGCAT | 1500 |
| CCTGGTCAAC | ATTTACTTGA | TGGTCCAGTT | AAGTGCGGAC | ACTTGGATCA | GATTCAGCAT | 1560 |
| CTGGATGGCG | CTTGGCTTTC | TGATCTATTT | CGCCTATGGC | ATTAGACACA | GCTTGGAGGG | 1620 |
| TAACCCCAGG | GACGAAGAAG | ACGATGAGGA | TGCCTTTTCA | GAAAACATCA | ATGTAGCAAC | 1680 |
| AGAAGAAAAG | TCCGTCATGC | AAGCAAATGA | CCATCACCAA | GAAACCTCA | GCTTACCTTT | 1740 |
| CATACTTCAT | GAAAAGACAA | GTGAATGTTG | ATGCTGGCCC | TCGGTCTTAC | CACGCATACC | 1800 |
| TTAACAATGA | GTACACTGTG | GCCGGATGCC | ACCATCGTGC | TGGGCTGTCG | TGGGTCTGCT | 1860 |
| GTGGACATGG | CTTGCCTAAC | TTGTACTTCC | TCCTCCAGAC | AGCTTCTCTT | CAGATGGTGG | 1920 |

| | | | | | | |
|---|---|---|---|---|---|---|
| ATTCTGTGTC | TGAGGAGACT | GCCTGAGAGC | ACTCCTCAGC | TATATGTATC | CCCAAAACAG | 1980 |
| TATGTCCGTG | TGCGTACATG | TATGTCTGCG | ATGTGAGTGT | TCAATGTTGT | CCGTTATTAG | 2040 |
| TCTGTGACAT | AATTCCAGCA | TGGTAATTGG | TGGCATATAC | TGCACACACT | AGTAAACAGT | 2100 |
| ATATTGCTGA | ATAGAGATGT | ATTCTGTATA | TGTCCTAGGT | GGCTGGGGAA | ATAGTGGTGG | 2160 |
| TTTCTTTATT | AGGTATATGA | CCATCAGTTT | GGACATACTG | AAATGCCATC | CCCTGTCAGG | 2220 |
| ATGTTTAACA | GTGGTCATGG | GTGGGGAAGG | GATAAGGAAT | GGGCATTGTC | TATAAATTGT | 2280 |
| AATGCATATA | TCCTTCTCCT | ACTTGCTAAG | ACAGCTTTCT | TAAACGGCCA | GGGAGAGTGT | 2340 |
| TTCTTTCCTC | TGTATGACAA | GATGAAGAGG | TAGTCTGTGG | CTGGAGATGG | CCAATCC | 2397 |

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Lys  Gly  His  Ala  Asp  Arg  Glu  Gln  Glu  Ser  Glu  Glu  Glu  Val
    1                 5                              10

T-CELL LYMPHOMA CDNA CLONES

This is a division of application Ser. No. 07/686,322, filed Apr. 11, 1991 now U.S. Pat. No. 5,312,733, Jan. 20, 1995 which is a continuation of Ser. No. 07/509,684 filed Apr. 13, 1990, now abandoned.

FIELD OF THE INVENTION

This invention relates to novel DNA sequences, recombinant DNA molecules, processes for producing novel transmembrane proteins expressed in T-cell development and the novel transmembrane proteins in substantially pure form. More particularly, it relates to novel DNA sequences expressed in appropriate hosts and the novel proteins two of which are integral membrane proteins produced in these hosts. The DNA sequences and recombinant DNA molecules of this invention are characterized in that each codes for a novel protein having at least two of the following characteristics: (1) is expressed by T lymphoma cells, (2) is expressed in normal thymus, activated spleen cells, or gut associated lymphoid tissue, (3) is expressed in ovarian tissue, normal liver or immortalized or cancerous cell lines, (4) is expressed in embryonic development and/or (5) having multiple membrane spanning domains. As may be appreciated from the disclosure to follow, the DNA sequences, recombinant DNA molecules and processes for producing novel proteins expressed in T-cell development and the novel T-cell proteins in substantially pure form may be useful in manipulating the regulation of T cell development, altering the tumorigenic phenotype and may also be useful for localizing metastatic foci of tumors. This invention also provides novel antibodies which bind to epitopes on the proteins of the present invention and use of these antibodies to identify and target drugs or other agents to specific cell types expressing the novel proteins.

BACKGROUND ART

In the development of the immune system, T lymphocytes are derived from precursor stem cells which enter the thymus to undergo differentiation and maturation. Many genes are either activated or repressed as the T cell passes through different stages of development within the thymus. For example, the cells acquire the IL-2 receptor, CD4, and/or CD8 on their surface during this time. These differentiation markers are important for T cell development and/or function. Many gene products are increased in their levels of expression in developing T lymphocytes. These include the T cell receptor for antigen as well as the markers CD4 and CD8. Many other antigens have served as T cell markers before their exact function in lymphocytes were known. Only recently has it been discovered that the T cell antigen Pgpl aids thymocytes in their homing to the thymus whereas T200 (CD45) serves as a component for intracellular signalling. Another T cell marker, Thy1, still has no known function associated with it.

The SL 12.4 cells exhibit a CD4 CDB double negative phenotype and therefore resemble thymocytes at a relatively early stage of development. Furthermore, they do not express the T cell receptor alpha subunit. SL 12.4 cells, however, can be induced to stably express CD4 and CD8 on their surface after co-cultivation upon thymic epithelial monolayers. TCR-alpha mRNA is also induced after these treatments. Thus, it appears that SL 12.4 cells have the capacity to undergo differentiation and maturation. This unique in vitro biological system mimics, to some extent, the thymic microenvironment.

A number of genes have been identified which are first expressed in developing thymocytes. Many of these genes encode proteins which must be expressed for T cell precursors to become functional in the immune system, for example: 1) the TCR for antigen which is required for antigen recognition; 2) CD25 (the IL2 receptor) which must be expressed for the cells to respond to the cytokine IL2; 3) gene products important for signal transduction during antigen recognition, such as CD3, CD4, CDS, CD45, 4) some of the gene products involved in thymocyte homing to target organs, and 5) gene products involved in T cell activation (Fowlkes and Pardoll, *Advances in Immunology* 44:207-264 (1989); Hood et al., (1985) *Cell* 40, 225-229; Rothenberg and Lugo, *Develop. Biol.* 112, 1-17 (1985); Adkins et al., *Ann. Rev. Immunol.* 5:325-365 (1987); Crabtree, *Science* 243:343-355 (1989); Kwon and Weissman, *Proc. Natl. Acad. Sci. USA* 86:1963-1967 (1989). There is remarkable heterogeneity in thymocyte subsets which express different combinations of expressed genes. Gene expression has been analyzed in detail in many, but not all, of the numerous classes of thymocytes and it is likely that genes remain to be identified that encode products which function in T cell development and homing; particularly those which are expressed in numerically infrequent, transient progenitor thymocytes.

Due to the extensive heterogeneity of thymocytes, it is not feasible to obtain fractionated progenitor thymocytes in sufficient numbers or purity to fully characterize the cascade of gene expression which occurs during development. For this reason, lymphoma and leukemia cell lines have been used extensively to study gene expression in lymphoid development (Greaves, *Science* 234:697-704 (1986); Hanley-Hyde and Lynch *Ann. Rev. Immunol.* 4:621-649 (1986). A considerable body of literature indicates that numerically infrequent, transient progenitor cells are the target of transformation to malignancy; and further that some of the characteristics of the transformed target cells are preserved in the tumor cells. Unexpected gene expression in tumor cells was frequently dismissed as an aberration of transformation. However, careful analysis of "aberrant" gene expression in hematopoietic tumor cells, has revealed rare subsets of normal progenitor cells which express such genes (Greaves, *Science* 234:697-704 (1986); Hanley-Hyde and Lynch *Ann. Rev. Immunol.* 4:621-649 (1986); Pierce and Speers *Cancer Res.* 48:1996-2004 (1988).

The heterogeneity of murine and human lymphoma cell lines derived from a single individual can result from differences in the extent of maturation reached by individual cells. The heterogeneity of established T lymphoma cell lines has been utilized to obtain closely related cell clones which differ in a limited number of characteristics. Hedrick, et al (Hedrick, et al., *Nature* 308:149-153 (1984), using subtraction cloning techniques, provided estimates that T and B, cells differ in the expression of about 100 genes. It is likely that closely related T lymphoma cells might differ in the expression of even fewer genes. Such cell clones provide an opportunity to work with pure populations of cells with defined and stable phenotypes which differ in a limited number of characteristics. The SL12 T lymphoma model system was developed and utilized in the present application to provide such a closely related cell population. (Hays et al., *Int. J. Cancer* 30:597–601 (1986); MacLeod, et al., *Cancer Research* 44:1784–1790 (1984); MacLeod, et al., *J. Nat. Cancer Inst* 74:875–882 (1985); MacLeod, et al., *Proc. Natl. Acad,.Sci. USA* 83:6989–6993 (1986); Siegal, et al., *J. Exp. Med.* 166:1702–1715 (1987).

BRIEF DESCRIPTION OF THE INVENTION

The present invention provides novel DNA sequences, recombinant DNA (rDNA) molecules, processes for producing novel T-cell proteins expressed in T-cell development, the novel T-cell proteins in substantially pure form and antibodies which bind to the novel proteins. More particularly, it relates to novel DNA sequences expressed in appropriate hosts and the novel T-cell proteins produced in these hosts. The present invention also provides novel transmembrane proteins in substantially pure form, rDNA molecules encoding said transmembrane proteins and processes for producing the novel transmembrane proteins. The DNA sequences and recombinant DNA molecules of this invention are characterized in that they are expressed by T lymphoma cells and have at least one of the following characteristics: (1) is expressed in normal thymus, activated spleen cells, or gut associated lymphoid tissue, (2) is expressed in ovarian tissue, normal liver and/or in a stage specific manner in embryonic development and (3) encode novel transmembrane proteins having multiple membrane spanning domains.

In another aspect, the present invention provides a novel gene, 19.5 also referred to herein as Lov, inducible in SL 12.4 cells after co-cultivation on thymic epithelial monolayers. The present invention also provides polyclonal antibodies raised against an oligopeptide construct based on the Lov cDNA sequence. The induction of Lov appears to be stable since cell clones isolated from an SL 12.4 cell population after co-cultivation exhibit a higher level of Lov expression at the mRNA as well as at the surface protein level. The Lov gene has been mapped to murine Chromosome 16. The Lov gene product is developmentally regulated and plays a role in T cell development.

An SL 12.4 cDNA library has been constructed from which six novel cDNAs were isolated via subtractive hybridization against a related sister lymphoma cell line, SL 12.3. SL 12.3 cells have characteristics of thymocytes at a more immature stage of development than SL 12.4. One of the cDNA clones, 19.5, is expressed in SL 12.4, but is absent in SL 12.3 cells. This sequence has been named Lov (lymphoid and ovarian cellular expression). The predicted protein appears to be highly hydrophobic and based on computer analysis, it contains four transmembrane spanning regions. No significant homologies have been found between the Lov cDNA nor the predicted protein sequence with other known sequences. Lov is conserved among mammalian species, such as, for instance, human, rodent, rabbit, sea lion, and birds, and the transcript appears to be highly expressed in ovaries and gut associated lymphoid tissue (GALT), as well as in the thymus. Lov expression and its inducibility in the biosystem, the physical characteristics of the Lov protein, as well as the murine chromosomal localization of this gene are disclosed herein.

By providing the DNA sequences, and recombinant DNA molecules, the present invention also provides probes and methods to identify cells containing or lacking these sequences, and means to administer these sequences to cells lacking these sequences. Additionally, the present invention provides a means to inhibit the expression of the novel sequences by providing an antisense RNA sequence which, when administered to a cell, or when the DNA encoding said antisense RNA is administered to a cell containing said DNA sequence will produce an antisense RNA which can bind to and therefore block the synthesis of the RNA encoding the novel proteins of the present invention. It will also be apparent to one of skill in the art from this disclosure that antibodies against any of the proteins of the present invention can be utilized to block the binding of ligands to the proteins and to target drugs or other agents (such as labels) to the cells expressing these proteins.

Also provided is a cDNA clone, 20.5 also referred to herein as Tea, which identifies transcripts found in only a limited number of tissues. Tea transcripts are induced in splenocytes activated with the T cell mitogen ConA. Unlike other known gene expressed in activated T cells, the Tea gene appears to encode a protein which traverses the membrane multiple times, whereas the large number of known integral membrane proteins which are induced in T cell activation are single membrane spanning proteins (Crabtree, (1989) *Science* 243: 355–361).

The present invention also provides processes for producing novel transmembrane proteins and the novel transmembrane proteins in substantially pure form which may be useful in the regulation of T cell development, regulation of tumorigenic phenotype and may also be useful for blocking the activation of T cells in autoimmune disease.

Novel cDNA clones which are differentially expressed between two closely related T lymphoma cell clones were isolated using subtraction-enriched differential screening. SL12.4 cells, from which the cDNAs were isolated, have characteristics of thymocytes at an intermediate stage in development and cause prominent extranodal ovarian tumors in syngeneic animals. A sister cell clone, SL12.3, derived from the same tumor has a distinct phenotype and causes more aggressive, diffuse lymphomas. Four of the five novel genes are expressed in normal thymus, activated spleen cells or gut associated lymphoid tissue. The DNA sequences and predicted protein sequences for the novel cDNA clones are presented on FIGS. 3–5, 19 and 36–39. The novel 19.5 cDNA clone detects mRNA in normal thymus, gut associated lymphoid tissue and ovarian tissue. The predicted protein has four putative transmembrane spanning regions. The expression of the transcript is repressed in somatic Cell hybrids formed fromSL12.4 cells fused with three different T lymphoma cell lines which lack detectable mRNA complementary to the novel cDNA clone. This trans-negative regulation suggests that the expression of the gene is regulated by repressional mechanisms.

BRIEF DESCRIPTION OF THE DRAWINGS

FIG. 3 demonstrates DNA and predicted protein sequence of the 19.5 cDNA clone.

FIG. 4 shows a schematic of the predicted protein from the 19.5 cDNA clone based on a computer analysis of its physical properties.

FIG. 5 shows the restriction sites within the cDNA for subcloning and the sequencing strategy.

FIG. 8 demonstrates by Northern Blot sequences complementary to 19.5 cDNA are contained in human ovarian carcinoma cell lines.

FIG. 9 demonstrates by Southern Blot that the sequences complementary to 19.5 are present in a variety of mammalian species and are thus conserved in evolution.

FIG. 10 demonstrates by Northern Blot that both transcripts of Lov are induced in response to co-cultivation.

FIG. 14 demonstrates the specificity of the 19.5 antibody for the immunizing antigen but not by an irrelevant oligopeptide.

FIG. 15 demonstrates the inducibility of Lov protein by thymic epithelial cells.

FIG. 19 demonstrates the DNA and predicted protein sequence of clone 20.5 cDNA.

FIG. 26 demonstrates the alignment of 20.5 and ERR cDNA sequences.

FIG. 27 demonstrates the sequence alignment between 20.5 cDNA (top) and ERR eDNA (bottom).

FIG. 29 demonstrates the alignment of Tea predicted protein sequence with the murine ecotropic retroviral receptor sequence.

FIG. 36 demonstrates the DNA and predicted protein sequence of clone 19.1 cDNA.

FIG. 37 demonstrates the DNA and predicted protein sequence of clone 19.2 cDNA.

FIG. 38 demonstrates the DNA and predicted protein sequence of clone 19.4 cDNA.

DETAILED DESCRIPTION OF THE INVENTION

Figure 1:
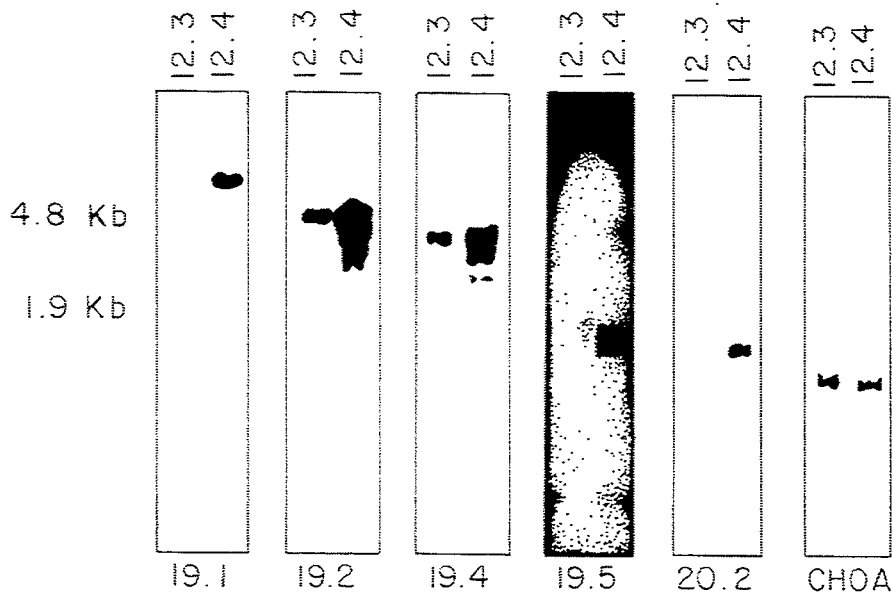
FIG. 1 demonstrates the expression of 5 different SL12.4-specific cDNA clones by Northern Blot.

In order that the invention herein described may be more fully understood, the following detailed description is set forth.

In the description the following terms are employed:

The term "host" as used herein is meant to include not only prokaryotes but also eukaryotes such as yeast and filamentous as well as plant and animal cells.

The term "prokaryote" is meant to include all bacteria which can be transformed with the DNA for the expression of the transmembrane or recombinant transmembrane T cell proteins (rtTCP) of the present invention.

The term "eukaryote" is meant to include all yeasts, fungi, animal and plant cells which can be transformed with the DNA for the expression of the transmembrane or recombinant transmembrane T cell proteins of the present invention.

The DNA for the T cell proteins of the present invention can be derived from any mammalian species. All that is required is that the genetic sequence for the T cell proteins (TCP) be expressed in the prokaryotic or eukaryotic organism. Preferred is the T cell DNA which expresses TCP protein(s) from mice. Especially preferred is the sequence of the T cell DNA which is immunologically cross reactive among multiple animal species (e.g., mice, rabbit, sea lion or human).

A recombinant DNA molecule coding for any of the T cell proteins of the present invention can be used to transform a host using any of the techniques commonly known to those of ordinary skill in the art. Especially preferred is the use of a vector containing coding sequence for the T cell proteins of the present invention for purposes of prokaryote transformation.

The T cell recombinant protein (rTCP) of the invention could have more or less amino acids at its flanking ends as compared to the amino acid sequence of native T cell proteins.

The term "substantially pure" when applied to the transmembrane T cell protein of the present invention means that the polypeptide is essentially free of other proteins normally associated with the T cell protein in its natural state and exhibiting constant and reproducible electrophoretic or chromatographic response, elution profiles, and antigen activity. The term "substantially pure" is not meant to exclude artificial or synthetic mixtures of the T cell protein with other compounds.

Methods for preparing fused, operably linked genes and expressing them in bacteria are known and are shown, for example, in U.S. Pat. No. 4,366,246, herein incorporated by reference. The genetic constructs and methods described therein can be utilized for expression of transmembrane T cell protein in prokaryotic or eukaryotic hosts.

Prokaryotic hosts may include Gram negative as well as Gram positive bacteria, such as *E. coli, S. tymphimurium, Serratia marcescens,* and *Bacillus subtilis.*

Eukaryotic hosts may include yeasts such as *Pichia pastoris* or mammalian cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Examples of promoters which can be used in the invention include, but are not limited to: rec A, trp, lac, tac, bacteriophage lambda pR or pL, MMTV, SV40. Examples of some of the plasmids or bacteriophage which can be used in the invention are listed in Maniatis et al., *Molecular Cloning,* Cold Spring Harbor Laboratories, 1982, and others are known to those of skill in the art and can be easily ascertained.

The invention extends to any host modified according to the methods described, or modified by any other methods, commonly known to those of ordinary skill in the art, such as, for example, by transfer of genetic material using a lysogenic phage, and which yield a prokaryote or eukaryote expressing the gene for transmembrane T cell protein.

A gene is a DNA sequence which encodes through its template or messenger RNA a sequence of amino acids characteristic of a specific peptide. The term cDNA includes genes from which the intervening sequences have been removed. By the term rDNA is meant a molecule that has been recombined by splicing cDNA or genomic DNA sequences in vitro.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance, neomycin resistance or ampicillin resistance. The word "vector" is sometimes used for cloning vehicle.

An expression vehicle is a vehicle similar to a cloning vehicle but which is capable of expressing a given structural gene in a host, normally under control of certain control sequences.

Hosts transformed with the transmembrane T cell genome for transmembrane T cell proteins are particularly useful for the production of transmembrane T cell polypeptide and protein.

The recombinant T cell protein may comprise the entire amino acid sequence of the T cell protein or may comprise only a specific determinant. An animal immunized with T cell recombinant protein will produce antibodies which will bind to epitopes present on the recombinant or naturally occurring polypeptides. Thus, the commercial production of T cell-containing recombinant proteins can be carried out.

The term "individual" is meant to include any animal, preferably a mammal, and most preferably a rodent, cat, dog, cow or human.

Detectable labels may be any molecule which may be detected. Commonly used detectable labels are radioactive labels including, but not limited to, $^{32}P$, $^{14}C$, $^{125}I$, $^{3}H$ and $^{35}S$. Biotin labeled nucleotides can be incorporated into DNA or RNA by nick translation, enzymatic, or chemical means. The biotinylated probes are detected after hybridization using avidin/streptavidin, fluorescent, enzymatic or collodial gold conjugates. Nucleic acids may also be labeled with other fluorescent compounds, with immunodetectable fluorescent derivatives or with biotin analogues. Nucleic acids may also be labeled by means of attaching a protein. Nucleic acids cross-linked to radioactive or fluorescent histone HI, enzymes (alkaline phosphatase and peroxidases), or single-stranded binding (ssB) protein may also be used.

Thus, the present invention makes available an antitransmembrane T cell protein antibody for use as a probe for the transmembrane proteins of the present invention and as inhibitors of binding of the natural ligands of the transmembrane T cell proteins of the present invention and as a drug or label targeting delivery system.

Two cell clones derived from the SL12 T lymphoma cell line were chosen for the isolation of novel differentially expressed genes based on known differences in gene expression and on their different capacity to cause tumors in syngeneic host animals (Hays, et al., *Int. J. Cancer* 38:597–601 (1986); MacLeod, et al., *Cancer Research* 44:1784–1790 (1984); MacLeod, et al., *J .Nat. Cancer Inst.* 74:875–882 (1985); MacLeod, et al., *Proc. Natl. Acad. Sci. USA* 83:6989–6993 (1986); Siegal, et al., *J. Exp. Med.* 166:1702–1715 (1987); Weinroth, et al., *Cancer Research* 45:4804–4809 (1985); Wilkinson, et al., *EMBO J.* 7:101–109 (1988) and Table 1 for a summary of phenotypes). The SL12.3 cell line expresses very few of the genes required for T cell function, it is highly malignant in syngeneic animals and forms diffuse, aggressive tumors. In contrast, SL12.4 cells express mRNAs for all the components of the TCR/CD3 complex except TCR-alpha, and in several respects, the cells are similar to thymocytes at an intermediate stage in thymocyte development. SL12.4 cells are much less tumorigenic and induce prominant extranodal tumors. In female host animals, the primary site of tumor formation is the ovary. The novel transmembrane proteins may be involved in targeting the tumor cells to the ovary.

Novel cDNA clones were isolated from the two cell lines differing in tumorigenic capacity, homing properties and maturational state. These cDNA clones represent genes which encode products related to the different capacity of the two cell lines to cause tumors and/or those which function in T cell development. This invention discloses the isolation and characterization of five novel cDNA clones representing genes which are preferentially expressed in the SL12.4 T cell clone, and are undetectably or weakly expressed in a sister cell clone, SL12.3. The cDNA clones were obtained by a combination of subtraction hybridization enriched probes and classical differential screening. Novel cDNA clones which represent genes differentially expressed between the two cell clones are disclosed. All of the respective genes are expressed in a limited subset of tissues. Some transcripts are not exclusively found in lymphoid cells, but show an array of expression. The sequences of two of the cDNAs (19.5 and 20.5) indicate that the gene products are novel multiple membrane spanning proteins which are expressed in normal murine ovary tissue, thymus, gut associated lymphoid tissue, spleen and liver. One sequence also hybridized with human ovarian carcinoma cells and normal tissue.

Having now generally described the invention, a more complete understanding can be obtained by reference to the following specific examples. These examples are provided for purposes of illustration only and are not intended to be limiting unless otherwise specified.

EXAMPLE 1

Isolation, Characterization and Culture of Cells

A. Lymphoma Cell Lines

The isolation, characterization and culture requirements of the T lymphoma cell lines SL12.1, SL12.3, SL12.4 and somatic cell hybrids formed among them have been described in detail in Hays, et al., *Int. J. Cancer* 38:597-601 (1986); MacLeod, et al., *Cancer Research* 44:1784-1790 (1984); MacLeod, et al., *J. Nat. Cancer Inst* 74:875-882 (1985); MacLeod, et al., *Proc. Natl. Acad. Sci. USA* 83:6989-6993 (1986) and Weinroth, et al., *Cancer Research* 45:4804-4809 (1985); all of which are incorporated herein by reference.

The phenotypes of the SL12.3 and SL12.4 cell clones are summarized in Table 1. Transcript expression, surface protein expression, tumorigenicity and tumor type were determined by Northern analysis, flow cytometry and in vivo injection of cloned cells into syngeneic animals, respectively. TCR-$\beta$ 1.0 and 1.3 kb transcripts encode (D)-J-C and V-D-J-C sequences, respectively. The glucocorticoid response was determined by growth of the cells in 1 mM dexamethasone.

TABLE 1

| Phenotypic Characteristics of SL12.4 and SL12.3 Cell clones | | | |
|---|---|---|---|
| | | SL12.4 | SL12.3 |
| mRNA | Thy-1 | ++ | +++ |
| | TCR-alpha | − | + |
| | TCR-$\beta$ | | |
| | 1.0 kb | + | − |
| | 1.3 kb | − | − |
| | TCR-gamma | − | − |
| | TCR-delta | − | − |
| | CD3-gamma | + | − |
| | CD3-delta | + | − |
| | CD3-epsilon | + | +/− |
| | CD3-zeta | + | + |
| | CD2 | + | + |
| | CD4 | − | − |
| | CD8 | − | − |
| Surface Expression | Thy-1 | ++ | ++ |
| | Pgp-1 | − | + |
| | ThB | + | − |
| | TL | + | + |
| | T200 | + | + |
| | H-2K$^k$ | − | − |
| | IL2r | + | + |
| | J11d | + | + |
| | CD3-epsilon | − | − |
| | Mel-14 | + | NT |
| Glucocorticoid Sensitivity | | | SR |
| Tumorigenicity | | | LowHigh |
| Tumor Type | | Extra-Nodal | Diffuse |

R = cells resistant to lysis; S = sensitive to lysis; NT = not tested.

SAK8 cells (Gasson and Bourgeois, *J. Cell. Biol.* 96, 409-415 (1983) were obtained from Dr. Gasson. The lymphoma cells were cultured in Dulbecco's Modified Eagle's Medium supplemented with 10% fetal calf serum, glutamine, penicillin and streptomycin. Two human ovarian carcinoma cell lines 2008 (Disaea, et al., *Am. J. Obstet. Gynecol.* 114:979-989 (1972)) and COLO 316 (Woods, et al., *Cancer Res.* 39:4449-4459 (1979) were cultured in RPMI medium 1640 supplemented with 5% bovine calf serum, glutamine and 1% Fungibact (Irvine Scientific, Santa Ana, Calif.). When the cells were used to prepare RNA, they were harvested during exponential growth at a density near $5-8 \times 10^5$ cells per ml (Wilkinson, and MacLeod, *EMBO J.* 7:101-109, (1988). Splenocytes derived from BALB/c mice were seeded at $3 \times 10^6$ cells/ml and stimulated with 10 ug/ml ConA for two days before harvesting the RNA.

B. Co-cultivation of SL 12.4 Cells and the Thymic Epithelial Monolayers

The co-cultivation conditions for SL 12.4 cells and the thymic epithelial monolayers. Briefly, SL 12.4 cells were seeded at a density such that their final concentration after the three day co-cultivation period was $1 \times 10^6$ cells/ml. TEL or TEPI were at confluency by the third day. The cells were grown in Dubellco's Modified Eagles Medium containing 10% fetal calf serum and supplemented with glutamine and penicillin/streptomycin at 37° C.

C. Cell Lines for 20.5 Expression Studies

Cell lines from the following sources were used in the 20.5 expression studies: Embryonal carcinomas F9 and PCC4 (Bernstine, et al., *Proc. Natl. Acad. Sci. USA.* 70:3899-3903 (1973), pituitary tumor ATt20 (Buonassisi, et al., *Proc. Natl. Acad. Sci. USA.* 48:1184-1192 (1962)), thymic epithelial TEPI (Beardsley, et al., *Proc. Natl. Acad. Sci. USA.* 80:6005-6009 (1983)), mammary epithelial (Evans, (1988) *Science* 240:889-894)12.9), 3T3 (ATCC #92) and MEF were prepared according to Freshney (Freshney, (1983) *In Culture of Animal Cells.* Alan R. Liss, Inc. pp 99-110). The cells were cultured in Dulbecco's Modified Eagle,s Medium supplemented with 10% fetal calf serum, glutamine, penicillin and streptomycin. Cells that were used to prepare RNA were harvested during exponential growth from cultures containing $5-8 \times 10^5$ cells per ml. Splenocytes obtained from BALB/c mice were seeded at $3 \times 10^6$ cells/ml in RPMI 1640 supplemented as above and stimulated with 10 ug/ml ConA for 6, 24, 48 or 72 hours before harvesting the RNA.

EXAMPLE 2

Cloning and Screening Strategy

Poly(A)+ mRNA from SL12.4 cells was used as a template to prepare double-stranded (ds) cDNA (Gubler and Hoffman, Gene 25:263-269 (1983). EcoRI linkers were added to the ds DNA which was previously methylated. Dephosphorlyated lambda gt10 arms (Stratagene) were ligated to the cDNA and packaged into lambda phage using Stratagene packaging extract according to the manufacturer's instructions (Huynh, et al., In D. Glover (ed.), *DNA Cloning Techniques: A Practical Approach.* IRL Press, Oxford, U.K. (1984).

Subtraction hybridization was performed essentially as originally described by Hedrick, et al., (*Nature* 308:149-153 (1984); Timberlake, *Dev. Biol.* 78:497-503 (1980). Single stranded cDNA was prepared from 10 mg poly(A)+ SL124 RNA using 250 mC of $^{32}$P dCTP (Amersham) in the presence of 100 ug/ml of actinomycin D and hybridized to a Rot of 1260 (mol of nucleotide per liter×sec) with 25 mg poly(A)+ RNA from SL12.3 cells in a volume of 8 ml at 68° C. for 18 hours. After hybridization, the ss cDNA was collected by chromatography through a hydroxyapatite column. From 1 ug of starting SL12.4 cDNA, approximately 120 ng (12% of the input cDNA containing $3 \times 10^7$ cpm) was recovered and used to probe two 150 mm nitrocellulose filters containing 20,000 lambda gt10 plaques per filter. The first of two duplicate filter lifts from the SL12.4 lambda gt10 library was probed with total cDNA from SL12.3 mRNA, and the second filter lift was probed with the SL12.4 subtraction enriched cDNA prepared as described above. The strategy used was similar to that used by Filmus et al. The plaque purified lambda phage clones were identified as SL12.4-specific by two screenings (using separately prepared subtracted probes), subsequently Northern analysis was used to confirm that the clone hybridized only to mRNA from SL12.4 cells and not SL12.3 cells. The cDNA inserts were removed from lambda DNA by digestion with the restriction enzymes Hind III and Bgl II, isolated in low melting point agarose (Sea Kem) and subcloned into the plasmid vector pT7/T3 (Bethesda Research Laboratory) digested with Hind III and BamHI. The inserts could not be excised from the phage with EcoRI because the EcoRI sites were damaged in all of the isolates Kuziel, et al., *Nucl. Acid Res,* 15:3181 (1987).

EXAMPLE 3

Northern Blot Analysis

A. General Procedures

Total cellular RNA was isolated from cell lines and tissues by the guanidine isothiocyanate method (Maniatis, et al., In *Molecular Cloning: A Laboratory Manual.* Cold Spring Harbor Laboratory Press, Cold Spring Harbor, N.Y. (1983), modified as described (Wilkinson, et al., *EMBO J.* 7:101–109 (1988)). For Northern analysis, 10 ug of RNA was electrophoresed in 1% agarose gels containing formaldehyde and transferred to nitrocellulose membranes (Meinkoth, Wahl, *Anal. Biochem.* 13:267–284 (1984).

Equal loading and transfer of RNA per lane was assessed by acridine orange staining (Maniatis, et al., In *Molecular Cloning: A Laboratory Manual.* Cold Spring Harbor Laboratory Press, Cold Spring Harbor, N.Y. (1983)) and by hybridization with actin, CHO-A and/or cyclophillin cDNA. Northern blots were hybridized with random primed (Amersham) $^{32}$P-labeled cDNA inserts in the presence of 10% dextran sulphate and 50% formamide for 12–18 hr at 42° C., washed stepwise with a final 30 min. wash in 0.1× SSPE, 0.1% SDS at 42° or 50° C. To remove the labeled probe, RNA blots were washed with 0.1× SSPE and 0.1% SDS at 90° C., allowed to cool to room temperature, air-dried, and stored under vacuum until hybridized again.

B. Northern Analysis of Lov (19.5) RNA.

The SL 12.4 cells were harvested after co-cultivation and lysed in 4M guanidinium isothiocynate, 1M 2-mercaptoethanol, and 25 mM sodium acetate (pH 5.2). The lysate was then placed on a layer of 5.7M cesium chloride/2 mM EDTA and centrifuged at 38000 RPM for 18 hours at 4° C. The RNA pellet was then resuspended in TE buffer and extracted twice with chloroform/butanol. 10 ug of RNA was electrophoresed in each lane of a 1% formaldehyde agarose gel and transferred onto nitrocellulose membranes. The Northern blots were hybridized with the cDNA insert of the Lov gene which had been labelled with $^{32}$P using the random prime labelling kit from Amersham. Hybridization was allowed to proceed for 12–18 hours at 42° C. in the presence of 10% dextran sulfate and 50% formaldehyde. The resulting autoradiograms were then analyzed for changes in Lov RNA by scanning laser densitometry. The apparent inductions were normalized for RNA load using subsequent hybridization with actin and CHO-A which are not induced upon co-cultivation (MacLeod, et al., *Proc. Natl. Acad. Sci. USA* 83:6989–6993 (1986)). The values reported therefore represent the corrected fold increase of Lov expression in co-cultivated versus untreated SL 12.4 cells.

C. Northern Blot Analysis of 20.5 (Tea) RNA

Total cellular RNA was isolated from SL12.4, SL12.3 and fresh tissue preparations from Balb/c mice by the guanidine isothiocyanate method as described above. Cytoplasmic or nuclear RNA was prepared as described above. For Northern analysis, 10 ug of RNA was electrophoresed in 1% formaldehyde agarose gels and transferred to nitrocellulose membranes (Maniatis, et al., (1983) In *Molecular Cloning: A Laboratory Manual.* Cold Spring Harbor Laboratory Press, Cold Spring Harbor, N.Y.); Meinkoth, and Wahl (1984) *Anal. Biochem.* 13:267–284.).

EXAMPLE 4

Southern Blot Analysis

A. General Procedure

Total cellular DNA was isolated from cells, T lymphoma and murine-hamster somatic cell hybrids and tissues from other species was digested with the restriction enzymes noted in the figure legends according to the supplier's conditions. Ten micro g of digested DNA was applied to each lane of a 0.7% agarose gel and electrophoresed and blotted onto Nytran supports essentially as described (Meinkoth and Wahl, *Anal. Biochem.* 12:267–284 (1984), hybridized and washed as described for Northern blot analysis.

B. Southern Blot Analysis of 20.5

Southern blot analysis of 20.5 was performed as above except as noted below.

Total cellular DNA was isolated from SL12.4 cells, murine and hamster liver and from somatic cell hybrids. DNA from chicken and human liver was obtained commercially from Clonetec, Palo Alto, Calif. The DNA was digested with the restriction enzymes noted in the Examples according to the supplier's conditions. Ten ug of digested DNA was applied to each lane of a 0.8% agarose gel and electrophoresed in Tris acetate buffer for at least 48 hr and blotted onto Nytran supports, hybridized and washed as described for Northern blot analysis. The blots containing DNA from other species was washed at a lower stringency, the final wash was carried out at romm temperature with 2× SSPE.

EXAMPLE 5

Isolation of Novel cDNA Clones Using Subtraction Enhanced-differential Screening Novel cDNA clones which are expressed exclusively or more abundantly by SL12.4 cells than in SL12.3 cells were identified and isolated as described in Examples 1–4. The initial screening of 40,000 recombinant ggt10 phage yielded only eleven candidates, eight of which were recovered following further rescreening with subtracted probes and appear to represent six different gene products. Characterization of five cDNA clones was performed. Northern blots of RNA from SL12.3 and SL12.4 cells demonstrated that the cDNA clones isolated were differentially expressed in SL12.3 and SL12.4 cells as shown on FIG. 1. Purified inserts from the respective SL12.4 T cell specific cDNA clones were labeled and used to probe Northern blots. Each lane contained 10 ug of total cellular RNA from SL12.4 and SL12.3 cell lines as indicated. The blot was probed sequentially with the indicated radioactively labeled cDNA insert. Arrows mark the relative mobility of 18S and 28S rRNA transcripts. The amount of SL12.3 and SL12.4 RNA loaded per lane was equivalent as determined by hybridization with a CHO-A cDNA probe as in Example 3.

Some of the cDNA clones were expressed exclusively in SL12.4 cells (19.5 and 20.5) whereas others (19.1, 19.2 and 19.4) were more highly expressed by SL12.4 cells. Several of the cDNAs identified more than one size class of transcript suggesting that they might initiate or terminate at different sites, be differentially spliced or they might derive from closely related genes.

Figure 2:
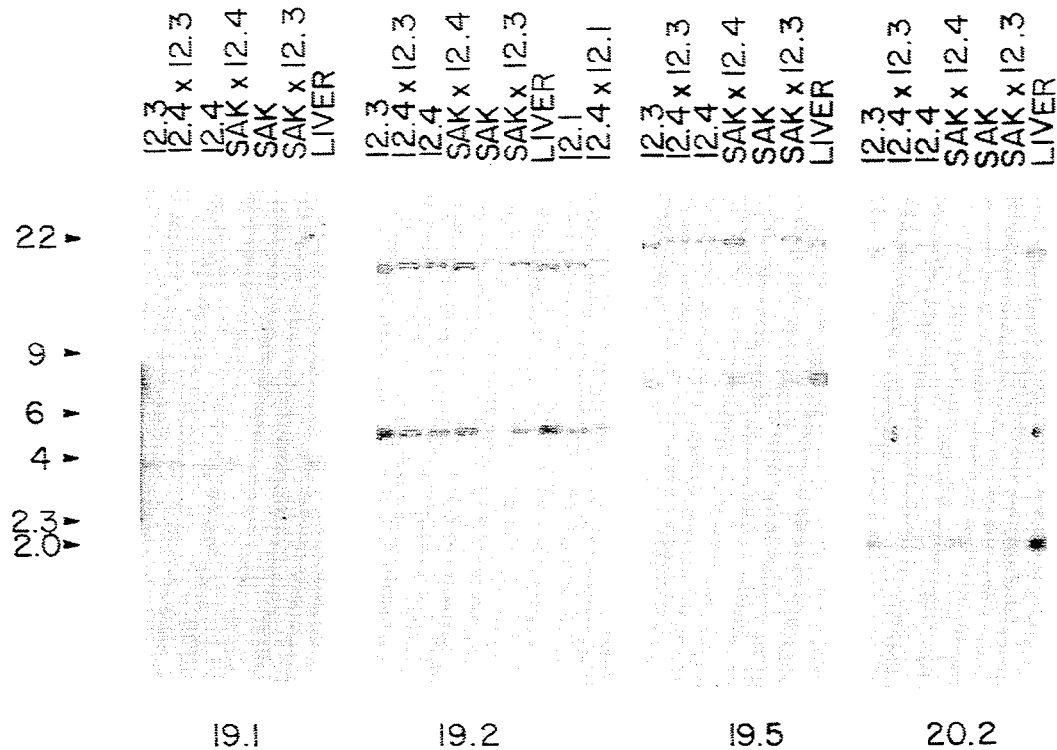
FIG. 2 demonstrates Southern blot hybridization of 4 different SL12.4 specific cDNA clones.

The cDNA clones correspond to low copy number or single copy genes present in both SL12 cell lines. Since SL12.3 cells lack detectable expression of 19.5 and 20.5 transcripts, we investigated whether the gene might have been deleted or rearranged to explain the absence of transcript. Genomic DNA from SL12.3, SL12.4 cells and normal liver DNA was digested with EcoRI, Hind III or PstI and analyzed with purified insert probes to the cDNA clones. FIG. 2 demonstrates Southern blot hybridization of SL12.4 specific cDNA clones. Genomic DNA (10 ug per lane) from AKR mouse liver, SL12.3, SL124 and SAK cloned T lymphoma cell lines and from SL12.3×SL124, SAK×SL12.4, SAK×SL12.3 hybrid cells was digested with EcoR1 and analyzed by Southern blots hybridized with the indicated cDNA clone as described in the Example 4. Fragment sizes in kilobase pairs (determined by the co-migration of lambda Hind III digested DNA) are indicated in the margin. One or a few restriction fragments were recognized by the probes indicating that the corresponding genes are present in both cell lines at low copy number in the mouse genome. The intensity of the hybridization was similar in all the lanes indicating the genes were present in the SL12.3 cell DNA in about the same amounts and without detectable rearrangements using four different enzymes (FIG. 2). Therefore, it is likely that differences in expression of the genes in the SL12 cell clones is due to cell-specific regulation and not to the loss of, or to detectable rearrangements in the respective genes. However, small rearrangements or point mutations in SL12.3 cells cannot be ruled out.

The SL12.4 specific cDNA clones represent novel genes. The 19.1, 19.2, 19.5 and 20.5 cDNAs clones have been sequenced in their entirety. There are no significant homologies with published sequences. The sequences are shown on FIGS. 3–5, 19 and 36–38.

Although the 19.4 sequence has only been partially determined (approximately 2.8 Kb[3] of 3.6 Kb), no significant sequence homology has been identified in the DNA data banks or by transcript sizes, expression levels and tissue expression patterns. Furthermore, none of the cDNA clones correspond to known T cell genes, oncogenes or murine retroviral genes known to be expressed in AKR cell lines based on transcript size or occurrence of expression (Hagiwara, et al., *J. Immunol.* 38:2514–2517. (1987); Heckford, et al., *J. Immunol.* 137:3652–3663 (1986); LeClair, et al., *EMBO J.* 5:3227–3234 (1986); Mushinski, et al., Science 220:795–798 (1983); Yague, et al., Cell 42:81–87 (1985); Quint, et al., J. Virol. 39:1–10 (1981); Selton, et al., *EMBO J.* 4:1793–1798 (1985).

The size of the cDNAs and the transcripts recognized by them, together with the length of the open reading frame (ORF[4]) are shown in Table 2.

TABLE 2

| SIZE OF cDNA INSERTS AND mRNA TRANSCRIPTS | | | | |
| --- | --- | --- | --- | --- |
| | 19.1 | 19.2 | 19.4 | 19.5 |
| cDNA Insert Size* | 1.6 | 3.2 | 3.9 | 1.2 |
| Transcript Size(s)# | 8.4 | | | |
| | 6.5 | 5.0 | 4.5 | 1.7 |
| | 4.6 | 4.5 | 4.0 | 1.5 |
| LORF+ | — | 471++ | Z2400 | 819 |

*The CDNA insert size is given as kilobase (kb) pairs and was determined from DNA sequence analysis.
The transcript sizes, in kb, were roughly estimated by their relative migration to 18S and 28S ribosomal RNA in formaldehyde agarose gels as described in Materials and Methods.
+LORF = Long open reading frame, given in base pairs. The DNA sequences were examined using Microgenie software to locate ORFS; those 1300 bp are included here. The — denotes that no long ORF was found. The 19.4 LORF of 2400 bp is preliminary, based on incomplete sequencing information.
++The 19.2 cDNA contains 2 ORFs longer than 450 bp, which may, upon re-examination, actually be contiguous and therefore comprise about 920 bp.

Based upon a comparison of transcript and cDNA insert size we conclude that none of the cDNAs are full length. The 1.6 kb DNA sequence of 19.1 cDNA does not contain any long ORFs, has a polyA tract and it is likely to represent 3' untranslated sequence. 19.2 cDNA is 3.5 Kb in length but has a relatively short ORF (471 bp[5], Table 2). The partial sequence of 19.4 cDNA reveals an ORF of 2.4 kb. Like 19,4, the 19.5 cDNA clone appears to contain the entire coding sequence, is nearly full length.

EXAMPLE 6

Analysis of 19.5 cDNA

The 19.5 cDNA clone appears to encode a multiple membrane spanning protein. The 19.5 cDNA and predicted amino acid sequence is shown in FIG. 3. The sequencing strategy is shown on FIG. 5. The cDNA sequence provides several lines of evidence that the entire coding region is present in the 19.5 clone: 1) There are stop signals in all three reading frames prior to the predicted start position and within the predicted 3' untranslated region; 2) The predicted methionine start site is surrounded by a sequence which matches the GXC AUG G (where X can be A,C,G or U) Kozak consensus sequence for an optimal translation start site (30); 3) A potential polyadenylation signal, ATTAAA, (31) is present 3' of the termination codon.

The derived amino acid sequence gives a predicted (unmodified) protein size of 32,981 daltons and reveals two potential glycosylation sites which are represented by stars in FIG. 3. The predicted amino acid sequence gives a precise estimate of molecular weight which can be altered by either or both glycosylation or phosphorylation. Using IntelliGenetics software programs, four highly hydrophobic, potential transmembrane spanning regions were identified (underlined in FIG. 3). No signal sequence was found. A sketch of a possible membrane associated structure based on the physical properties of the predicted protein is shown in FIG. 4. Although the predicted structure is reminiscent of nicotinic acetylcholine receptor a, no protein or DNA sequence similarity was found. FIG. 3 demonstrates DNA and predicted protein sequence of the 19.5 cDNA clone. FIG. 3 shows the cDNA sequence and predicted amino acid sequence obtained using double stranded sequencing. Microgenie (Beckman) was used to assemble the DNA sequence and to prepare the predicted amino acid sequence. FIG. 5 shows restriction sites within the cDNA used for subcloning and the sequencing strategy used. The open reading frame is indicated by the dotted vertical line. Both strands were sequenced from the intact insert and 4 subclones using primers to the T3 and T7 regions of the plasmid pT7T3 and one synthetic oligonucleotide primer. PC Gene software programs SOAP, HELIXMEM, NOVOTNY, RAOARGOS were used to examine the physical properties of the predicted protein and to prepare the sketch shown in FIG. 4.

EXAMPLE 7

Negative Regulation of 19.5 Gene Expression in Somatic Cell Hybrids

Figure 6:
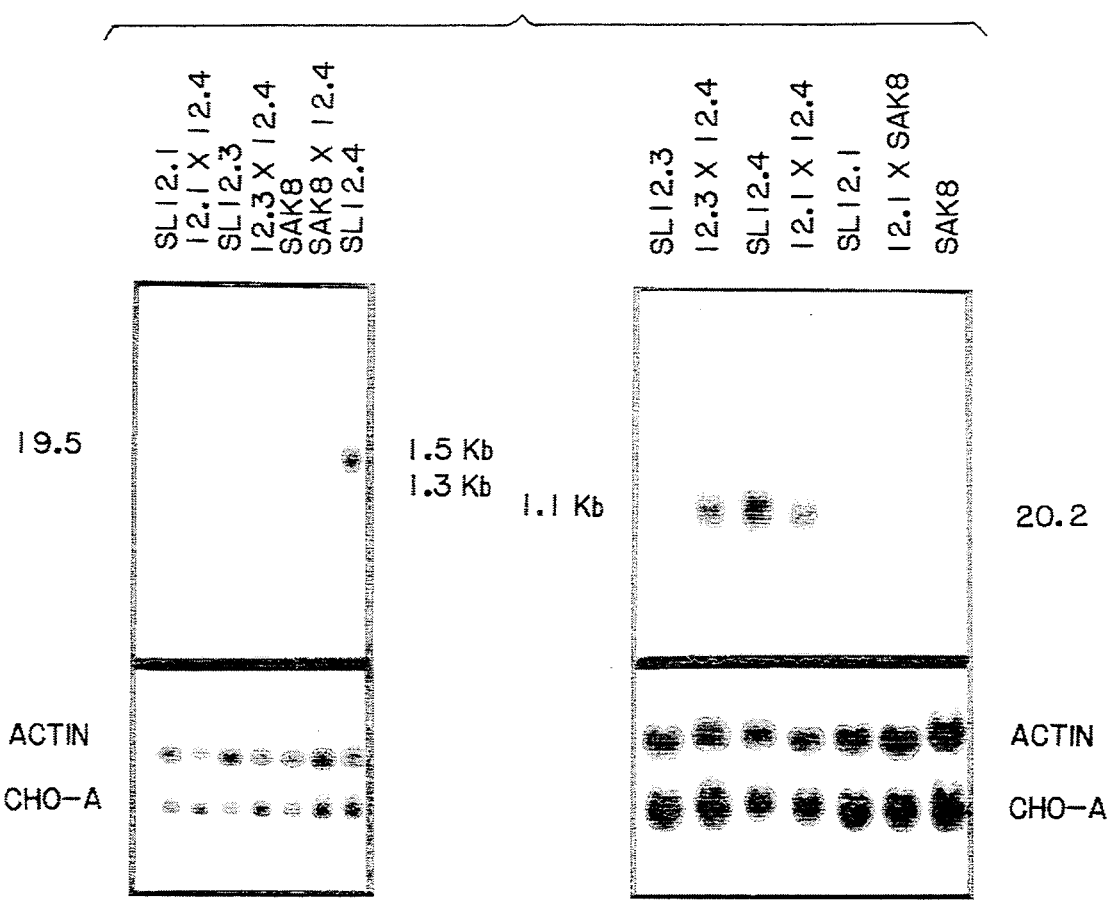
FIG. 6 demonstrates the expression patterns of 19.5 and 20.2 cDNA in somatic cell hybrids.

The differential expression of 19.5 related transcripts in SL12.3 and SL12.4 cell lines was investigated using somatic cell hybrids formed by the fusion of SL12.3 and SL12.4 cells (SL12.3×SL12.4). These hybrids are particularly useful because they have an unusually stable and near-tetraploid chromosome number. The SL12.3×SL12.4 hybrid cells contain 79 chromosomes and have not lost any chromosomes over a period of several years. FIG. 6 shows that the expression of the 19.5 transcripts is strongly repressed in SL12.3×SL12.4 hybrid cells. Furthermore, fusions formed between SL12.4 cells and two other T lymphoma cell lines, SAK8 or SL12.1 which lack expression of 19.5 mRNA (FIG. 6) also result in hybrid cells which lack detectable 19.5 transcripts as illustrated in FIG. 6.

The low amount of 19.5 gene expression in all three somatic cell hybrids does not result from the loss of genes or major gene rearrangements since Southern blots comparing DNA from SL12.3 and SL12.4 cell lines failed to show any detectable differences in band size or intensity as shown on FIG. 2. Additionally, it is unlikely that both chromosomes containing the gene contributed by the SL12.4 parent were lost in three independent hybrids given the near tetraploid chromosome content of the cells and the stability of the karyotype. The gene represented by 19.5 cDNA is negatively regulated in somatic cell fusions formed between SL12.4 cells and three different T cell lines which lack 19.5 gene expression. These results suggest that repressor factors made by SL12.3 may be at least partly responsible for the differential expression of the gene detected by the 19.5 eDNA probe. Similarly, it has been shown that TCR-beta and CD3-delta transcripts are regulated by negative factors present in SL12.3 cells. Since three different T lymphoma cell lines were used as fusion partners with SL12.4 cells and all three fusions fail to express detectable 19.5 mRNA, it is likely that negative factors participate in the regulation of 19.5 gene expression. It is unlikely that mutation or undetectable deletions of both 19.5 alleles from the SL12.4 parent cell would occur in three independent fusions derived from different cell sources.

In studies of somatic cell hybrids between cells of different lineages, the phenomenon of phenotypic extinction is observed whereby most differentiation specific messages no longer accumulate (Davidson, Ann. Rev. Genet. 8:195–218 (1974); Hyman and Stallings, Immunogenetics 6:447–458 (1978)). Phenotypic extinction is uncommon in hybrids formed between closely related cells of the same lineage (Hyman et al., Immunogenetics 10, 261–271 (1980)). When repression occurs in like-lineage somatic cell hybrids, it is usually attributed to specific trans-acting depressors expressed by one of the parental cell lines. In the case of the growth hormone gene, repression in somatic cell hybrids is exerted indirectly on a specific positive activator, GHF1 (McCormick, et al., Cell 55:379–389 (1988)).

EXAMPLE 8

Tissue Distribution of SL12.4 Clone-specific Sequences

Figure 7:
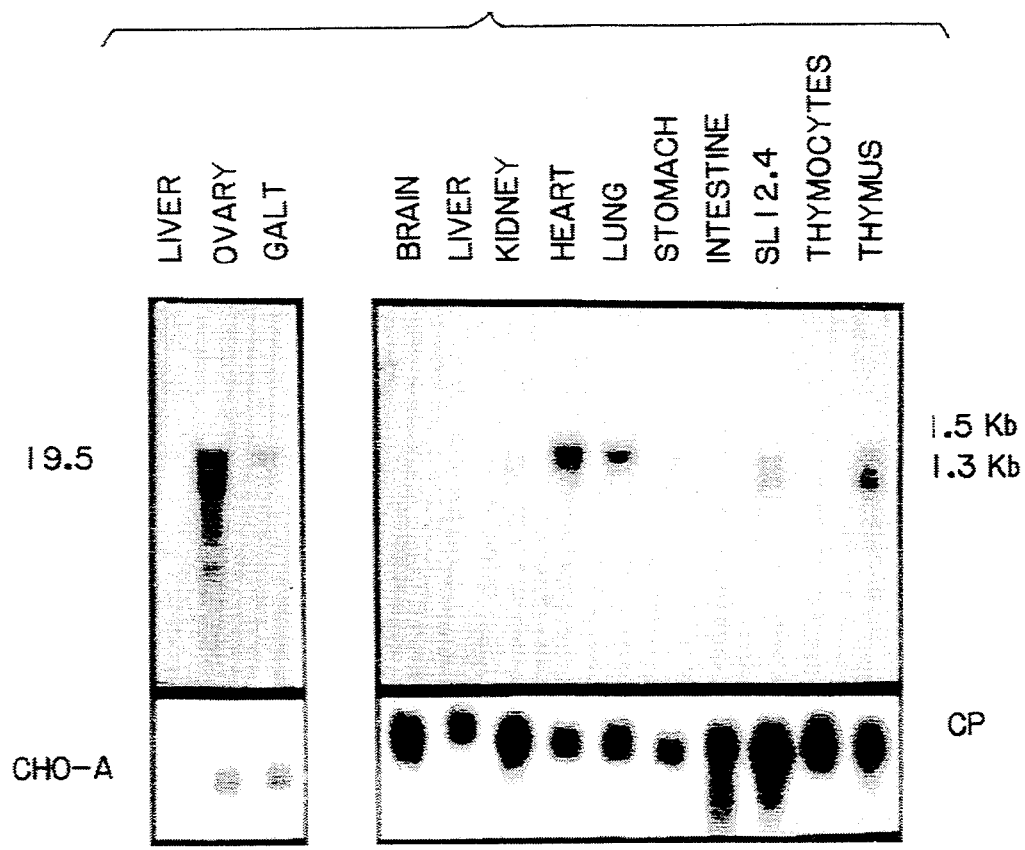
FIG. 7 demonstrates the expression patterns of 19.5 in normal mouse tissue.

RNA derived from a variety of murine tissues was examined to determine whether the gene corresponding to 19.5 is expressed ubiquitously or in a tissue specific manner. FIGS. 6 and 7 demonstrates the expression patterns of 19.5 and 20.2 cDNA in somatic cell hybrids and 19.5 in normal mouse tissue. The northern blots were prepared as described in FIG. 1 and Example 3. FIG. 6 shows RNA from the SL12.3, SL12.4, SAK8 and SL12.1 parental cell lines and hybrid cells, assessed for expression of 19.5 and 20.2 genes. FIG. 7 shows RNA from normal tissues and organs which was derived from Balb/c mice. The transcript sizes were estimated based on their relative migration with actin, cyclophyllin, 18 and 28S ribosomal RNA. The 19.5 cDNA hybridized to two transcripts of 1.7 and 1.5 kb. The blots were probed with random primed 19.5 cDNA insert and subsequently probed with CHO-A, Actin and/or cyclophyllin (CP) to verify that all the lanes contained roughly equivalent amounts of RNA. The CP control appeared to be a more reliable measure of RNA load for normal tissues than actin when assessing RNA from normal cells. All appeared to be equally loaded by acridine orange staining of the gels prior to blotting.

Small amounts of 19.5 mRNA are present in GALT (Gut associated lymphoid tissue, including Peyers' Patch cells), brain, heart and lung and the transcript is quite abundant in ovary (FIG. 7). 19.5 transcripts were not detectable in liver or intestine (FIG. 7), nor in pancreas, testes, bone marrow, quiescent splenocytes, or splenocytes activated by the T cell mitogen Con A (Table 3). Although 19.5 related transcripts are not detectable in unfractionated thymocytes (FIG. 7), nor in purified CD4 CD8 double negative thymocytes, the mRNA is present in whole thymus (FIG. 7) and one thymic epithelial cell line (TEL). Thus, it is likely that thymic stromal cells express the transcript.

Several of the novel cDNA clones identify mRNAs which are not limited in expression to the lymphoid lineage. This finding is similar to other genes which have a known T cell function such as Thy-1 and CD4 which are also expressed in normal brain cells (Lonberg, et al., Mol. Cell Biol. 8:2224–2228 (1988)) and antigen 6C3, a marker for pre-B cell neoplasms, which is also found on cortical epithelial cells of the thymus (Adkins et al., Ann. Rev. Immunol. 5:325–365 (1987)). The expression of 19.5 transcripts in normal ovary and in ovarian carcinoma cell lines is intriguing since the SL12.4 cell line induces prominent extranodal tumors in the ovary of 95% of recipient female animals (14). In contrast, SL12.3 T lymphoma cells form diffuse tumors which do not establish in the ovary (MacLeod, et al., *J. Nat. Cancer Inst* 74:875–882 (1985)) and they do not express 19.5 transcripts. One known human B-lymphoma (Burkitt's) frequently metastasizes to the ovaries (Harrison's *Principles of Internal Medicine.* 11th Edition, (Ed. Braunwald, et al., A. McGraw-Hill, N.Y. (1987)). Since 19.5 cDNA hybridizes to two different human ovarian carcinoma cell lines, there may be a recognition or homing function for the 19.5 gene product which permits it to establish itself and grow in the ovary. Even though 19.5 mRNA is not found in total thymocytes or in fractionated double negative thymocytes, it is possible that the gene is expressed in a rare subset of thymocytes, or is expressed only transiently during fetal or adult lymphopoiesis. In situ hybridization studies will determine the types of cells in the thymus, ovary and heart which express 19.5 related transcripts.

Table 3 summarizes the expression studies carried out on all five cDNA clones (19.5 is included for comparison).

TABLE 3
EXPRESSION of mRNA for NOVEL cDNA CLONES IN MURINE TISSUES

|              | 19.1 | 19.2 | 19.4 | 19.5 |
|---|---|---|---|---|
| SL12.4       | ++   | +++  | +    | +    |
| Thymus       | +    | +++  | +++  | +    |
| Splenocytes  | −    | +    | −    | −    |
| ConA+"       | +    | ++   | ++   | −    |
| GALT         | +    | ++   | −    | +    |
| Bone Marrow  | −    | −    | −    | −    |
| Brain        | −    | +    | −    | +/−  |
| Liver        | −    | +    | −    | −    |
| Lg. Intest.  | −    | −    | −    | −    |
| Pancreas     | −    | −    | −    | −    |
| Ovary        | −    | −    | −    | ++   |
| Testes       | −    | −    | −    | −    |

Relative expression of transcripts complementary to the novel cDNA clones as assessed by Northern analysis. The indicates that the probe detected a transcript from the indicated tissue. In all cases, transcripts from the mouse tissue co-migrated with RNA from the SL12.4 cell line. The − indicates expression at least 10–20 fold less than in SL12.4 cells.

Four of the five cDNA clones detect transcripts in lymphoid tissue: 19.1, 19.2, 19.4 and 19.5 are detectably expressed in the thymus; 19.1, 19.2 and 19.4 expression is induced in Con A stimulated splenocytes; and 19.1, 19.2 and 19.5 are expressed in GALT. Several non-lymphoid tissues contain transcripts which hybridize to 19.2 and 19.5 cDNA probes (FIG. 7 and Table 3).

Human ovarian carcinoma cell lines express sequences complementary to 19.5 cDNA. Since a high level of expression of the 19.5 gene was demonstrated in murine ovarian tissue, ovarian carcinoma cell lines were tested for the presence of the 19.5 sequence. Northern blots of 10 ugs of total RNA from SL12.4 cells and two ovarian carcinoma cell lines were probed as described in FIG. 2. The final wash of the blot on the left was with 2× SSPE at room temperature, the same blot, shown on the right was subsequently washed with 0.2× SSPE at room temperature which resulted in the loss of the signal from the lanes containing the human RNA but not from the lane containing the mouse derived SL12.4 RNA. RNA from two established human cell lines 2008 and COLO 316 was assessed by Northern analysis and found to contain a 1.7 kb transcript which hybridizes to the 19.5 cDNA probe (FIG. 8). The finding that cells of mesodermal epithelial origin express the transcript is somewhat unexpected since these cells comprise only a small percent of the mass of a normal ovary (they are found in a one cell thick layer on the outer surface of the ovary). Ovarian stromal cells may also express the gene.

The presence of transcripts which hybridize to 19.5 cDNA suggest that a gene related to the one encoding 19.5 mRNA is found in the human genome.

Several mammalian species express sequences complementary to 19.5 cDNA. In order to determine whether other mammalian DNAs contain sequences in common with 19.5 by probing a Southern blot of DNA from sea lion, hamster, mouse and human. Southern blots of 10 ug of DNA from the indicated sources digested with PstI was probed with random primed $^{32}P$ labeled 19.5 cDNA insert. The blots were washed with a final stringency of 1× SSPE at room temperature. The lane containing human DNA has a relatively high background. Dots to the right of the lane indicate the reproducibly detected DNA fragments which cross-hybridize with the murine probe. All of the DNAs had simple patterns of hybridization which suggest that the gene has been conserved among mammalian species (FIG. 9). As shown on FIG. 9, complementary sequences have also been detected in rat, rabbit, lemur and orangutan DNA. Thus, it seems that the gene represented by the 19.5 cDNA clone is conserved among mammals. The conservation of this gene suggests that it might have an important, but as yet undiscovered function.

The abundance of transcripts recognized by the novel cDNA probes has not been determined directly. However, by comparison on Northern blots, 19.2 and 19.5 are relatively non-abundant and are expressed in fewer copy number than TCR-beta mRNAs. The observation that four of the genes cloned from SL12.4 cells are detectably expressed in the thymus, three in activated splenocytes and three in GALT cells shows that lymphoma model systems are useful for the isolation of genes which are regulated in normal lymphoid tissues and perhaps in T cell ontogeny.

None of the novel cDNA clones described in this report correspond to published gene sequences. The PC Gene program, Prosite, (IntelliGenetics) was used to examine the predicted proteins represented by 19.2, 19.4, 19.5 and 20.5 cDNAs for potential nucleotide or DNA binding sites, zinc fingers, leucine zippers, enzyme active sites, cellular targeting sites, or features of structural proteins, receptors, cytokines and growth factors. This analysis did not identify sites related to those listed above in any of the predicted proteins. At this time we have no indication of their potential function.

It is possible that these genes encode products involved in differentiation events since: 1) the genes are differentially expressed in the SL12.3 and SL12.4 cell clones which appear to represent distinct stages of thymocyte maturation; 2) the genes display tissue specificity in their expression; 3) 19.1, 19.2 and 19.4 gene expression is induced in splenic T cells activated by the T cell mitogen Con-A; 4) 20.5 and 19.5 related genes are expressed in a stage specific manner in early embryos.

The series of novel cDNA clones are encoded by genes which have interesting patterns of expression and regulation. They will be useful for examining the molecular mechanisms which regulate cellular differentiation, T lymphoma homing and the tumorigenic properties of transformed T cell progenitors. These cDNA clones are also useful as probes to localize cells carrying these novel T-cell genes, and as a source of substantially pure novel T-cell proteins.

EXAMPLE 9

Production of Polyclonal Antibodies against Lov

A 14 amino acid oligopeptide was synthesized at the UCSD Core facility. The sequence of the peptide constructed is K-G,-H-A-D-R-E-Q-E-S-E-E-E-V. This sequence represents the last 13 amino acids at the predicted C-terminal end of Lov with the addition of a $^{14}C$ glycine for use as an indicator of linkage to the carrier. 2 mg of this peptide was linked to 4 mg of the carrier protein keyhole limpet hemocyanin (KLH) by the slow addition of glutaraldehyde over 30 minutes. It was then dialyzed against PBS overnight. 10 ml of sera was obtained from 2 female New Zealand White rabbits (Holbarts-age 6 months) before immunization. The animals were then injected with the conjugated peptide in the presence of Freunds complete adjuvant. 0.2 mg total peptide was injected subcutaneously in 5 sites in the animal. A subsequent boost of 0.2 mg peptide in Freunds incomplete adjuvant was given 4 weeks later. Weekly test bleeds of sera were assessed for the production of anti-Lov antibodies by ELISA.

EXAMPLE 10

Analysis of the Lov Antisera

The presence of antibodies recognizing Lov was monitored by the ELISA assay. The oligopeptide and KLH were dried directly on the ELISA plates in wells. Various dilutions of the antisera were then added and allowed to react for 2 hours. After washing in Blotto, the samples were incubated in a 1:1000 dilution of the secondary antibody (goat anti-rabbit IgG (Fc) linked to horseradish peroxidase) for 2 hours. The horseradish peroxidase catalyzes a colorimetric reaction utilizing $H_2O_2$ and OPD as a substrate. The results are analyzed on an automated ELISA reader. When the titer of antibody reached a plateau, the rabbits were exsanguinated (approximately 9 weeks after initial injection). In ELISA assays using cellular components, cells were lysed by sonication. The membrane fraction was isolated from the cytoplasm by centrifuging the lysate at 45000 g for 30 minutes. Both the membrane and cytosolic fractions were then dried on the ELISA wells overnight.

EXAMPLE 11

Fluorescent Antibody Analysis $10^6$ co-cultivated or untreated SL 12.4 cells were suspended in 25 ul of buffer A (PBS containing 5% fetal bovine serum and 0.02% sodium azide). 50 ul of a 1:100 dilution of the antisera against Lov was then added and allowed to incubate for 30 minutes on ice. Following three washes in buffer A, the cells were then incubated for 30 minutes with a goat anti-rabbit IgG (diluted 1:1000) on ice. In experiments in which the specificity of the interaction was tested, an equal volume of a 1 mg/ml oligopeptide solution was added to the antisera for 30 minutes prior to its addition to the cells. The cells were analyzed on a cytofluorograph 50H fluorescence activated cell porter operating with a laser emitting at 488 nm. Dead cells were gated out due to staining with propidium iodide. 5000 cells were analyzed to generate the resulting histograms.

EXAMPLE 12

Immunoprecipitation of Lov Protein

Immunoprecipitation studies were performed using the procedure described by Harlow and Lane, *In Antibodies: A Laboratory Manual* Cold Spring Harbor Press, N.Y. (1988). Cells were pulse labelled with $^{35}S$ methionine in methionine free medium for 4 hours. The cells were then lysed in either RIPA or NP40 lysis buffer. Lysates were precleared by the addition of 50 ul of preimmune sera incubated on ice for 1 hour and cross reactive proteins immunoprecipitated using Staphylococcus aureus (Calbiochem). Next 5 ul of immune sera was added, incubated for 1 hour, and immunoprecipitated. The material was then washed and electrophoresed on an SDS-PAGE gel. After enhancement, the gel was exposed to film for autoradiographic analysis by methods know to those of skill in the art.

EXAMPLE 13

Genetic Mapping of Lov

The production and characterization of Chinese hamster X mouse somatic cell hybrids has been described previously (Kozak (1983) *J. Virol.* 48:300–303). DNA was isolated from these hybrid cells and digested to completion with PstI, an enzyme which gave patterns unique to each specie when mouse or hamster DNA digests were probed with a 10 kb 19.5 cDNA insert. The digested DNA was electrophoresed on 0.8% agarose gels for 72 hours at 25 volts, and transferred onto nytran membranes. The resulting blots were then probed with $^{32}P$ labelled Lov cDNA and exposed to Kodak XAR film. Evidence of mouse chromosomal contents hybridizing with Lov were observed in several cell lines and the results were analyzed by computer to determine the best candidate for Lov murine chromosomal localization.

EXAMPLE 14

Lov Expression is Induced in SL 12.4 Cells Following Co-cultivation on Thymic Epithelial Monolayers TEL (Glimcher et al., *Scand. J. Immunol.* 17:1–11 (1983)) and TEPI (Beardsley and Hays Proc. Natl. Acad. Sci. USA 80:6005–6009 (1983)) are two immortal thymic epithelial cell lines which can induce stable CD4 and CD8 gene expression in SL 12.4 cells. After SL 12.4 cells were co-cultivated on either TEL or TEPI monolayers for three days, mRNA levels of Lov was assessed. The Northern blot in FIG. 10 shows that both transcripts (1.7, 1.5 kb) of Lov are induced in response to co-cultivation. Both thymic epithelial cell lines are able to elicit this induction, though the expression of Lov after TEL co-cultivation is greater in magnitude as compared to TEPI (Table 4). The values given represent the mean and standard error of five individual experiments after densitometric analysis. Furthermore, the increased levels of Lov mRNA in SL 12.4 cells persist even after the removal of the stimulating thymic monolayers. Nonthymic adherent cells (MME: a mouse mammary epithelial line and AKR1-2B: a fibroblastic line) had no inductive effect on Lov expression in SL 12.4 cells. 100 bp fragments corresponding to the 5' and the 3' region of the Lov cDNA were used to probe Northerns. Both probes recognize both transcripts of Lov.

TABLE 4

Comparison of gene expression after TEL and TEPI cocultivation.

| Gene | cc TEL | cc TEPI |
| --- | --- | --- |
| CD4 | 1.1 ± 0.1 | 1.9 ± 0.3 |
| CD8 | 1.5 ± 0.1 | 2.8 ± 0.5 |
| TCR-α | 2.0 ± 0.1 | 1.5 ± 0.2 |
| lov | 3.7 ± 0.3 | 2.9 ± 0.2 |

Autoradiograms resulting form Northern blots hybridized sequentially with CD4, CD8, TCR-α, 19.5 (lov), and finally with actin/CHO-A were scanned by laser densitometry. The densitometric signals were normalized using actin/CHO-A as a control for the amount of RNA loaded. The values reported represent the ratio of the hybridization intensity of the induced mRNA divided by the uninduced mRNA (thus, they prepresent the mean fold increases ± the standard error of the mean for mRNA accumulation above that detected in untreated SL12.4 cells).

Co-cultivation of these cells on the thymic epithelial monolayer appears to cause the maturation of SL 12.4 cells. In this paper, we showed that a novel gene, Lov, also appears to be induced in SL 12.4 cells following this treatment. The sequence of Lov indicates that the predicted protein encoded would be a surface molecule containing multiple membrane-spanning domains. Both increases in message (three-four -fold inductions) and surface expression of Lov were observed after co-culture on thymic epithelium. These inductions of Lov expression also appear to be stable in that clones isolated following co-culture maintained their high Lov expression even after months of tissue culture. Because of the relatively small induction, nuclear run-on experiments to determine if the induction is explained by transcriptional or post-transcriptional mechanisms cannot be performed.

The Lov mRNA consists of two transcript sizes, 1.7 kb and 1.5 kb. Both of these transcripts are equally induced upon co-cultivation of SL 12.4 cells onto thymic epithelial monolayers. Furthermore, both transcripts are recognized by 5' and 3' probes from the Lov eDNA. It is unknown whether these transcripts arise from alternate start sites, cleavage, polyadenylation signals, or perhaps some other mechanism. However, only the larger transcript is observed in other adult tissues tested which express Lov (ie ovary, heart). In addition, within the developing mouse embryo, there appears to be a shift from the expression of both transcripts to only expressing the larger transcript by Day 15 (data not shown). It is possible that only the 1.7 kb transcript codes for the functional protein in the adult animal.

EXAMPLE 15

Lov Protein is Detectable on SL12.4 Cell Membranes

Figure 11:
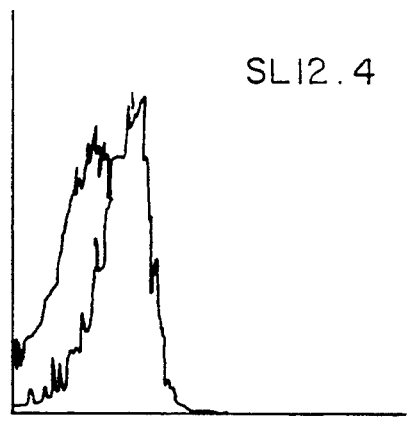
FIG. 11 shows a fluorescent antibody analysis of SL12.4 cells for the surface expression of Lov.
Figure 12:
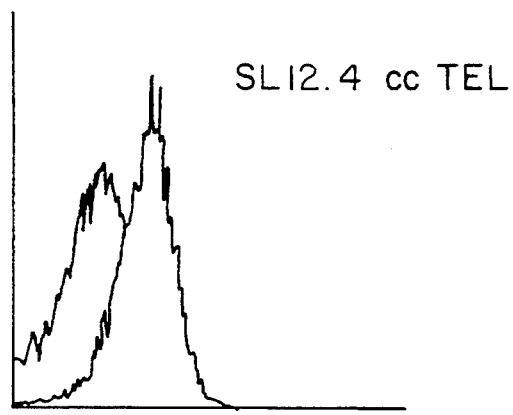
FIG. 12 shows a fluorescent antibody analysis of SL12.4 cc TEL cells for the surface expression of Lov.
Figure 13:
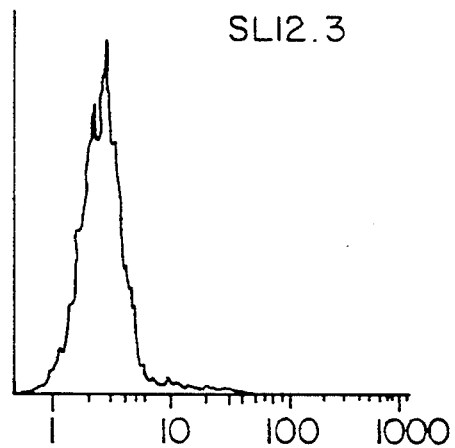
FIG. 13 shows the fluorescence data of a sister lymphoma cell clone, SL12.3 cells, which did not express the mRNA for Lov and did not exhibit any Lov expression on their cell surface.

Antibodies against Lov recognize epitopes found on the plasma membrane of SL 12.4 cells. Polyclonal antibodies against the last 13 amino acids of Lov were raised in rabbits using the synthetic peptide as the antigen. These antibodies recognize an antigen associated with the plasma membrane of SL 12.4 cells. FIGS. 11, 12 and 13 shows a fluorescent antibody analysis of SL 12.4 cells for the surface expression of Lov. The histograms represent fluorescence of SL 12.4 cells stained with the immune sera plotted against SL 12.4 cells stained with the preimmune sera. By viewing permeablized cells under a microscope, the binding of the antibody was only observed on the plasma membrane and did not stain the cytoplasm. Also shown is the fluorescence data of a sister lymphoma cell clone, SL 12.3. SL 12.3 cells did not express the mRNA for Lov and did not exhibit any Lov expression on their cell surface. The binding of the immune sera antibodies to the antigen was also specifically blocked upon the addition of competing amounts of the immunizing oligopeptide (FIG. 14), but not by an irrelevant oligopeptide. Membrane preparations, but not cytosolic fractions, of SL 12.4 cells also showed Lov protein when assessed by ELISA.

The antibody raised against a synthetic oligopeptide corresponding to the carboxy-terminal end of Lov specifically recognizes an epitope found on the surface of SL 12.4 cells. A related cell line, SL 12.3, which does not express Lov mRNA also does not express the protein as assessed by fluorescence. Immunoprecipitations studies of the Lov protein have been performed, but there does appear to be an unusual amount of nonspecific interactions with the preimmune sera. The fact that the Lov protein is probably non-abundant (based on baseline expression of mRNA in these cells) further complicated these experiments. Nevertheless, three specific bands appear to be present upon $^{35}$S-Methionine labelling in SL 12.4 and F6 (a cell clone expressing high Lov), but absent in SL 12.3 cells. These three bands also disappear following the competitive addition of the specific oligopeptide. The 32 Kd band correlates with the predicted molecular weight of the Lov backbone. The 22 Kd band may be a cleavage product whereas the 50 Kd band may represent the glycosylated form of Lov.

EXAMPLE 16

Induction of Surface Expression of Lov

Surface expression levels of Lov was also induced following co-cultivation on the thymic epithelial monolayer for three days. FACS analysis was performed on SL 12.4 cells following co-cultivation on the thymic epithelial monolayer for three days. FIG. 15 shows that the amount of Lov protein detectable on the surface of SL 12.4 cells was inducible after thymic epithelial treatment. The histograms show antisera plotted against prebleed in stimulated and unstimulated SL 12.4 cells. Also shown is the result when co-cultivated SL 12.4 cells on TEL were compared to untreated SL 12.4 cells (lower graph). These graphs are plotted using a logorithmic scale. TEPI cells elicited a similar response for Lov induction.

Figure 16:
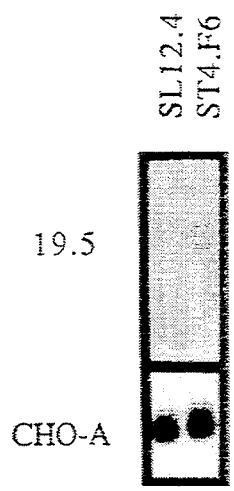
FIG. 16 demonstrates the stability of Lov expression by Northern Blot.
Figure 17:
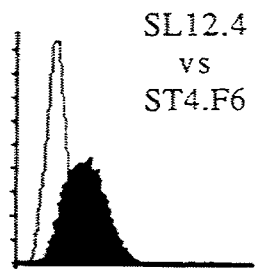
FIG. 17 demonstrates the stability of Lov expression by FACS analysis.

Cell clones previously co-cultivated on thymic epithelial monolayers exhibited a higher basal expression of 19.5. Co-cultivation resulted in higher levels of Lov expression in certain cells. A number of cell clones were isolated from SL 12.4 after co-cultivation on either TEL or TEPI. Cloning was performed by limiting dilution. For example, F6 are cells derived and cloned from an SL 12.4 cell population after it had been co-cultivated on a TEL monolayer for three days. These cell clones have been grown in normal media away from the stimulating thymic epithelium for several months. Both Northern analysis of RNA and FACS analysis for surface protein on F6 demonstrate that this cell clone has a stably higher level of Lov expression than in the parental SL 12.4 cells (FIGS. 16 and 17). Other cell clones isolated and tested exhibit varying amounts of Lov expression. Further co-cultivation of these cell clones on thymic epithelial monolayers does not result in any additional significant increase of Lov expression.

EXAMPLE 17

Chromosomal Localization

Figure 18:
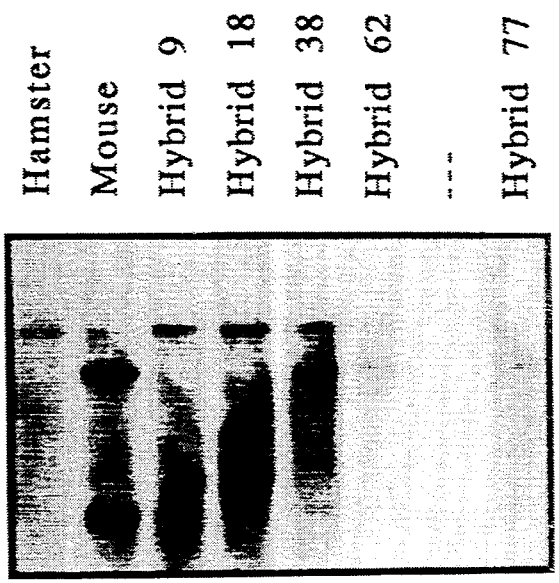
FIG. 18 demonstrates the localization of Lov to chromosome 16.

Genomic DNA was prepared from hamster-mouse somatic hybrid cells containing a complement of a specific set of mouse chromosomes. Restriction enzyme digestion with Pst I gave a different restriction pattern between hamster and mouse (FIG. 18, lanes 1,2). Southern blots of the DNA from these hybrid cells probed with Lov showed that only a few hybrids contained the murine pattern of hybridization (FIG. 8). Based on Southern analysis on a number of these hybrid cell lines, the best correlation is with murine chromosome 16. Sample number 77 is a hybrid cell whose only mouse constituent is Chromosome 16. Table 5 shows the computer analysis illustrating that Chromosome 16 has the least discordancy for Lov in the hybrid cells tested. The Lov gene was further mapped to a specific region of Chromosome 16.

TABLE 5

Analysis of concordance between specific mouse chromosomes and the presence of the Lov gene in a series of mouse-hamster somatic cell hybrids.

| Mouse Chromosome Discordancy | Number of Hybrids DNA Hybridization per Chromosome | | | | Percent |
|---|---|---|---|---|---|
| | +/+ | −/− | +/− | −/+ | |
| 1 | 5 | 6 | 4 | 3 | 38.9 |
| 2 | 6 | 6 | 1 | 4 | 29.4 |
| 3 | 2 | 7 | 4 | 1 | 35.7 |
| 4 | 5 | 9 | 3 | 1 | 22.2 |
| 5 | 2 | 9 | 7 | 0 | 38.9 |
| 6 | 6 | 5 | 1 | 5 | 35.3 |
| 7 | 5 | 4 | 2 | 5 | 43.8 |
| 8 | 4 | 8 | 5 | 2 | 36.8 |
| 9 | 5 | 9 | 4 | 1 | 26.3 |
| 10 | 1 | 9 | 8 | 0 | 44.4 |
| 11 | 0 | 10 | 8 | 0 | 44.4 |
| 12 | 2 | 4 | 2 | 4 | 50.0 |
| 13 | 6 | 7 | 3 | 3 | 31.6 |
| 14 | 3 | 9 | 4 | 1 | 29.4 |
| 15 | 4 | 0 | 1 | 8 | 69.2 |
| 16 | 5 | 9 | 1* | 1* | 12.5 |
| 17 | 5 | 4 | 1 | 4 | 35.7 |
| 18 | 5 | 6 | 2 | 3 | 31.2 |
| 19 | 4 | 5 | 3 | 5 | 47.1 |
| X | 6 | 8 | 3 | 2 | 26.3 |

Mapping of the 19.5 (Lov) gene using mouse-hamster somatic cell hybrids. Symbols indicate the presence (+/) or absence (−/) of the mouse Lov restriction fragment as related to the presence (/+) or absence (/−) of the particular mouse chromosome indicated by the number in the left column detected by hybridization with the 20.5 cDNA probe. The number of discordant observations is the sum of the +/− and −/+ observations.
*Neither of these hybrids were karyotyped. They were typed for other markers, thus it is possible that the exceptions are incorrect assignments of chromosomes.

EXAMPLE 18

Immunoprecipitation of Lov Protein

To determine the size of the Lov protein, immunoprecipitation studies were carried out. Both to label newly synthesized total protein and $^{125}I$ to label surface proteins were used. The preimmune sera from both rabbits had similar nonspecific bands. Although many nonspecific bands were present in the lysates, a few specific bands were identified. Two bands corresponding to a molecular weight of 22 and 32 kd appear to be specific in SL 12.4 cells labelled with $^{35}S$ methionine. Neither band was present in the preimmune sera, nor in lysates made from SL 12.3 cells. The 2 bands are however not seen in $^{125}I$ labelled cells, but instead a 50 kd band is found in SL 12.4, but not in SL 12.3 cells. Attempts were made to reduce the amount of background bands (ie ammonium sulfate precipitation of the IgG fraction, affinity purifying the antibody over a Sepharose column linked with the synthetic oligopeptide, using the clone F6 as the high expresser of Lov), but were unsuccessful in decreasing the nonspecific interactions observed.

Thus, the Lov gene encodes a protein which is expressed on the cell surface. Furthermore, the levels of Lov appear to correlate with the maturation state of these T-lymphoma cell lines. Not only are SL 12.4 cells shifted toward a double positive CD4+CD8+ phenotype after co-cultivation with thymic epithelium, but there also is a coordinate increase in Lov expression in these cells. Lov is a novel cDNA and protein having no significant homologies with any known sequences. Many other T cell markers, such as Thy-1 and T-200, have been described before their function had been determined. Although Lov was isolated from a T lymphoma cell line, other cell types can express this gene. The expression pattern of Lov may reveal some clues to a possible function. The tissues expressing the highest levels of Lov mRNA are the thymus, the gut associated lymphoid tissues (GALT), and the ovaries. The first two loci are normal sites where lymphocytes are found. It is interesting to note that the ovaries are the first sites of tumor formation when SL 12.4 cells are injected into syngeneic mice. Furthermore, the ovaries do contain an extensive lymphatic system. GALT cells, also called Peyers patches, are bounded by high endothelial vessels and it has been shown that the antigen Mel-14 is required for passage through them. SL 12.4 cells express Mel-14 on their cell surface and are therefore a candidate for residence in these specialized areas of the small intestine. Since Lov is expressed on the surface of cells, it may play a role in the homing properties of lymphocytes. Lov was not detected in whole populations of lymphocytes and thymocytes. Perhaps it is only expressed in a certain minority subset of T cells and is not a dominant characteristic. SL12.4 cells may represent a numerically infrequent normal thymocyte.

EXAMPLE 19 cDNA Library Construction and Screening for the 20.5 Gene

Like the other clones, cDNA Library construction and screening for the 20.5 gene was performed as in Examples 1–4. The cDNA insert was removed from lambda DNA by digestion with the restriction enzymes HindIII and BglII and subcloned into the plasmid vector pT7/T3 (Bethesda Research Labs).

EXAMPLE 20

DNA Sequence Analysis of 20.5 or Tea

A restriction endonuclease map was determined and fragments were subcloned into pT7T3, the plasmid purified on cesium chloride and directly sequenced by double stranded dideoxy sequencing methods using Sequenase reagents (U.S. Biochemical Corp., Cleveland, Ohio). Part of the sequence was determined using primers to the host plasmid and other specific oligonucleotide primers (17 mers) were prepared to the cDNA in the UCSD Cancer Center Core Molecular Biology Facility. Both DNA strands were sequenced in their entirety and all sequence was determined in at least two reactions performed in duplicate. Microgenie computer programs were used to assemble the overlapping sequence information and perform the initial analysis of the DNA sequence.

EXAMPLE 21

Genetic Mapping of 20.5

The production and characterization of Chinese hamster X mouse somatic cell hybrids has been described previously by Hoggan, et al., *J. Virol.* 62:1055-1056 (1988). NFS/N strain mice were obtained from the Division of Natural Resources, NIH, Bethesda, Md. *Mus musculus musculus* mice were obtained from a laboratory colony derived from mice originally trapped in Skive, Denmark, and maintained by Dr. M. Potter, (NCI, NIH, Contract NO1-CB2-5584) at Hazelton Laboratories, Rockville, MD. Hybrid NFS/N×*X. m. musculus* females were backcrossed with *M. m. musculus* males to produce the experimental animals. DNAs were extracted from mouse livers, digested with SacI and BamHI, electrophoresed in 0.4% agarose gels for 48 hours at 24 volts and transferred to nylon membranes (Hybond N+, Amersham). Membranes were hybridized with the [$^{32}$P]-labeled 20.5 cDNA and a 438 bp probe representing the DNA polymerase B gene which is present on Chromosome 8 (MacBride, et al, In Press.). Membranes were washed and probed as previously described. Kidney samples from the same mice were typed for inheritance of the markers Gr-1 and Es-1 by histochemical staining after electrophoresis on starch gels (Harris and Hopkinson "Handbook of Enzyme Electrophoresis in Human Genetics," North Holland Publishing Co., Amsterdam (1976) ).

EXAMPLE 22

Isolation and DNA Sequence of the 20.5 cDNA Clone

A 40,000 member SL12.4 cDNA library in ggt10 (16,24) was screened with an SL12.4 cDNA probe subtracted against SL12.3 mRNA. and, simultaneously on duplicate filters with total SL12.3 cDNA as described in above. This screening method was used to characterize the 20.5 gene. Based on the expression characteristics described below, the cDNA clone has been designated Tea (T cell early activation gene). The insert from this clone was sequenced by double-stranded methods on both strands and the sequence is shown in FIG. 19. The cDNA insert is 2397 base pairs in length and contains a single long open reading frame beginning at base pair 409 and extending to 1769. The cDNA does not contain a polyadenylation signal sequence or a poly A tract. The 20.5 cDNA sequence predicts a multiple membrane-spanning protein. FIG. 19 shows the predicted 453 amino acid sequence of the predicted protein which has a molecular weight of 49.57 kilodaltons (unmodified). The cDNA sequence appears to contain the entire coding region since the predicted N-terminal methionine codon is surrounded by a Kozak consensus sequence (GXC AUG G where X can be A,U,G or C), which is an optimal translation start site and the predicted 5' and 3' untranslated regions contain multiple stop codons in all three reading frames. The physical properties of the predicted protein were analyzed using Microgenie and PC gene programs. Three potential N-glycosylation sites are represented by stars in FIG. 19. The predicted protein has nine highly hydrophobic regions (underlined in FIG. 19); 7 of these have characteristics of transmembrane spanning domains based upon an analysis using IntelliGenetics software programs SOAP, HELIXMEM, NOVOTNY, and RAOARGOS.

Figures 20, 21:
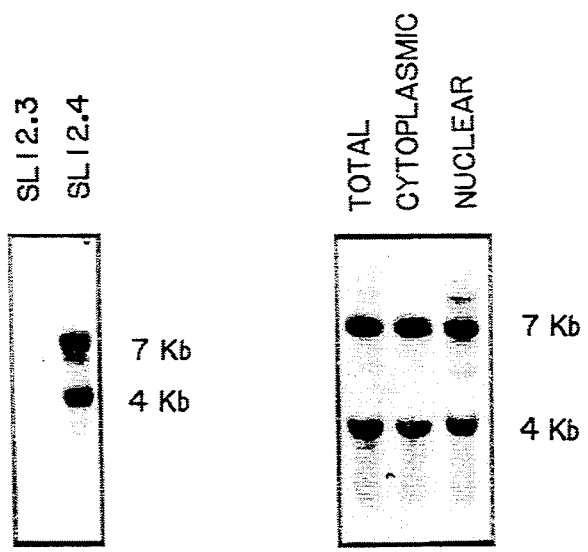
FIG. 20 demonstrates the Tea gene mRNA expression in SL12.3 and SL12.4 cell lines.
FIG. 21 shows Tea mRNA expression in total cellular, cytoplasmic and nuclear RNA from SL12.4 cells.
Figure 22:
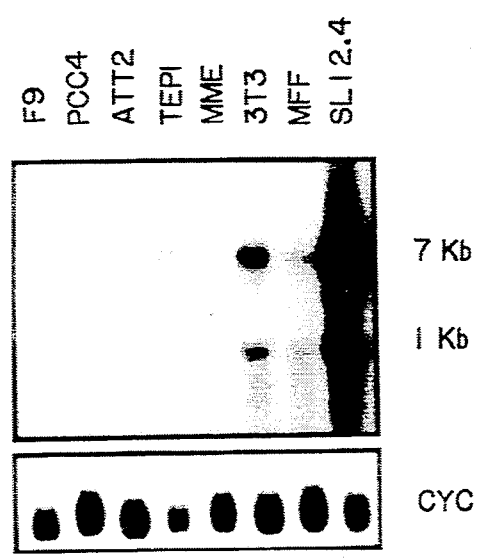
FIG. 22 shows Tea mRNA expression in a series of murine cell lines.

The Tea gene is differentially expressed in T lymphoma cells and activated T lymphoid cells from normal spleen. The expression of transcripts recognized by the 20.5 cDNA clone was assessed. FIGS. 20–23 demonstrates the Tea gene expression. Purified insert containing the entire coding region was labeled with $^{32}$P by random priming and used to probe Northern blots in which each lane contains 10 ug of total cellular RNA (or in the case of FIG. 21, cytoplasmic and nuclear RNA) from SL12.4 cells, SL12.3 cells, the indicated cell lines or tissues from normal Balb/c mice. Autoradiograms of Northern blots are shown in FIG. 20–23. FIG. 20 shows a comparison of Tea mRNA expression in SL12.3 and SL12.4 cell lines. FIG. 21 shows Tea mRNA expression in total cellular, cytoplasmic and nuclear RNA from SL12.4 cells. FIG. 22 shows Tea mRNA expression in a series of murine cell lines described in the text and FIG. 23 contains RNA from the indicated normal tissues from Balb/c mice (GALT is gut associated lymphoid tissue). The size of the transcripts in kilobases (kb) is indicated on each panel was estimated by their relative migration against BRL markers and 18 and 28S endogenous ribosomal RNA. Equivalent loading and transfer of RNA in all lanes was assessed by acridine orange staining and by hybridization with $^{32}$P-cyclophyllin (Cyc) and/or $^{32}$P-Cho-A labeled cDNA.

The 20.5 cDNA probe recognized two transcripts of approximately 4 kb and 7 kb which are present in SL12.4 cells but not in SL12.3 T lymphoma cells (FIG. 20). The subcellular location of the two transcripts was examined to determine whether they were both mature transcripts found in the cytoplasm or whether the larger RNA was a nuclear precursor. Both transcripts appear to be fully processed RNAs since they are found in the cytoplasm (FIG. 21). The origin of the two transcripts is not yet known; they could arise from alternate initiation of transcription, alternate splicing of the transcript or the utilization of alternate polyadenylation signals. Both of the mature cytoplasmic transcripts (7 and 4 kb) are larger than the cDNA clone (2.4 kb). Thus the cDNA is not full length although it does appear to contain the entire coding region. Both transcripts are detected with probes made to a 5' (nucleotide 1 to 380) and a 3' (nucleotide 2005 to 2394) region of the cDNA clone indicating that the cDNA is not a cloning artifact which joined two different transcripts. In addition to the two mature RNAs there are several larger, much less abundant transcripts present in the nuclear and total cell RNA preparations that may be unspliced or partially spliced nuclear precursors (FIG. 21).

Several murine cell lines of embryonic (F9 and PCC4), mammary epithelial (MME) and neuronal (ATt20) origin were examined for the expression of Tea RNA. None of those cell lines express detectable Tea RNA. In contrast, cell lines of thymic epithelial (TEPI) and fibroblast (3T3, MEF) origin contain Tea mRNA, although it is much more abundant in SL12.4 T lymphoma cells (FIG. 22).

Figure 23:
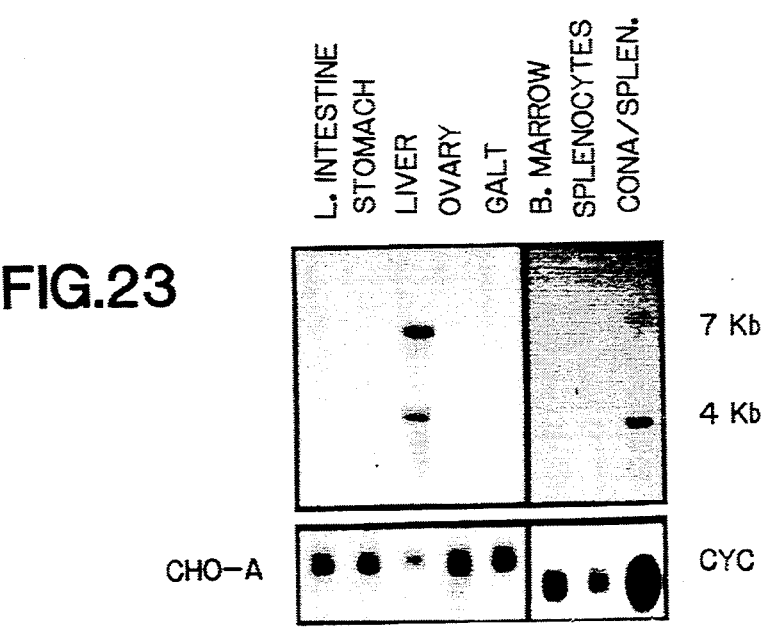
FIG. 23 shows Tea gene expression in RNA from the indicated normal tissues from Balb/c mice. GAL/T is gut associated lymphoid tissue.

To determine whether normal tissues and cells of the lymphoid lineage express the Tea gene, Northern blots prepared from murine tissue mRNA were examined. Cells from thymus, quiescent spleen, gut associated lymphoid tissue (GALT) and bone marrow lack detectable expression of Tea mRNA (FIG. 23). However, Tea transcripts were induced in normal spleen cells activated with the T cell mitogen Concanavalin A (ConA, FIG. 23). ConA was used to mimic the activation of splenic T cells which normally occurs in a cell clone specific manner upon appropriate presentation of foreign antigen. Liver was the only non-lymphoid tissue tested which expressed moderate amounts of Tea mRNA. Tea transcripts were undectable in intestine, stomach, ovary (FIG. 23), brain, heart, lung, kidney, pancreas or testes. Thus, the Tea gene expression is limited to a few cell types such as activated spleen cells, thymic epithelial cells, T lymphoma cells and liver.

EXAMPLE 23

Induction of Tea mRNA

Figure 24:
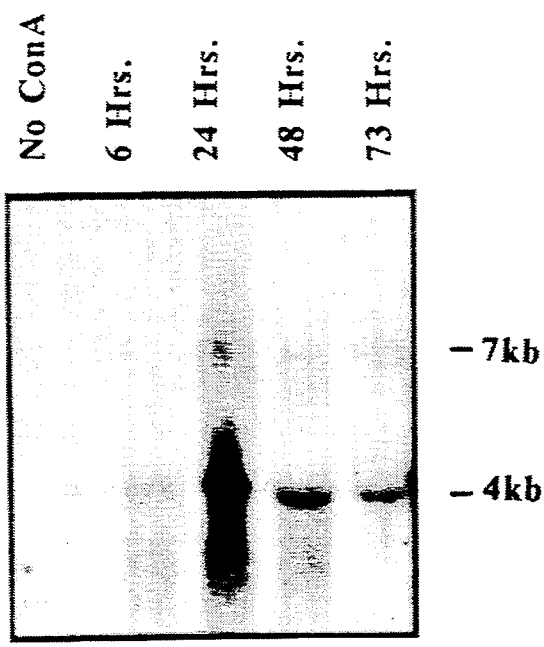
FIG. 24 shows the kinetics of Tea gene induction in activated splenocytes.
Figure 25:
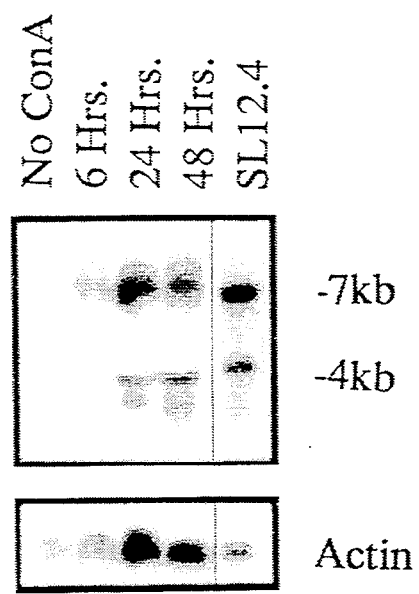
FIG. 25 shows the kinetics of Tea gene induction in activated splenocytes. The control probe indicates the relative amount of mRNA loaded in each lane.

To further investigate the induction of Tea mRNA, RNA was prepared 6, 24, 48 and 72 hours after ConA was added to splenocytes. FIGS. 24 and 25 shows the kinetics of Tea gene induction in activated splenocytes. Northern analysis of RNA from quiescent and activated spleen cells harvested at the indicated times following activation with the T cell mitogen Con A was performed. FIG. 24 shows a 72 hour time point, FIG. 15 show a different blot of RNA together with the control probe cyclophyllin (Cyc) to indicated the relative amount of mRNA loaded in each lane. Unlike Cyc mRNA, the rRNA load was equivalent in each lane as assessed by acridine orange staining. The Tea transcripts are not detectable in quiescent spleen lymphocytes, but becomes detectable within 6 hours, peaking at about 48 hours. Although the total amount of RNA was equivalent in each lane (10 ug), as assessed by acridine orange staining the relative ratio of ribosomal to mRNA appears to change during T cell activation since the amount of actin, CHO-A and cyclophyllin transcripts/10 ug of total RNA increases (FIGS. 24 and 25). However, there is clearly an induction of Tea gene expression relative to these control RNAs during T cell activation.

EXAMPLE 24

Homology of the 20.5 DNA and Amino Acid Sequence with the Murine Ecotropic Retroviral Receptor Homology searches using the Bionet data base revealed no significant sequence similarity between 20.5 cDNA and other DNA sequences previously reported. However, the sequence was compared with a recent report (Albritton, et al., *Cell* 57, 659–666. (1989)) of the murine ecotropic retroviral receptor cDNA clone (ERR) and found to have extensive sequence identity. The gene which encodes the ecotropic retroviral receptor has been designated Rec-1. FIGS. 26 and 27 shows a comparison of the 20.5 cDNA sequence with the ERR cDNA sequence. FIGS. 26 and 27 demonstrates the alignment of 20.5 and ERR cDNA sequences. In FIG. 26, the regions of the ERR and 20.c cDNA sequences included in the alignment analysis is indicated by the vertical lines. The open reading frames for each cDNA are indicated. In FIG. 27, the entire cDNA sequence of 20.5 is shown on the top line of each pair of lines, the cDNA sequence of ERR (bp 400-2425) lacks the first 400 base pairs, and is shown on the bottom of each pair. The horizontal lines mark the positions of sequence identity The comparison was made using Microgenie software with gaps generated to allow alignment of the most highly similar sequences. The percent identity is reported only for the the regions of cDNA which are clearly overlapping. Note the the 20.5 cDNA is much longer at the 3' end and the ERR cDNA is much longer at the 5' end.

The sketch of the two cDNAs (FIGS. 26 and 27) shows that the ERR cDNA is longer at the 5' end, while the 20.5 cDNA sequence is much longer at the 3' end; the two cDNAs are of similar overall length. The coding region of each is depicted by the cross-hatched portion of each cDNA clone. The DNA alignment reveals an overall DNA sequence identity between the overlapping regions of 20.5 cDNA (bp 1 to 2047) and ERR cDNA (bp 400 to 2425) is 59%; one region of 20.5 cDNA (bp 1011-1088) is 80% identical. The 5' noncoding region of the 20.5 cDNA sequence (bp 1 to 410) has 68% sequence identity with the overlapping 5' coding region of the ERR cDNA sequence suggesting that the two genes were derived from a common sequence through a gene duplication event.

Figure 28:
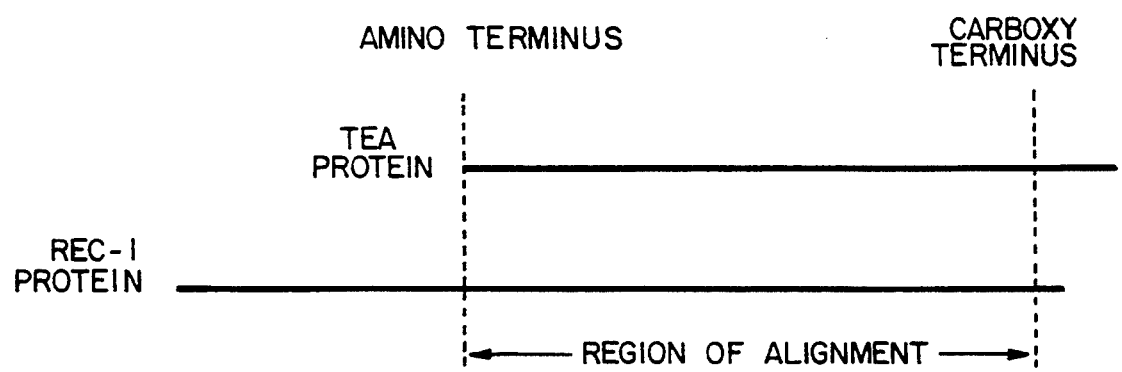
FIG. 28 is a line drawing demonstrating the alignment of Tea predicted protein with the murine ecotropic retrovital receptor protein.

The predicted Tea protein has structural similarity to other proteins with multiple membrane-spanning domains such as the transducing proteins, ion channels, ion pumps, and sugar transporters. However, no significant sequence similarity with these gene families, nor any significant similarity with other known protein sequences were found, with the notable exception of the ERR predicted protein derived from the ERR cDNA sequence. An alignment of the Tea predicted protein with the ERR protein shows two regions of extensive amino acid sequence similarity (FIGS. 28 and 29). FIGS. 28 and 29 demonstrates the alignment of Tea predicted protein sequence with the murine ecotropic retroviral receptor sequence. On FIG. 26, the line sketch shows the region of the two predicted protein products which were compared; the Tea protein extends from amino acid 1–404, the ERR protein from amino acid 204–603. On FIG. 29, the alignment of the two predicted proteins show the amino acid sequence predicted by the 20.5 cDNA on top, by the ERR cDNA on the bottom. The brackets delineate the borders of two regions of extensive amino acid identity; Region 1 is 81.3% identity over 192 amino acids, Region 2 shows 51.9% identity over 79 amino acids. Region 1, defined by brackets, has 81% sequence identity and 91% similarity over 193 amino acids. Region 2 has 62% sequence identity and 75% similarity over a length of 60 amino acids. Conservative amino acid differences (Doolittle, R., *Of Urfs and Orfs: A primer on how to analyze derived amino acid sequences*. University Science Books, Mill Valley, Calif. 1986) are indicated by two dots, amino acid identities are shown by a long dash between the two.

In contrast to Tea predicted gene product, the ERR protein is larger and it has 13-14 predicted transmembrane spanning regions. Futhermore, it has a shorter hydrophilic carboxy-terminus and an amino-terminus of similar length. The predicted carboxy- and amino-termini of the proteins show the most sequence divergence. Similar to ERR and other multiple membrane-spanning proteins, the Tea gene product contains no signal sequence. The comparison shows extensive regions of amino acid similarity, yet the two proteins are clearly distinct gene products.

Figure 30:
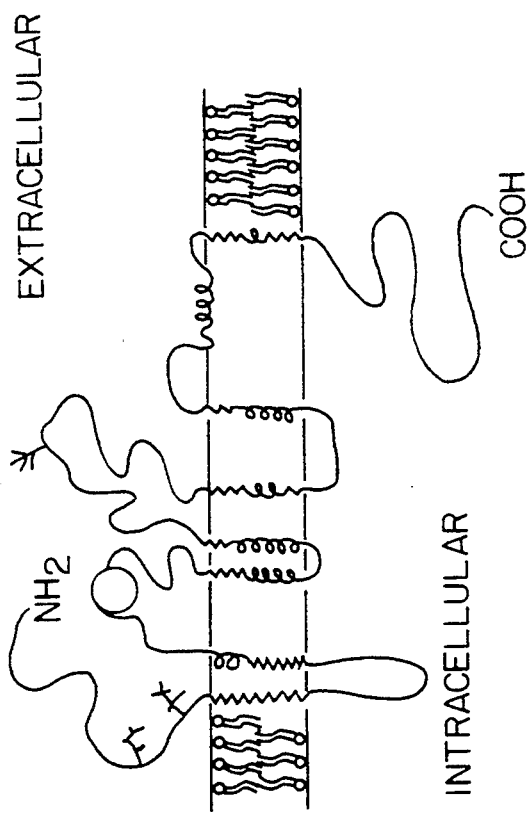
FIG. 30 presents a model for a possible structure of the Tea predicted protein.

FIGS. 30-33 show a sketch of the predicted protein structure prepared using PC gene programs to examine the physical properties as noted in the figure legend. FIGS. 30-33 show the physical properties of the predicted protein products of the Tea and Rec-1 genes. FIG. 30 presents a model for a possible structure of the Tea predicted protein. The bold lines indicate the two regions of extensive similarity with the ERR protein.

Figure 31:
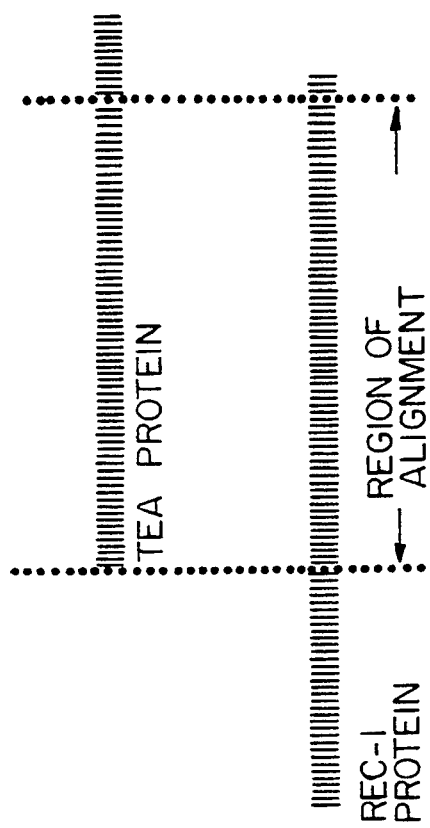
FIG. 31 demonstrates the region of the two predicted proteins which was analyzed and compared for hydrophobicity (amino acid 1–403 for the Tea protein and amino acid 204–603 for the ERR protein).
Figure 32:
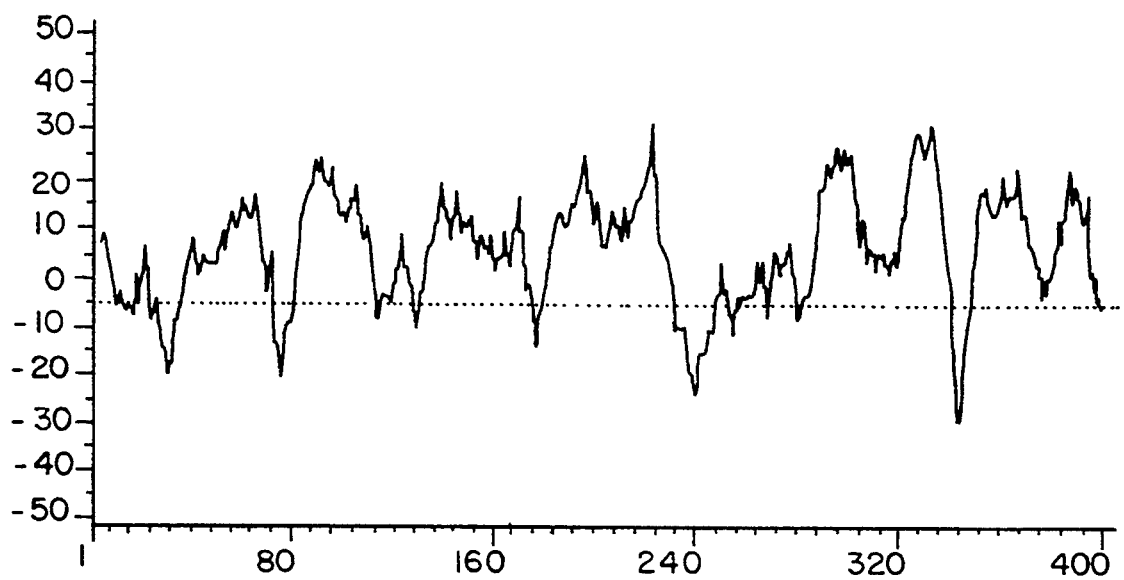
FIG. 32 shows the hydrophobicity properties of the predicted protein products of the Tea genes.
Figure 33:
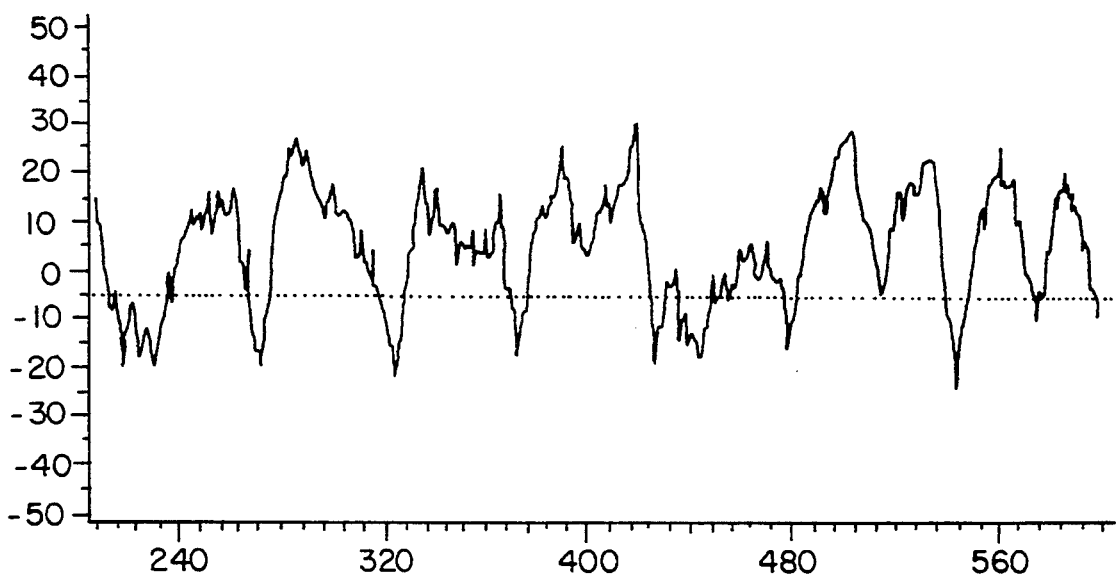
FIG. 33 shows the hydrophobic properties of the predicted protein products of the Rec-1 genes.

PC Gene software programs from IntelliGenetics, SOAP, HELIXMEM, NOVOTNY, RAOARGOS were used to examine the physical properties of the predicted protein to prepare the model shown. FIG. 31 demonstrates the region of the two predicted proteins which were analyzed for the hydrophobicity comparison is shown (amino acid 1–403 for the Tea protein and amino acid 204–603 for the ERR protein). FIG. 32 shows the hydrophobicity plots of the Tea predicted protein and FIG. 33 the ERR predicted protein.

The sketched model highlights the regions of extensive similarity with the ERR protein. Since ERR encodes a cell surface protein, we compared the hydrophobicity profiles of the two predicted proteins in the regions of overlap (amino acids 1–401 of the Tea predicted protein and amino acids 204 to 600 of the ERR protein). FIG. 30 shows the region of the two proteins that was compared in the hydrophobicity plots. The comparison covers a region of 401 contiguous amino acids and shows a remarkable similarity. Thus, it is likely that the product of the Tea gene is also a cell surface protein.

Figure 34:
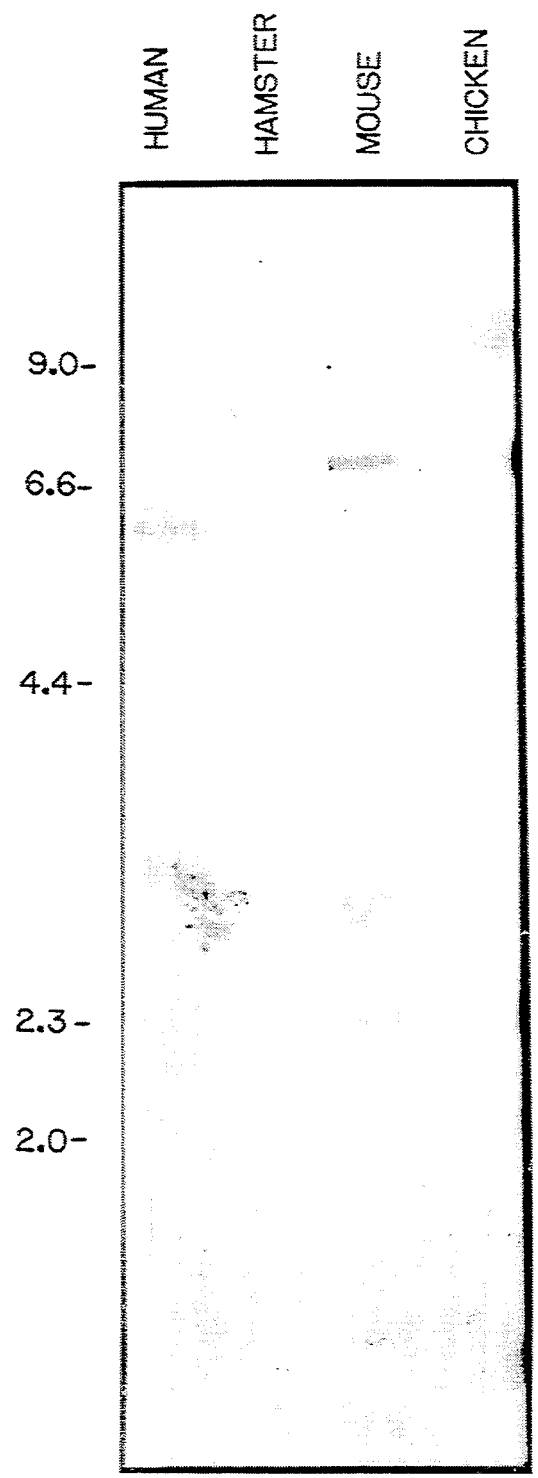
FIG. 34 demonstrates a Southern analysis of DNA from different species.
Figure 35:
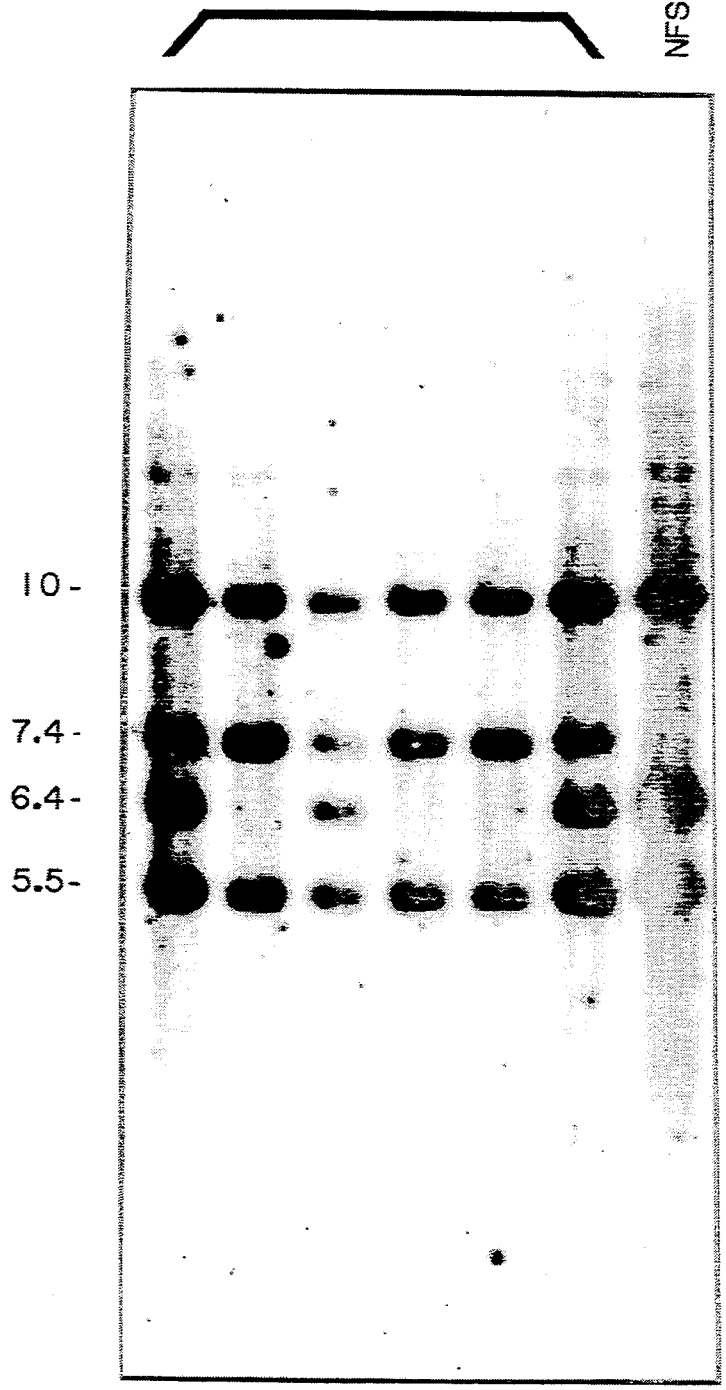
FIG. 35 demonstrates a Southern analysis of recombinant inbred DNA to position the Tea gene on Chromosome 8.
Figure 39:
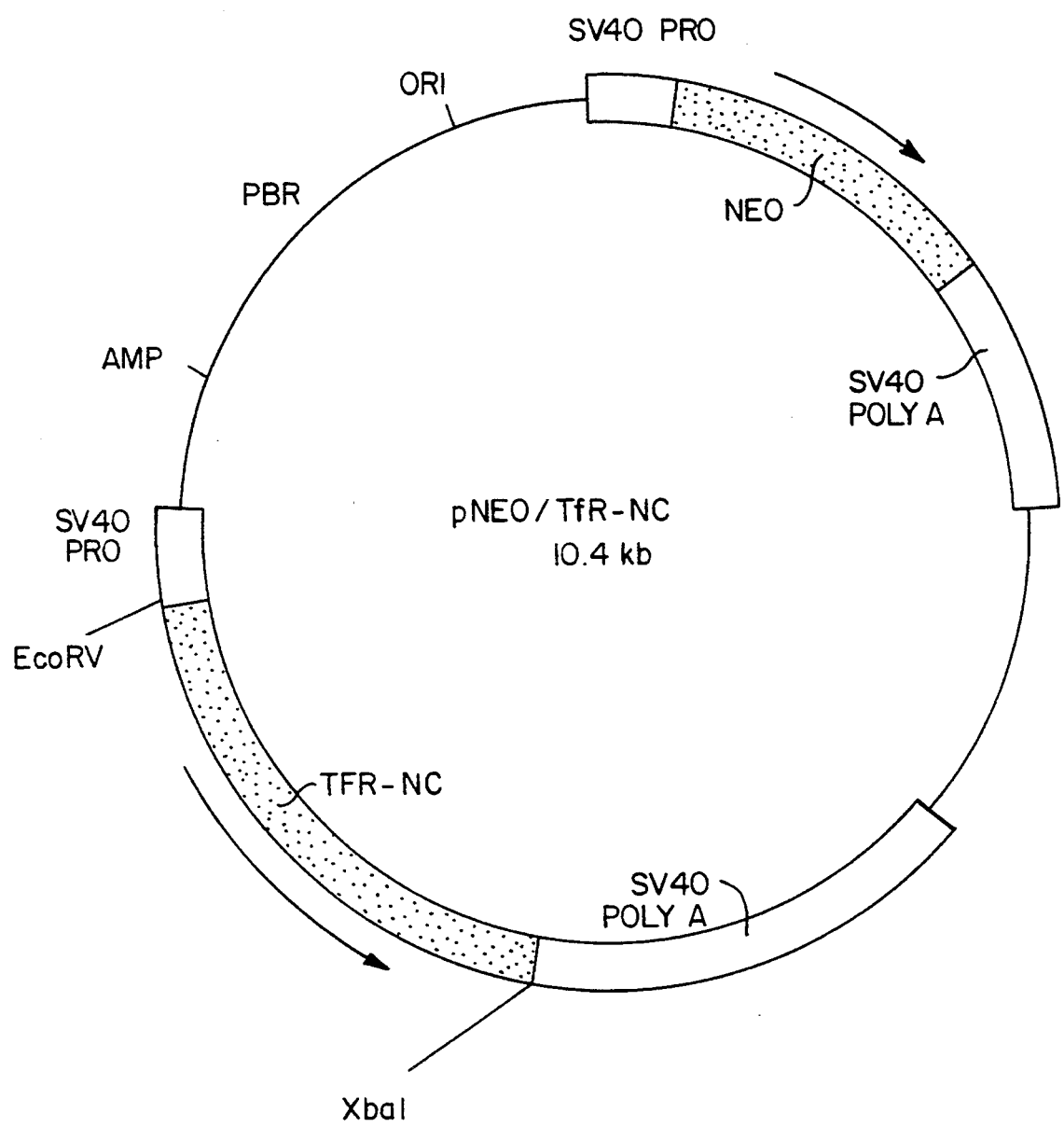
FIG. 39 shows a schematic representation of pNEO/TfR-NC.
Figure 40:
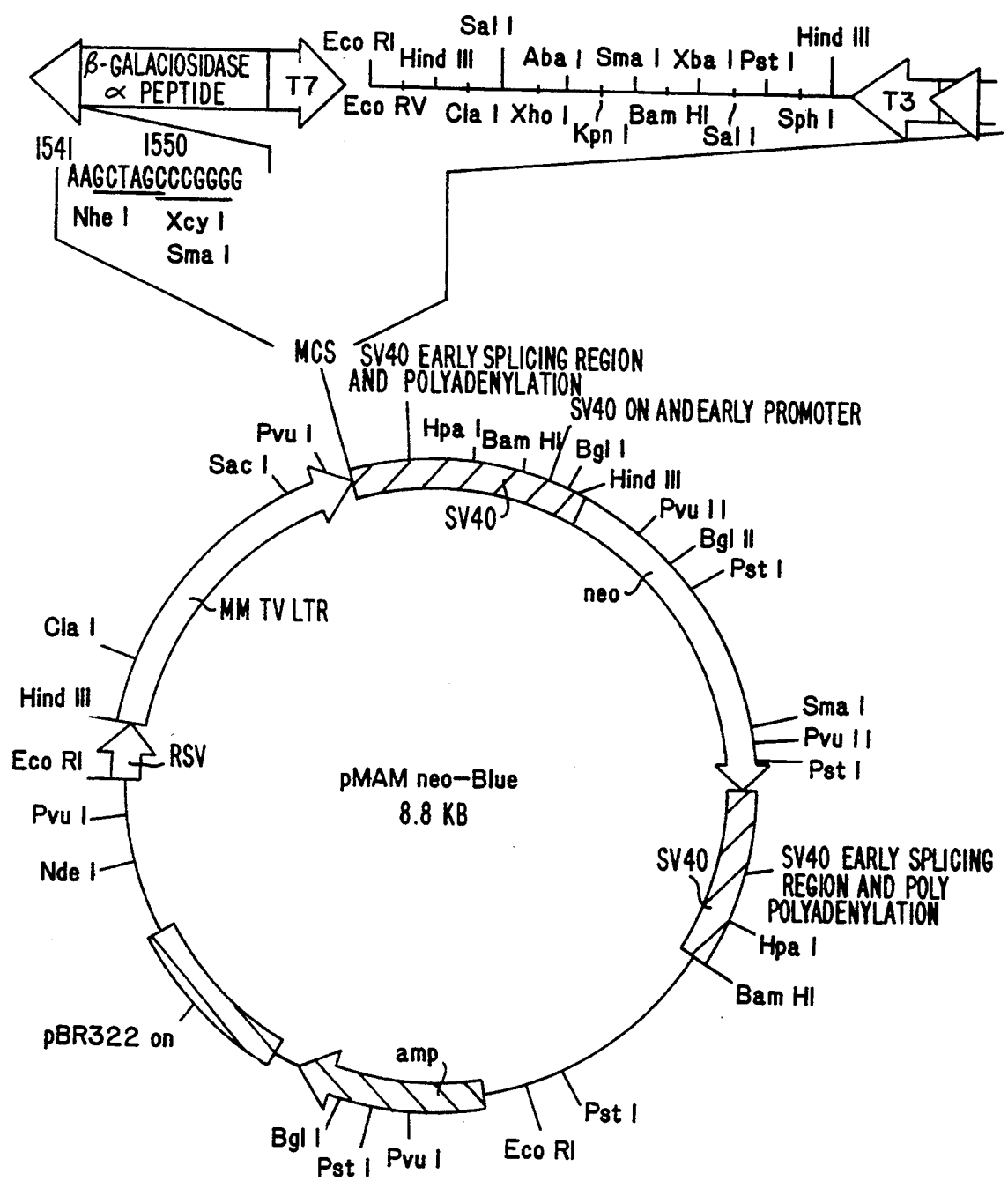
FIG. 40 shows a schematic representation of pMAMneo-Blue.

The Tea gene appears conserved in higher vertebrates. To determine whether the Tea gene sequences are conserved in evolution, DNA from human, hamster, mouse and chicken was tested for cross hybridization with the 20.5 cDNA probe. When the full length cDNA clone was used to probe the Southern blot, detectable hybridization occured with all the genomic DNAs tested (FIGS. 34 and 35). FIGS. 34 and 35 show a Southern analysis of DNA from different species and analysis of recombinant inbred DNA to position the Tea gene on Chromosome 8. The $^{32}P$ labeled cDNA probe for both panels was a nearly full length Bal I fragment of the 20..5 cDNA ozone. FIG. 34 shows an autoradiogram showing the hybridization pattern of PstI digested DNA from human, hamster, mouse and chicken probed with the Bal I fragment as described in Materials and Methods. FIG. 35 represents an autoradiogram of liver DNA derived from recombinant inbred animals. FIGS. 34 and 35 show an example of the pattern of hybridization obtained from several recombinant animals as indicated and from the NFS/N parental DNA digested with SacI.

To test whether any of the DNA fragments detected were derived from the Rec-1 gene, a probe to the 3' region of the 20.5 cDNA clone (which is highly divergent from the ERR eDNA sequence) was found to hybridize to DNA fragments of the same size. These results suggest that the sequences detected by the divergent 3' terminus has also been conserved in evolution and that the cross-hybridization to the DNA of other species was found with the most divergent sequence present between the two cDNA clones. This data, taken together with data from the preceeding section demonstrates that the Tea gene encodes a protein distinct from ERR which is found in other species. The divergence of the amino acid sequence at the carboxy and amino termini suggest that the two proteins may have distinct functions.

EXAMPLE 25

Mapping of the Tea Gene to Chromosome 8.

Since the ERR gene product functions as a viral receptor, the Tea gene was mapped to determine if it was on a chromosome known to encode one of the other known retroviral receptors (Kozak, (1983) *J. Virol.* 48:300–303.). Several different somatic cell hybrids formed between Chinese hamster and mouse cells each retain a limited number of different mouse chromosomes. These hybrids were used to map the Tea gene (Hoggan, et al., (1988) *J. Virol.* 62:1055–1056). Southern analysis of DNAs digested with Pst I from hybrid cells demonstrated that 7 of 21 hybrids contained mouse-specific DNA fragments. A comparison of the known mouse chromosome content with the positive hybridization to mouse-specific DNA fragments indicated that the best correlation is with mouse Chromosome 8 (Table 6).

TABLE 6

Analysis of concordance between specific mouse chromosomes and the presence of the Tea gene in a series of mouse-hamster somatic cell hybrids.

| Mouse Chromosome Discordancy | Number of Hybrids DNA Hybridization per Chromosome | | | | Percent |
|---|---|---|---|---|---|
| | +/+ | −/− | +/− | −/+ | |
| 1 | 5 | 9 | 2 | 4 | 30.0 |
| 2 | 7 | 5 | 0 | 7 | 36.8 |
| 3 | 3 | 6 | 2 | 3 | 35.7 |
| 4 | 4 | 3 | 2 | 3 | 25.0 |
| 5 | 2 | 11 | 5 | 2 | 35.0 |
| 6 | 6 | 6 | 1 | 6 | 36.8 |
| 7 | 5 | 4 | 2 | 8 | 52.6 |
| 8 | 6 | 13 | 1* | 1* | 9.5 |
| 9 | 4 | 10 | 3 | 4 | 33.3 |
| 10 | 0 | 11 | 7 | 2 | 45.0 |
| 11 | 0 | 13 | 7 | 0 | 35.0 |
| 12 | 3 | 4 | 2 | 3 | 41.7 |
| 13 | 5 | 7 | 2 | 7 | 42.9 |
| 14 | 1 | 10 | 5 | 2 | 38.9 |
| 15 | 4 | 0 | 0 | 8 | 66.1 |
| 16 | 3 | 9 | 2 | 4 | 33.3 |
| 17 | 6 | 4 | 0 | 7 | 41.2 |
| 18 | 6 | 6 | 1 | 4 | 29.4 |
| 19 | 5 | 7 | 2 | 5 | 36.8 |
| X | 5 | 8 | 2 | 6 | 38.1 |

Mapping of the Tea gene using mouse-hamster somatic cell hybrids. Symbols indicate the presence (+/) or absence (−/) of the mouse Tea restriction fragment as related to the presence (/+) or absence (/−) of the particular mouse chromosome indicated by the number in the left column detected by hybridization with the 20.5 cDNA probe. The number of discordant observations is the sum of the +/− and −/+ observations.
*Neither of these hybrids were karyotyped. They were typed for other markers, thus it is possible that the +/− hybrid cell contains fragments of Chromosome 8 or a small percentage of the cells contain the chromosome. The −/+ exception may contain a portion of Chromosome 8, but lack the region containing the Tea gene.

To confirm and extend this observation, Tea was positioned on Chromosome 8 by analysis of an interspecies backcross. DNA digested with SstI showed that NFS/N mice produce cross reactive bands of 10.0, 7.4, and 5.5 kb. *M. m. musculus* DNA produces 10, 6.4 and 5.5 kb, fragments. FIG. 35 shows the pattern of hybridization of the 20.5 cDNA probe in backcrosses of NFS/N×*M. m. musculus* F1 mice with *M. m. musculus*. The segregation pattern of this restriction fragment length polymorphism with other markers on Chromosome 8 demonstrated that this gene is linked to Gr-1 and Es-1 with the gene order: centromere-Polb-Gr-1-Tea-Es-1 (Tables 7 and 8).

TABLE 7

Segregation of the Tea hybridizing fragment with alleles of Polb Gr-1 and Es-1 in 57 progeny of an interspecies backcross.

| Mice | Inheritance[a] of the NFS/N Allele | | | | Number of mice |
|---|---|---|---|---|---|
| | Polb | Gr-1 | Tea | Es-1 | |
| Parentals | + | + | + | + | 22 |
| | − | − | − | − | 13 |
| Single Recombinants | + | + | + | − | 5 |
| | − | − | − | + | 9 |
| | + | + | − | − | 0 |

TABLE 7-continued

Segregation of the Tea hybridizing fragment with alleles of Polb Gr-1 and Es-1 in 57 progeny of an interspecies backcross.

| Mice | Inheritance[a] of the NFS/N Allele | | | | Number of mice |
|------|------|------|-----|------|------|
|      | Polb | Gr-1 | Tea | Es-1 |      |
|      | −    | −    | +   | +    | 2    |
|      | +    | −    | −   | −    | 1    |
|      | −    | +    | +   | +    | 5    |

[a] + = Inherited the allele; − = did not inherit the allele.

TABLE 8

| Locus pair | Recombination r/n | cM +/− S.E.[a] |
|---|---|---|
| Polb, Gr-1 | 6/57 | 10.5 +/− 4.1 |
| Gr-1, Tea | 2/57 | 3.5 +/− 2.4 |
| Tea, Es-1[b] | 14/57 | 24.5 +/− 5.7 |
| Polb, Tea | 8/57 | 14.0 +/− 4.6 |
| Gr-1, Es-1 | 16/57 | 28.0 +/− 5.9 |
| Polb, Es-1 | 22/57 | 38.6 Not Significant |

[a] Distances in centimorgans (cM) and standard error for each locus pair were calculated according to Green (19) from the number of recombinants (r) in a sample size of n.
[b] An additional 46 mice were typed for Tea and Es-1 for a total number of recombinants of 24 in 103 backcross mice (23.3 cM +/− 4.2).

The location of the Tea gene on Chromosome 8 provides proof that the gene is distinct from the Rec-1 gene which encodes ERR and is localized to Chromosome 5. It also eliminates the possibility that Tea is the MCF retroviral receptor, which has been localized to Chromosome 1 although there is not yet sufficient data to determine if it is related to the receptor for A/10 virus which has not yet been mapped to a chromosome.

Seventy genes or gene products are known to increase in expression when T cells activated in response to a combination of antigen and self-histocompatibility molecules on the surface of antigen-presenting cells. Polyclonal activators such as lectins, calcium ionophores or antibodies to the T cell receptor for antigen can mimic the response induced by antigen. Some of these "activation" genes are involved in the transition between $G_0$ and $G_1$ of the cell cycle. Some encode cytokines and their receptors, nuclear regulatory proteins and still others are involved in the transport of ions and nutrients into the cells to prepare them for growth. At least 26 T cell "activation" gene products have been localized to the cell membrane. 20.5 is the first example of a cloned gene or cDNA that has the potential to encode a multiple transmembrane-spanning protein which is induced during T cell activation.

The process of splenic T cell activation initiated by ConA or antigen begins within minutes of contact with pectin or antigen presentation and continues over a period of about 7–14 days. Changes in gene expression occur throughout the activation period. Crabtree has categorized these changes in gene expression by analogy with viral gene activations (immediate, early, late and very late). By Crabtree's criterion, Tea is an early gene because Tea mRNA is virtually undetectable in normal quiescent T cells, increases to detectable levels within 6 hours and peaks at about 24 hours. The function of the Tea gene is not yet known; it could function to transduce signals or transport small molecules which are signal transducers, or it could function as a receptor for an unidentified ligand. The rather long carboxy terminus of the putative Tea protein might function as a signal transducer, although no evidence to support that speculation exists. Since SL12.3 T lymphoma cells and numerous other T and B tumor cell lines do not express this gene, Tea gene expression is not required for cell growth. However, our studies do not exclude the possibility that normal T cells require Tea gene expression to undergo the normal cell proliferation which accompanies T cell activation. Interference with the expression of this gene could block activation of T cells in autoimmune diseases, such as arthritis diabetes and other T cell mediated immune diseases.

The striking homology between the Tea and ERR proteins suggest that Tea gene product might function as a murine retroviral receptor since at least four classes of murine retroviral receptors have been genetically defined and only one has been molecularly cloned. The localization of the Tea gene to Chromosome 8 eliminates the possibility that Tea encodes the recombinant ecotropic MCF virus receptor and raises the possibility that it could encode the amphotropic retroviral receptor which has been localized to Chromosome 8. In contrast to the Rec-1 gene (encoding ERR), which is ubiquitously expressed in mouse tissues, Tea gene has a much more limited tissue distribution. If the Tea gene encodes a protein which functions as a retroviral receptor, limited tissue distribution could provide specificity for the retroviruses which are restricted to the lymphoid lineage. A precedent for receptor mediated restriction is the human retrovirus HIV which uses the CD4 protein as its primary receptor. However, cell specific receptors are unlikely to be entirely responsible for tissue specificity of murine retroviruses. The tissue tropism exhibited by retroviruses is likely to result from a complex series of factors such as the tissue specificity of LTRs, variations in gp70 env proteins, cellular factors and/or the expression of appropriate cell surface receptors. When the ERR binding site for virus is identified, it will be possible to determine whether the site is in a region of high similarity with the Tea protein. Viral binding and infection studies are required to determine whether Tea protein functions as a viral receptor.

In spite of the high degree of similarity to the ERR gene product, there are substantial differences in the physical properties of the Tea and ERR predicted proteins. They map to different chromosomes and their tissue expression patterns are distinct. Since the natural cellular functions of both these genes are unknown, further study is required to determine any functional similarities that might exist between the two proteins. An analysis of the conserved and nonconserved amino acids may provide insight into similar or disparate functions of ERR protein and Tea gene product. In particular, the identification of this new gene family and the regions of DNA sequence which are highly conserved between the two molecules will now permit searches for new members of the gene family.

The vectors designated pT7T3-19.1 (Deposit Accession No. 68298, pT7T3-19.2 (Deposit Accession No. 68299), pT7T3-19.4 (Deposit Accession Nos. 68300, 68301, and 68302), pT7T3-19.5 (Deposit Accession No. 68303), and pT7T3-20.5 (Deposit Accession No. 68305) were deposited with the American Type Culture Collection (ATCC), Rockville, Md., U.S.A., on Apr. 13, 1990. The deposits are available pursuant to the patent laws and regulations of the United States and of those countries foreign to the United States in which counterparts of this application are filed. The availability of the deposit does not constitute a license to practice the invention of this application in derogation of any patent issued thereon or on any division or continuation of this application.

The invention now being fully described, it will be apparent to one of ordinary skill in the art that many changes and modifications can be made thereto without departing from the spirit or scope of the invention as set forth below.

---

What is claimed as new and is desired to be covered under Letters Patent is:

1. A isolated and purified polypeptide consisting of the amino acid sequence of a T cell protein encoded by the genes selected from the group consisting of 19.5 (seq. id. no.4), 20.5 (seq. id. no.5), 19.2 (seq. id. no.2), and 19.4 (seq. id. no.3).

2. The polypeptide of claim 1, wherein said T cell protein is encoded by DNA of T lymphoma.

3. The polypeptide of claim 1, wherein said amino acid sequence is encoded by the nucleic acid sequence shown by FIG. 3.

4. The polypeptide of claim 1, wherein said amino acid sequence is encoded by the nucleic acid sequence shown by FIG. 13.

5. The polypeptide of claim 1, wherein said amino acid sequence is encoded by the nucleic acid sequence shown by FIG. 21.

6. The polypeptide of claim 1, wherein said amino acid sequence is encoded by the nucleic acid sequence shown by FIG. 22.

* * * * *

UNITED STATES PATENT AND TRADEMARK OFFICE
CERTIFICATE OF CORRECTION

PATENT NO.   : 5,440,017
DATED        : August 8, 1995
INVENTOR(S)  : Carol L. MacLeod Page 1 of 3

It is certified that error appears in the above-identified patent and that said Letters Patent is hereby corrected as shown below:

Column 2,
Line 47, "hematopoeitic" should read -- hematopoietic --.

Column 3,
Line 4, please delete the second period after the word "*Acad*".

Column 4,
Line 13, please insert a period at the end of the line.
Line 50, "Cell" should read -- cell --.

Column 9,
Line 52, "+-" should read -- ++ --.

Column 10,
Line 24, "Dubellco's" should read -- Dulbecco's --.
Line 25, "Eagles" should read -- Eagle's --.
Line 57, "Dephosphorlyated" should read -- Dephosphorylated --.
Line 66, please insert a comma after the word "(1980)" and after the period.

Column 11,
Line 28, please insert a period after the word "isolates".
Line 60, "isothiocynate" should read -- isothiocyanate --.

Column 12,
Line 40, "12:267-284" should read -- 13:267-284 --.
Line 57, "romm" should read -- room --.

Column 14,
Line 5, "Science" should read -- *Science* --.
Line 6, "Cell" should read -- *Cell* --.
Line 7, "J. Virol." should read -- *J. Virol* --.
Line 26, "ORFS" should read -- ORFs --.

Column 15,
Line 56, "eDNA" should read "cDNA".

UNITED STATES PATENT AND TRADEMARK OFFICE
CERTIFICATE OF CORRECTION

PATENT NO. : 5,440,017
DATED : August 8, 1995
INVENTOR(S) : Carol L. MacLeod

It is certified that error appears in the above-identified patent and that said Letters Patent is hereby corrected as shown below:

Column 17,
In the legend for Table 3 starting at line 35, please insert -- + -- between the words "The" and "indicates".

Column 18,
Line 8, please insert a comma after the word "human".
Line 38, "eDNA" should read "cDNA".

Column 19,
Line 7, please delete the period after the letters "K-G" and replace it with an asterik.

Column 20,
Line 6, please insert comma after the word *"Manual"*.
Line 19, "know" should read -- known --.
Line 45, please insert a comma after the word "Hays".
Lines 45-46, "Proc. Natl. Acad. Sci. USA" should read -- *Proc. Natl. Acad. Sci. USA* --.

Column 21,
In the title of Table 4, starting on line 3, "cocultivation" should read -- co-cultivation --.
In the legend of Table 4, starting on line 9, "form" should read -- from --.

Column 23,
Line 55, please insert -- $^{35}S$ -- between the words "Both" and "to".

Column 26,
Line 23, "is" should read -- as --.
Line 47, "eDNA" should read -- cDNA --.

Column 27,
Line 7, "undetable" should read -- undetectable --.
Line 24, "show" should read -- shows --.
Line 25, "indicated" should read -- indicate --.
line 56, "20.c" should read -- 20.5 --.
Line 64, please insert a period after the word "identity".
Line 68, please delete the first word "the" and replace it with -- that --.

Column 29,
Line 7, "is" should read -- as --.
Line 35, "20..5" should read -- 20.5 --.

UNITED STATES PATENT AND TRADEMARK OFFICE
CERTIFICATE OF CORRECTION

PATENT NO.    : 5,440,017
DATED         : August 8, 1995
INVENTOR(S)   : Carol L. MacLeod It is certified that error appears in the above-identified patent and that said Letters Patent is hereby corrected as shown below:

Column 29,
Line 7, "is" should read -- as --.
Line 35, "20..5" should read -- 20.5 --.
Line 35, "ozone" should read -- clone --.

Column 31,
In Table 7, on line 8 (which is the second line, that reads "- - - - 1" should read
    --+- - - 1 --.
In Table 7, on line 9, (which is the third line, that reads "- - - - 5"
should read --- + + + 5 --.
Line 36, please insert the word -- are-between the words "cells" and "activated".

Column 32,
Line 9, please insert a comma between the words "arthritis" and "diabetes".
Line 58, please insert a comma after the numers "68298".

Column 45,
Line 35, "A" should read -- An --.

Column 46,
Line 34, "FIG. 13" should read -- FIG. 19 --.
Line 37, "FIG. 21" should read -- FIG. 37 --.
Line 40, "FIG. 22" should read -- FIG. 38 --.

Signed and Sealed this

Twenty-first Day of August, 2001

*Attest:*

NICHOLAS P. GODICI
*Attesting Officer*    Acting Director of the United States Patent and Trademark Office